United States Patent [19]
Hill et al.

[11] Patent Number: 6,060,507
[45] Date of Patent: May 9, 2000

[54] USE OF MASSOIALACTONE FOR INHIBITION OF FUNGAL GROWTH

[75] Inventors: Robert Anthony Hill, Taupiri, New Zealand; Horace G. Cutler, Watkinsville, Ga.; Stephen Robert Parker, Hamilton, New Zealand

[73] Assignee: Horticulture and Food Research Institute of New Zealand Limited, Palmerston North, New Zealand

[21] Appl. No.: 08/919,726

[22] Filed: Aug. 28, 1997

Related U.S. Application Data

[63] Continuation-in-part of application No. 08/781,145, Jan. 10, 1997, abandoned, which is a continuation of application No. 08/385,041, Feb. 7, 1995, abandoned.

[30] Foreign Application Priority Data

Feb. 7, 1994 [NZ] New Zealand ............................ 250838
Feb. 8, 1994 [NZ] New Zealand ............................ 250851
Aug. 4, 1994 [NZ] New Zealand ............................ 264171

[51] Int. Cl.[7] .......................... C07D 309/00; A01N 43/16
[52] U.S. Cl. ......................... 514/460; 549/273; 549/294
[58] Field of Search ............................ 514/460; 549/273, 549/294

[56] References Cited

U.S. PATENT DOCUMENTS

| | | | |
|---|---|---|---|
| 4,235,780 | 11/1980 | Kondo et al. ............................ | 549/273 |
| 4,701,539 | 10/1987 | Kondo et al. ............................ | 549/294 |
| 4,915,944 | 4/1990 | Chet et al. ............................ | 435/254.6 |
| 5,238,690 | 8/1993 | Elad et al. ............................ | 435/256.7 |
| 5,260,213 | 11/1993 | Harmon et al. ............................ | 435/254.6 |

OTHER PUBLICATIONS

Derwent Abstract WPIL 94–252287/31 Besnard et al FR2700542 "New Antifungal–6–Alkyl–Delta–Lactone CPDS . . . From New Trichoderma Strains" Jul. 22, 1994.
Derwent Abstract WPIL 88–107145/16 Belin et al FR2603048 "Production of Sec. Metabolites For Flavouring . . . By Selecting New Fungal Strains and Growing on Agro–Industrial Substrate" Feb. 26, 1988.
Derwent Abstract WPIL 84–277610/45 Boirie et al EP–124388 "Trichoderma Harzianum Strain and Trichorzianine Peptide–Isolated From the Strain and Isolated 6–Pentyl–2–Pyrone Are Antifungals For Botrytis Cinerea Etc" Nov. 7, 1984.
Derwent Abstract WPIL 93–167286/20 Buergel et al WO9308694 "New Fungicidal Trichoderma Strains LCL, LC2 and LC3 ——" May 13, 1993.
Derwen Abstract WPIL 97–161491/15 Nippon Suisan Kaisha LTD JP09031071 "Prodn of R–Massoia Lactone–Useful as Perfume Ormodulating Agent For Foods, Drinks Cosmetics and Medicines" Feb. 4, 1997.

*Primary Examiner*—Herbert J. Lilling
*Attorney, Agent, or Firm*—Knobbe, Martens, Olson & Bear LLP

[57] ABSTRACT

Massoialactone is useful for preventing or at least inhibiting growth of a fungus. Accordingly, a fungicidal composition has massoialactone as an active antifungal compound together with an agronomically acceptable carrier therefor. Additional antifungal ingredients can be added to the composition. The composition can be applied to surfaces, including surfaces of plants and plant parts, such as seeds.

10 Claims, 33 Drawing Sheets

FIG. 9

RESULTS AFTER 6 DAYS INCUBATION (25° C)

| Trtmt. | Fungi | 100% Inhib. | 75% mm | 75% Inhib. | 50% mm | 50% Inhib. | 25% mm | 25% Inhib. | 10% mm | 10% Inhib. | 5% mm | 5% Inhib. | 2.50% mm | 2.50% Inhib. | 1% mm | 1% Inhib. | 0.05% mm | 0.05% Inhib. | mm |
|---|---|---|---|---|---|---|---|---|---|---|---|---|---|---|---|---|---|---|---|
| 1 | Penicillium | + | 17 | + | 12 | + | 12 | + | 13 | – | – | – | – | – | – | – | – | – | – |
|   | Botrytis | + | 31 | + | 23 | + | 20 | + | 20 | + | 7 | + | 3 | – | – | – | – | – | – |
|   | Yeast | + | 27 | + | 16 | + | 12 | + | 12 | – | – | + | 6 | + | 1 | – | – | – | – |
|   | FK150 | + | 22 | + | 18 | + | 15 | + | 15 | + | 5 | + | 3 | – | – | – | – | – | – |
|   | FK36 | + | 21 | + | 18 | + | 16 | + | 16 | – | – | + | 2 | – | – | – | – | – | – |
|   | FK64 | + | 21 | + | 18 | + | 18 | + | 17 | – | – | – | – | – | – | – | – | – | – |
|   | FK304 | + | 10 | + | 10 | + | 10 | + | 8 | – | – | – | – | – | – | – | – | – | – |
| 2 | Penicillium | + | 17 | + | 14 | + | 13 | + | 13 | + | 1 | – | – | – | – | – | – | – | – |
|   | Botrytis | + | 32 | + | 20 | + | 22 | + | 21 | + | 5 | – | – | – | – | – | – | – | – |
|   | Yeast | + | 27 | + | 15 | + | 15 | + | 12 | + | 9 | + | 3 | – | – | – | – | – | – |
|   | FK150 | + | 21 | + | 19 | + | 20 | + | 15 | + | 4 | + | 3 | – | – | – | – | – | – |
|   | FK36 | + | 18 | + | 17 | + | 18 | + | 15 | + | 2 | – | – | – | – | – | – | – | – |
|   | FK64 | + | 20 | + | 21 | + | 19 | + | 16 | + | 6 | – | – | – | – | – | – | – | – |
|   | FK304 | + | 11 | + | 13 | + | 10 | + | 9 | – | – | – | – | – | – | – | – | – | – |
| 3 | Penicillium | + | 15 | + | 10 | + | 9 | + | 8 | – | – | – | – | – | – | – | – | – | – |
|   | Botrytis | + | 32 | + | 20 | + | 20 | + | 16 | – | – | – | – | – | – | – | – | – | – |
|   | Yeast | + | 12 | + | 7 | + | 5 | + | 5 | + | 4 | – | – | – | – | – | – | – | – |
|   | FK150 | + | 16 | + | 15 | + | 14 | + | 13 | + | 2 | – | – | – | – | – | – | – | – |
|   | FK36 | + | 13 | + | 14 | + | 14 | + | 10 | – | – | – | – | – | – | – | – | – | – |
|   | FK64 | + | 12 | + | 17 | + | 16 | + | 13 | + | 4 | – | – | – | – | – | – | – | – |
|   | FK304 | + | 9 | + | 2 | + | 2 | – | – | – | – | – | – | – | – | – | – | – | – |
| 4 | Penicillium | + | 17 | + | 18 | + | 17 | + | 15 | + | 7 | – | – | – | – | – | – | – | – |
|   | Botrytis | + | 30 | + | 22 | + | 23 | + | 20 | + | 11 | + | 4 | – | – | – | – | – | – |
|   | Yeast | + | 19 | + | 12 | + | 10 | + | 9 | + | 8 | + | 7 | – | – | – | – | – | – |
|   | FK150 | + | 21 | + | 18 | + | 18 | + | 14 | + | 11 | + | 24 | + | 17 | + | 8 | – | – |
|   | FK36 | + | 22 | + | 21 | + | 22 | + | 21 | + | 12 | + | 22 | + | 7 | + | 1 | – | – |
|   | FK64 | + | 32 | + | 32 | + | 32 | + | 32 | + | 30 | – | – | – | – | – | – | – | – |
|   | FK304 | + | 13 | + | 10 | + | 9 | + | 3 | – | – | – | – | – | – | – | – | – | – |

USE OF MASSOIALACTONE FOR INHIBITION OF FUNGAL GROWTH

RELATED APPLICATIONS

This application is a continuation-in-part of U.S. application Ser. No. 08/781,145, filed Jan. 10, 1997 now abandoned, which is a continuation of U.S. patent application Ser. No. 08/385,041, filed Feb. 7, 1995, now abandoned.

TECHNICAL FIELD

The present invention is directed to the control of fungal and microbial activity. The present invention will be directed primarily to the use of the compound massoialactone, alone or together with other antifungal compounds or with members of the genus Trichoderma, especially those producing at least one of 6-pentyl-α-pyrone (also known as 6-amyl-α-pyrone), delta-decanolactone, and massoialactone.

BACKGROUND ART

Synthetic fungicides are predominantly used for the control of fungi on crops. However many exhibit other toxic effects and could face future removal from the marketplace as controls and regulations governing agricultural chemicals tighten. In other instances, the public trend towards natural products may cause consumer resistance to the use of 'perceived' synthetic and non-natural substances.

Another problem of the art is the growing resistance of many targeted organisms substances to commonly used control agents. Accordingly there is a need for further alternatives to the currently used controlling agents, and ideally an alternative to existing control agents to which little resistance is exhibited by fungi and/or microbes.

Armillaria, a fungal pathogen of forest trees, was first identified 115 years ago, and is now recognised as a major problem in a variety of woody plant species world-wide. More than 500 different plant species are known to be susceptible to the organism. In undisturbed forests and native bush the organism rarely causes serious damage, but when trees are harvested, the rotting stumps and roots provide a rich source of nutrients so that the Armillaria may become destructively infective to any remaining shrubs and trees.

Armillaria can be devastating to the forest industry, and billions of dollars are lost annually due to affected timber. The worst losses follow reforestation after clearing the natural tree cover. In New Zealand first time losses from less than 5 to over 90% for *Pinus radiata*, a major timber crop for local and export markets, have been attributed to Armillaria.

Another major crop affected by Armillaria is kiwifruit, in which the orchards are generally planted on cleared lands. Armillaria was listed as a new disease for kiwifruit in New Zealand in 1955. However, the first detailed account of Armillaria infection in kiwifruit was in a US Department of Agriculture orchard in California; and it described the decline and death of the vines from 1967–1971.

Before 1980, the incidence of Armillaria in New Zealand kiwifruit was only occasional and it was considered to be a minor phytopathogen. Between 1980 and 1990 a dramatic increase occurred in the number of infected orchards, and the industry suffered as a consequence. Significant industry losses are expected if the disease continues to spread.

Both kiwifruit and *Pinus radiata* are major export crops for New Zealand and treatment of these commodities with synthetic pesticides is unacceptable to many export markets, and the public consumer. Insofar as controlling Armillaria is concerned, Leach in 1936 reported some benefit from ring-barking forest trees; however, this is not advisable in New Zealand because willow trees treated this way appear to have high incidence of Armillaria, and willow is one of the shelter trees used in kiwifruit orchards.

Other plant pathogens are also commercially damaging. For instance *Botrytis cinerea* is well known for its effects on grapes and its responsibility for afflictions such as kiwifruit storage rot, as well as grain mould of grapes and strawberries, etc. Botrytis diseases are among the most common and most widely distributed diseases of vegetables, ornamentals, fruits and glasshouse crops throughout the world. In New Zealand, *Botrytis cinerea* attacks many economically important horticultural crops such as kiwifruit, bean and strawberry, and in particular is the causal agent of two important diseases—grey mould of tomato and bunch rot of grape. In the past, control of these diseases has relied extensively on the use of benzimidazole and dicarboximide groups of fungicides. However, the development of fungicide resistance has reduced the effectiveness of these chemicals and thus alternative control measures are required.

Phytophthora also effects commercially important crops and is responsible, among other things, for crown rot of apples. Again, while commercially available chemicals have been used to address problems associated with Phytophthora, there is a need for an improved substitute for currently available agents which are generally only partially effective against this family.

Silver-leaf is another plant disease for which currently available methods are only partially effective. The four general diseases (Botrytis, Armillaria, silver-leaf and Phytophthora) are characterised in that they all affect commercially important crops, and are difficult to control using commercially available agents, which are generally chemical based fungicides.

It is an object of the present invention to address the foregoing problems or at least to provide the public with a useful choice.

Further aspects and advantages of the present invention will become apparent from the ensuing description which is given by way of example only.

DISCLOSURE OF INVENTION

The invention has various aspects. These are defined in the appended claims, to which specific reference should be made.

Broadly, the invention provides the following:

a method for the control or prevention of at least one member of a group of targeted afflictions comprising botrytis, armillaria, silver leaf, and phytophthora, said method comprising the administration of massoialactone to an afflicted site or to a site susceptible to such affliction.

a method for the control or prevention of at least one member of a group of targeted afflictions comprising botrytis, armillaria, silver leaf, and phytophthora, said method comprising the administration of at least one active member of the Trichoderma family which produces massoialactone to an afflicted site or to a site susceptible to such affliction.

a method substantially as described above which involves the administration of both:
massoialactone, and
at least one active member of the Trichoderma family which produces at least one of a group comprising 6-pentyl-α-pyrone, delta-decanolactone, and massoialactone.

a method for conferring, to plants, resistance to at least one of a group of targeted afflictions comprising botrytis, armillaria, silver leaf, and phytophthora, said method comprising the establishment of an active population of at least one member of the Trichoderma family which produces massoialactone, in either or both the plant or its root zone.

a method of treatment of plant growth media to address at least one of a group of targeted afflictions comprising botrytis, armillaria, silver leaf, and phytophthora, said method comprising the introduction into the growth media of either or both:
massoialactone, and
at least one active member of the Trichoderma family which produces massoialactone.

a composition for the control of at least one member of a group of targeted afflictions comprising botrytis, armillaria, silver leaf, and phytophthora, said composition comprising massoialactone alone or in combination with another antifungal compound selected from 6-pentyl-α-pyrone and delta-decanolactone, or in combination with at least one active member of the Trichoderma family capable of producing one or more of 6-pentyl-α-pyrone, delta decanolactone and massoialactone.

treated plant growth media comprising media capable of supporting the growth of a plant to which has been introduced either or both:
massoialactone, and
at least one active member of the Trichoderma family which produces massoialactone.

The term "targeted affliction" shall preferably refer to a member of the group comprising "Botrytis, Armillaria, silver-leaf, and Phytophthora". It should also be appreciated that, many of the compounds described herein will exhibit useful activity against other disorders and fungal afflictions and therefore use of the present invention need not be limited to the targeted afflictions. For instance, problems of other crop pathogens such as *Nectria galligena, Sclerotium rolfsii, Rhizoctonia solani, Sclerotium cepivorum, Macrophomina phaseolina, Fusarium oxysporum, Verticillium albostrum, Chondrostereum purpureum, Scletotinia sclerotiorum, Pythium ultimum* and *Corticum rolfsii* may also be addressed.

SPECIFIC ASPECTS OF THE INVENTION

A specific and highly important aspect of the invention is a fungicidal composition. This composition contains the compound massoialactone, (R)-5,6-dihydro-6-pentyl-2H-pyran-2-one. Massoialactone has the structure:

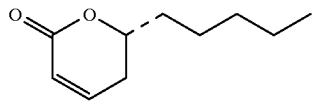

Massoialactone occurs as a racemate and as an enantiomer. For the avoidance of doubt, both forms are intended to be covered by the term "massoialactone" as used herein.

Massoialactone is commercially available as an extract of the bark of *Cryptocaria massoia* from Frutarom Ltd, Haifa, Israel. It can also be synthesized chemically, both as its racemate (3) and enantiomer (4, 5, 6, 7, 8, 9, 10 and 11).

It has also been found by the applicants to be present as a minor component of the crude extract of *Trichoderma viride*.

Prior to the applicants invention, there has been no report of massoialactone as having antifungal activity. It is this finding of the applicants that forms the basis of the specific, and claimed, aspects of this invention.

The compositions of the invention can be employed in antifungal applications containing massoialactone as the sole antifungal compound. The compositions can be formulated for application by any conventional means, including as sprays, dips, pastes or powders.

While the compositions can contain only massoialactone as the antifungal agent, compositions which include other antifungal compounds are contemplated. For example, the antifungal compounds 6-pentyl-2H-pyran-2-one and (RS)-tetrahydro-6-pentyl-2H-pyran-2-one can be employed in combination with massoialactone. These latter compounds are commonly called 6-pentyl-α-pyrone and delta-decanolactone, respectively and have the structures:

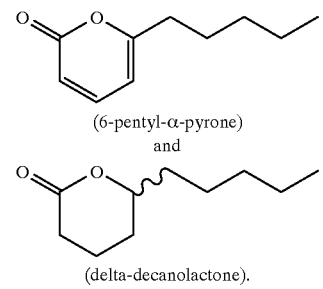

(6-pentyl-α-pyrone)
and (delta-decanolactone).

Other related lactones include:
(RS)-dihydro-5-hexyl-2H-furan-2-one,

(RS)-dihydro-5-octyl-2H-furan-2-one,

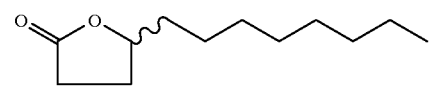

(RS)-tetrahydro-6-heptyl-2H-pyran-2-one,

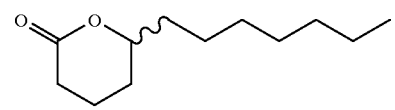

(RS)-tetrahydro-6-hexyl-2H-pyran-2-one,

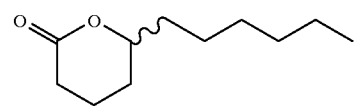

All of these compounds are available commercially from Aldrich Chemical Co., Inc., Milwaukee, Wis., United States of America.

Both 6-pentyl-α-pyrone and delta-decanolactone are produced as metabolites of a number of Trichoderma[1]. The compositions of the invention can therefore include Trichoderma organisms which produce active compounds.

BRIEF DESCRIPTION OF DRAWINGS

Further aspects of the present invention will become apparent from the ensuing description which is given by way of example only and with reference to the accompanying drawings in which.

DESCRIPTION

Figure 1:
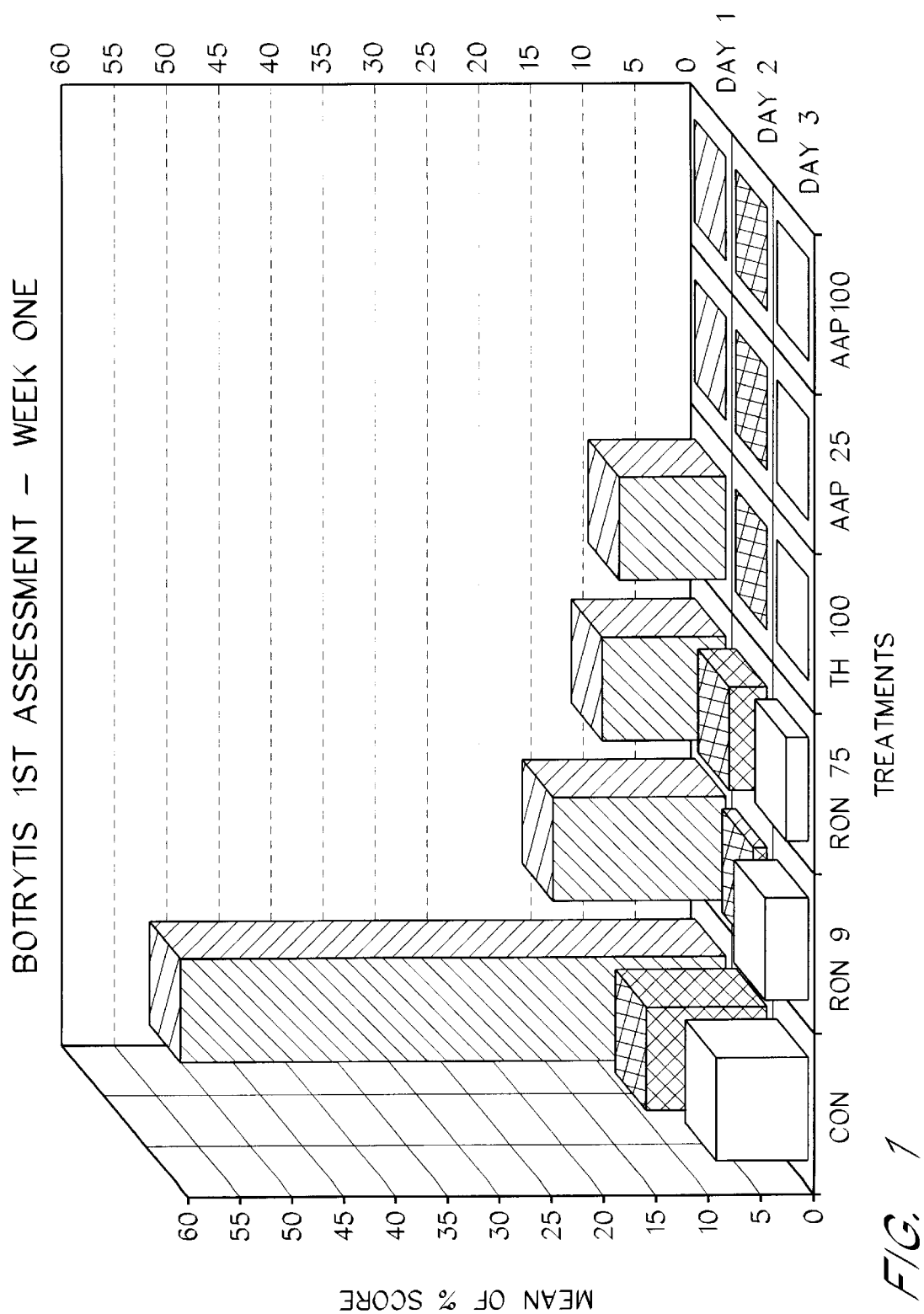
FIG. 1 is a graph—Botrytis trials first assessment—week one.
Figure 2:
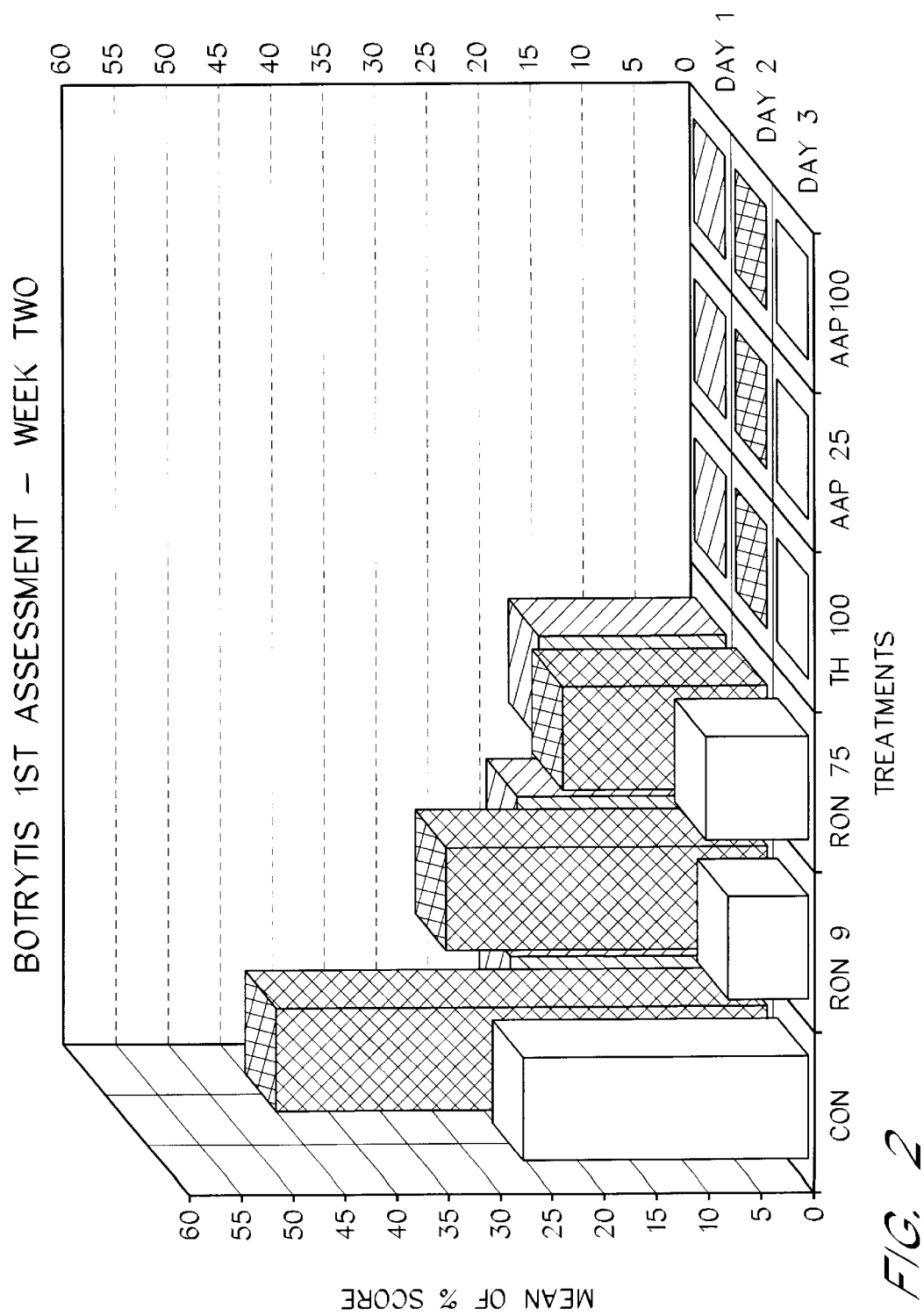
FIG. 2 is a graph—Botrytis trials first assessment—week two.
Figure 3:
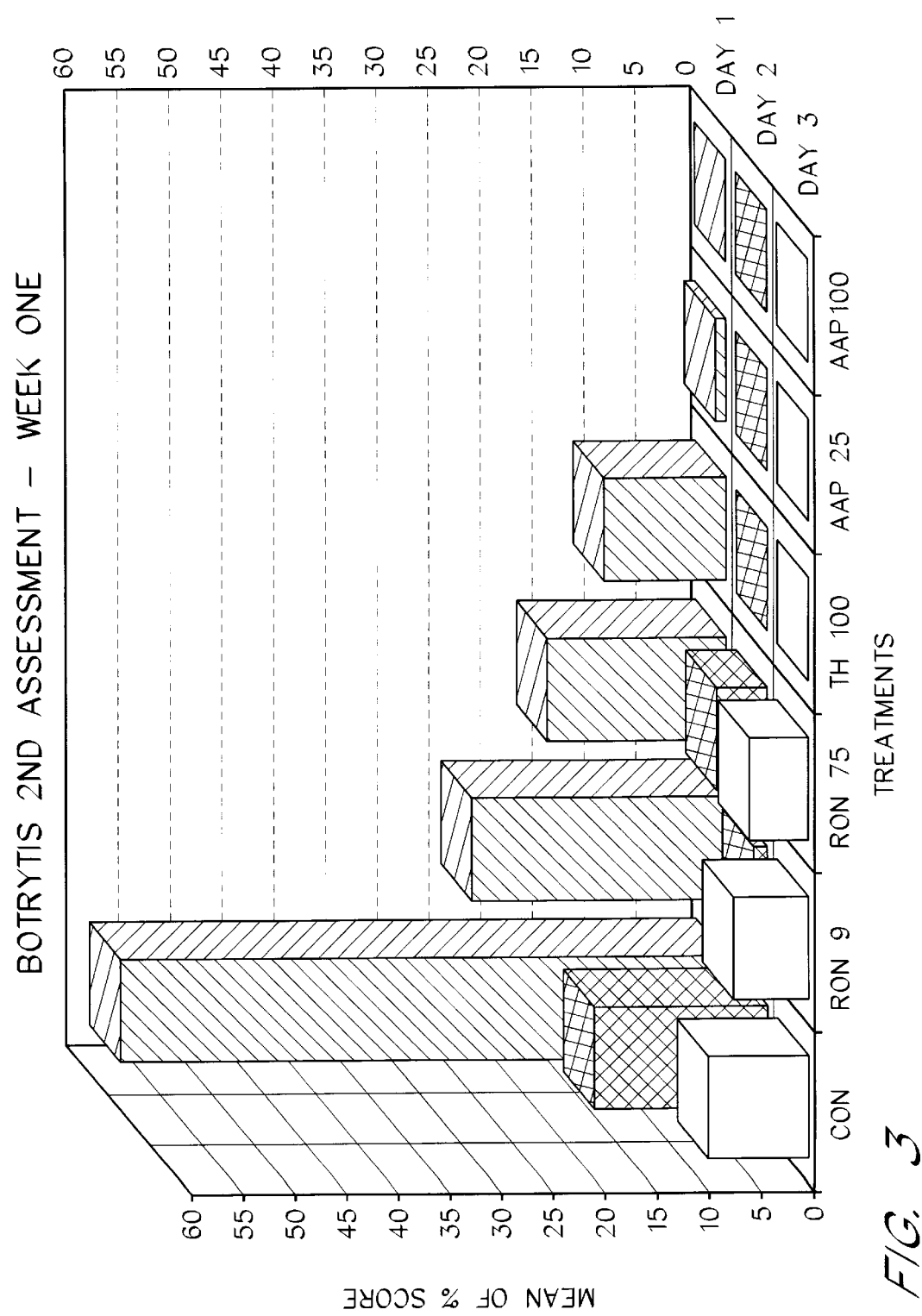
FIG. 3 is a graph—Botrytis trials second assessment—week one.
Figure 4:
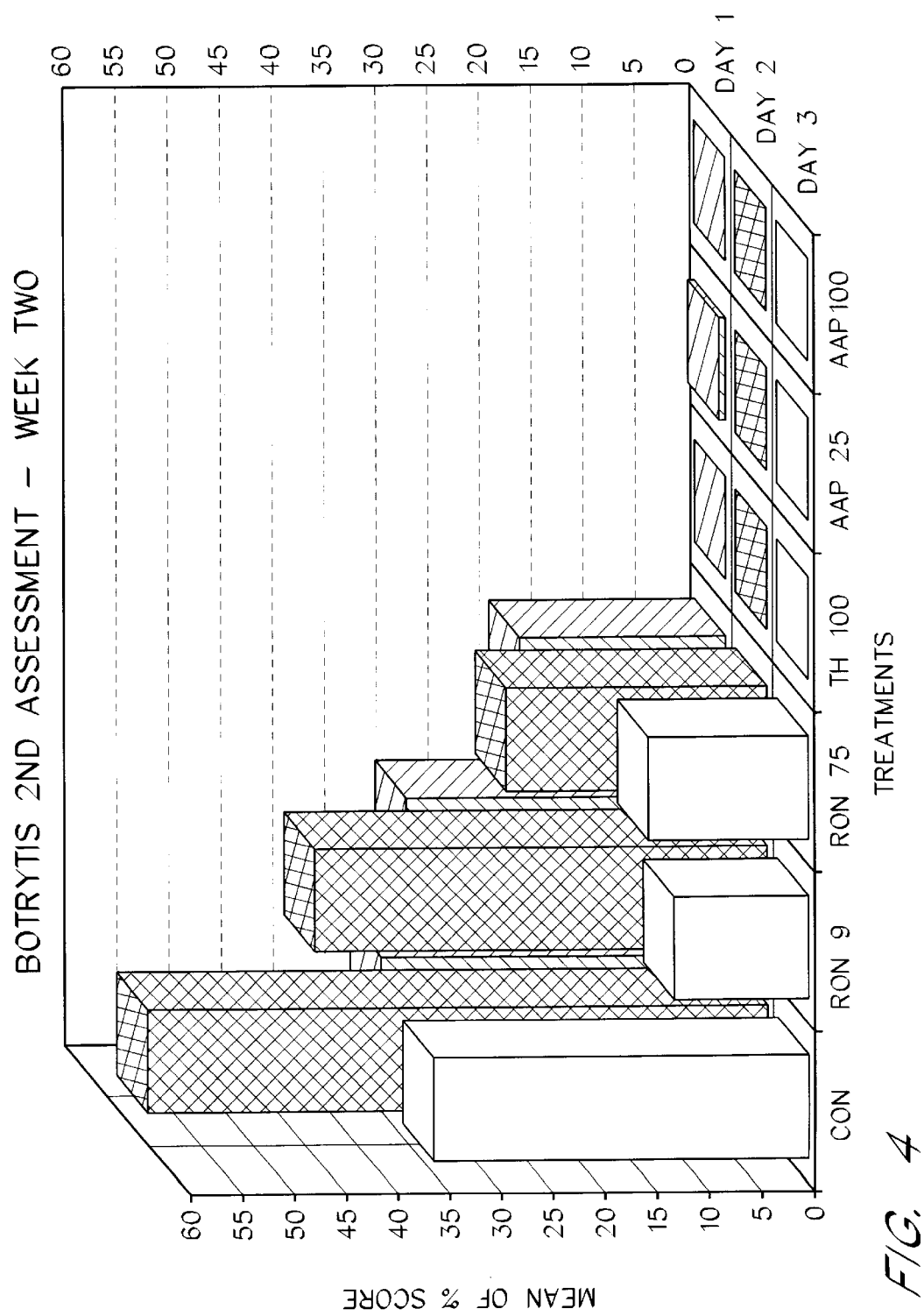
FIG. 4 is a graph—Botrytis trials second assessment—week two.
Figure 5:
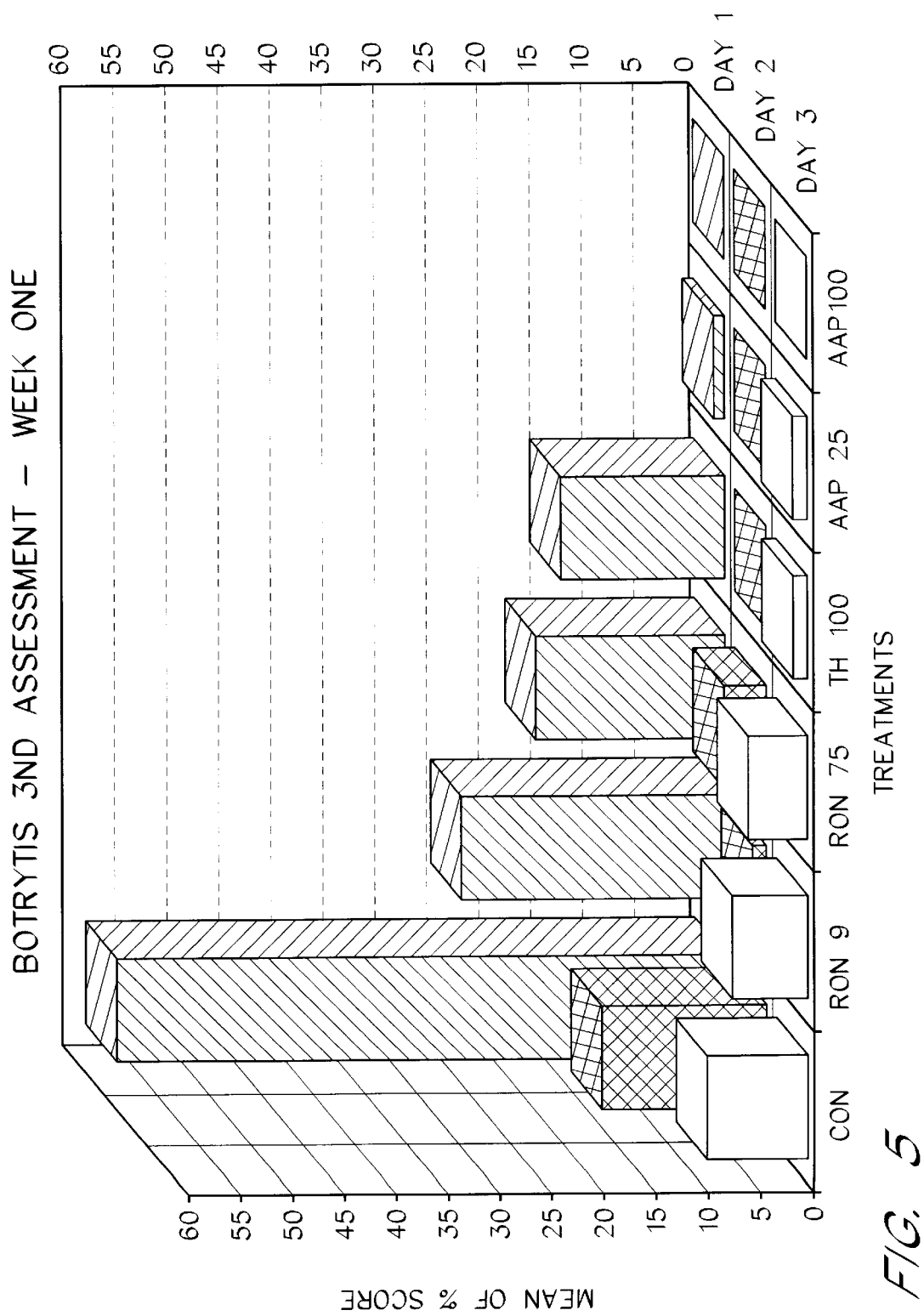
FIG. 5 is a graph—Botrytis trials third assessment—week one.
Figure 6:
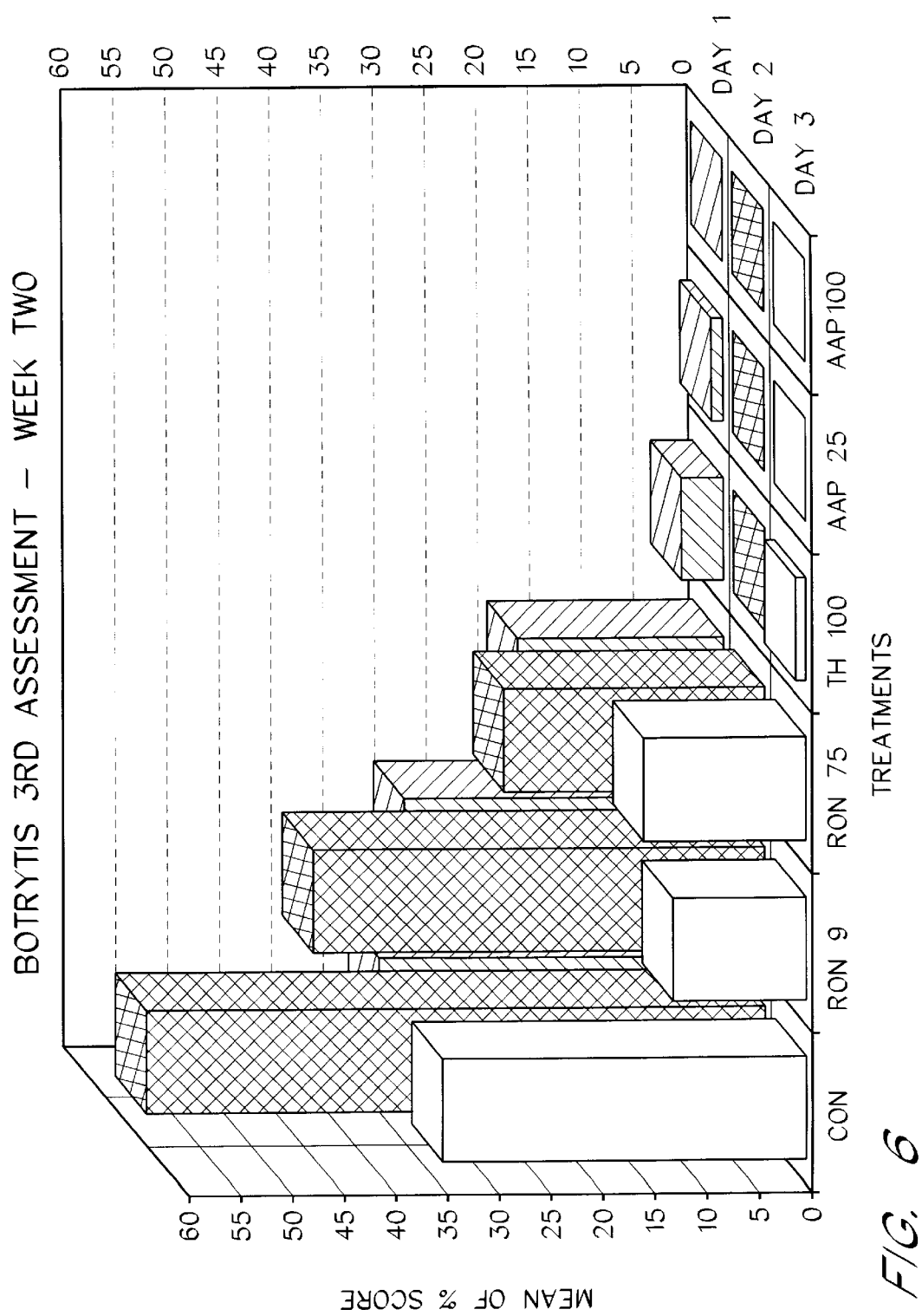
FIG. 6 is a graph—Botrytis trials first assessment—week two.
Figure 7:
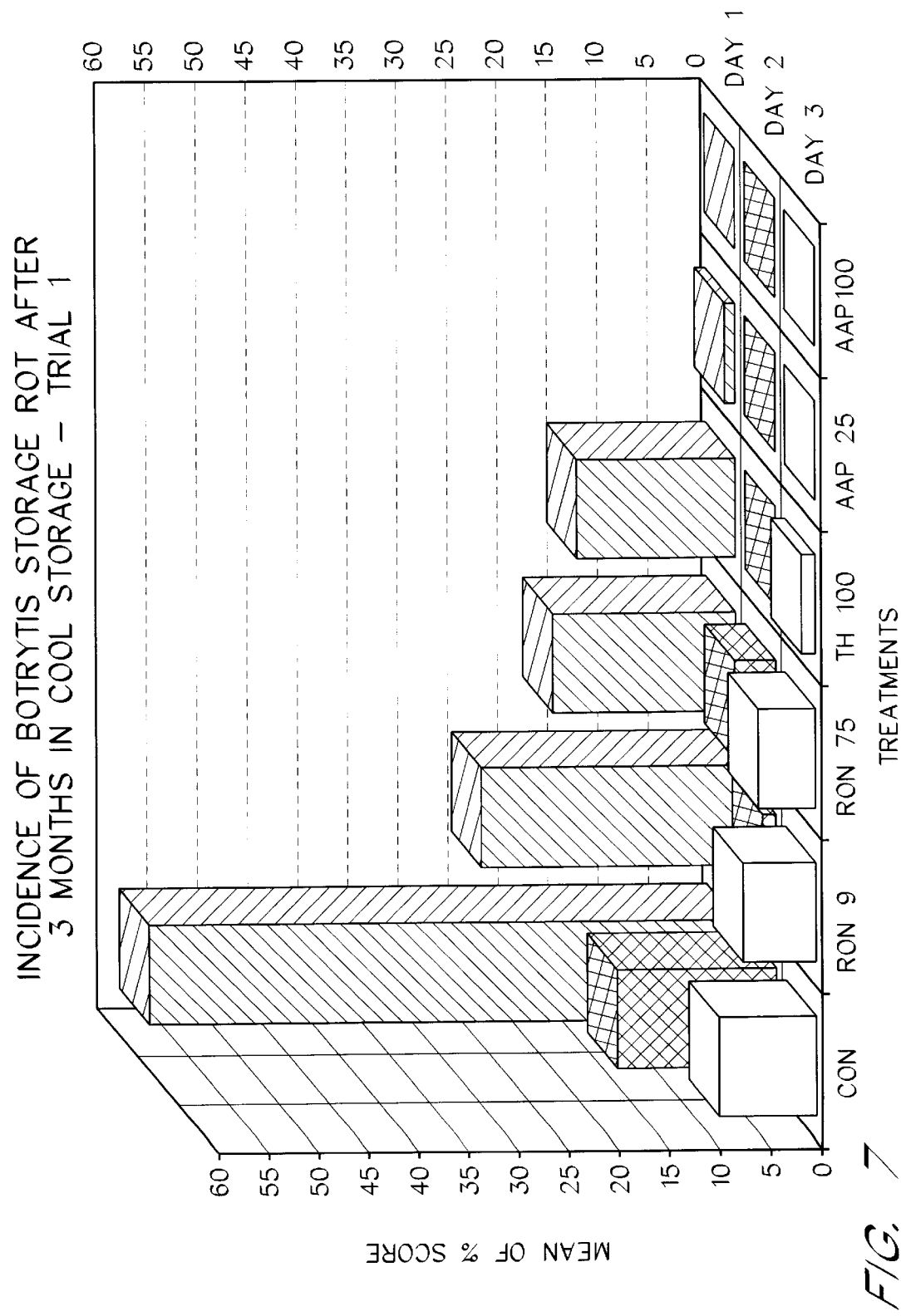
FIG. 7 incidence of Botrytis storage rot on kiwifruit after three months in cool storage—trial one FIG. 8 incidence of Botrytis storage rot on kiwifruit after three months in cool storage—trial two FIG. 9 table of the inhibition of various fungi by differing concentrations of various Trichoderma metabolites FIG. 10 Activity against Penicillium species of 500 μl each of 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). Activity was determined by the agar diffusion, multiwell assay and is recorded as the square of the diameter (mm) of the observed zone of inhibition.
Figure 8:
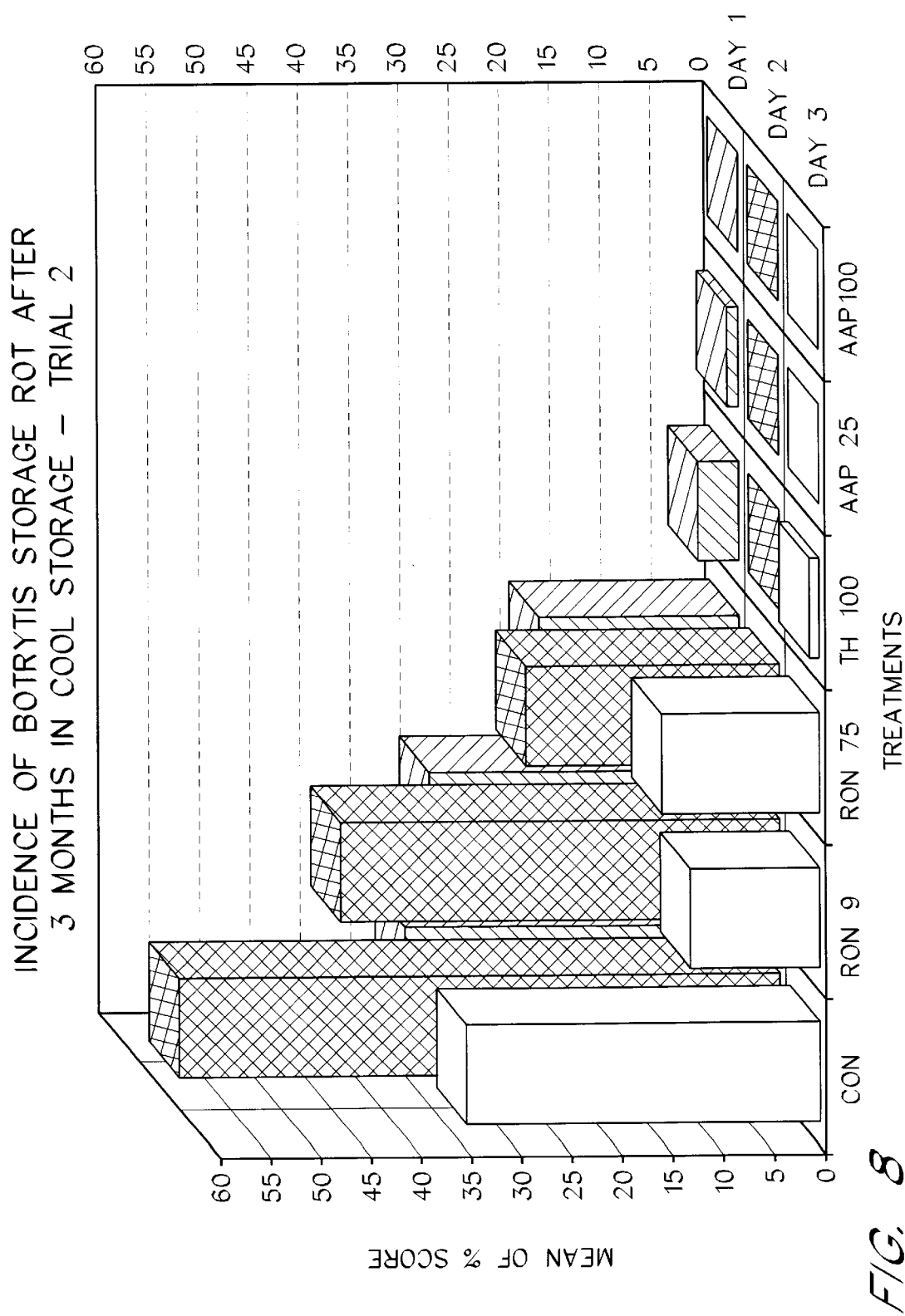

The invention is broadly as defined above, and has a focus upon massoialactone. More generally, investigative research by the applicants has established that certain Trichoderma metabolites are particularly effective against the aforesaid targeted afflictions. Trials have indicated the effectiveness of the active Trichoderma compounds against at least *Botrytis cinerea*. Further trials, and parallels in the prior art, have indicated that these results may be extrapolated to the control of other members of the group of targeted afflictions as well as to the other plant disorders and fungal afflictions listed above, in many instances.

These results indicate that the metabolite compounds are suitable secondary antifungal compounds for use in conjunction with massoialactone.

The preferred metabolite compounds comprise 6-pentyl-α-pyrone and delta-decanolactone. These may be effectively used by application of the substantially pure compound to plants and plant matter. This will depend upon the situation; in some instances injection of the composition into the sapwood may be preferred, whereas on kiwifruit picking wounds, spraying or dabbing a composition in the region of the picking wound would be preferred. Compositions may include one or more of the active Trichoderma metabolites. These may also be derived from a number of sources—for instance 6-pentyl-α-pyrone can be isolated from various Trichoderma organisms, or the synthetically produced 6-amyl-α-pyrone may also be substituted. Similarly, the other active Trichoderma metabolites may be synthetically produced or extracted from natural sources—various biosynthesis and other techniques may also be relied upon.

While the active compounds may be relied upon for control, the compound producing organisms may also be used as part of a delivery system. Introduction of Trichoderma family members to plants and crops is another alternative, as is the combination of the compound producing members in conjunction with supplemental metabolite. However, it is envisaged that often the use of 'living' control compositions will be predominantly used for plants rather than harvested crops, though exceptions may exist.

Observations by the applicants during their work include that micro-organisms grown in vitro produce the sought metabolite within a fairly narrow window of time, maybe as little as 2 to 3 days, and is then seen no more. However, in the natural state, where nutrients are abundant, they often produce secondary metabolites in a continuum which appears to last some weeks or even longer. This is the case in certain biocontrol situations.

Accordingly, where control agents comprising metabolite producing Trichoderma are applied to plants or their growth media, one is more likely to counter the extended metabolite producing window described above. In some instances it is more beneficial to include nutrients with a control composition to assist the establishment of the Trichoderma members once applied. It may be preferable to introduce, or co-apply, the nutrient at the time of application of any control agent.

Another observation is that the active organisms readily secrete the desired compounds into their immediate surroundings with relative facility; and in addition, they may deliver the materials to critical active sites and tissue conduits. Compositions containing active compound producing organisms may therefore provide an efficient delivery system for many applications. An applied compound, while sufficient for many situations such as treating fruit picking wounds, may not always provide the period of activity that a 'living' composition may. The continuing and residual activity of the active micro-organism containing embodiments will therefore find use in many situations and may provide considerable advantage over commonly used techniques and substances.

It should also be appreciated that in some cases a combination of compound and active compound producing organisms may be relied upon. A composition which immediately provides active compound perhaps in a relatively high level, to the plant or other substrate may be required in certain situations. However, there may also be a need for the continuing presence of a compound, for a period exceeding that for which an isolated compound would typically remain in place or available.

Many Trichoderma family members have been used successfully in field trials to control various crop pathogens. Examples include *Nectria galligena* in apples, *Sclerotium rolfsii* in tobacco, bean, iris; *Rhizoctonia solani* in radishes, strawberries, cucumbers, potatoes, and tomatoes; *Sclerotium cepivorum* in onions; *Macrophomina phaseolina* in maize, melons, beans, and other economically important crops; *Fusarium oxysporum* in tomatoes and Chrysanthemum and *Verticillium albo-strum* in tomatoes; *Chondrostereum purpureum* in pip fruit, stone fruits and other crops; and *Botrytis cinerea* in apples, kiwifruit.

ARMILLARIA CONTROL

Trials have indicated the more effective biological control agents for Armillaria in New Zealand to include isolates of *Trichoderma hamatum, T. harzianum, T. viride*, and other Trichoderma spp.—particularly those collected from Armillaria-infected orchards and forest sites in the Bay of Plenty. Some Trichoderma strains were growing on and consuming Armillaria mycelium and rhizomorphs. On transfer to the laboratory, in vitro tests confirmed the activity of the Trichoderma isolates against Armillaria; and as the result of many tests, superior strains were selected for field use, and different fermentation and formulation technology is presently underway.

In research the in vitro interactions between Trichoderma isolates and *Armillaria novaezelandiae* using dual plate techniques and visualisation with a light and scanning electron microscope, 11 potentially superior isolates of Trichoderma were evaluated. These included strains of *T. hamatum, T. harzianum*, and *T. viride*, and the evaluations covered two major points: the antagonistic potential against Armillaria and the compatibility of the Trichoderma isolates with each other so that they could be used in an inoculum blend. All the Trichoderma isolates antagonised Armillaria in dual culture; and the antagonism was manifest by the formation of brown residues on the surface of the Armillaria mycelium, yellowing of the Armillaria mycelium, overgrowth of the Armillaria by Trichoderma, and extensive rhizomorph initiation of the Armillaria colony. Importantly, there were differences in the antagonistic response of the accessed Trichoderma isolates to Armillaria; and in vitro cultures of *T. harzianum* were easily overgrown by *T. hamatum* and *T. viride* in paired assays.

In addition to the above observations, a temperature effect on the antagonism between Trichoderma and Armillaria was noted. The greatest antagonism was exhibited by *T. hamatum* and *T. viride* isolates between 20 and 25° C., while *T. harzianum* isolates were predominantly effective at 25° C. There was also a pH effect on the antagonism between Trichoderma and Armillaria; and this was greatest at a basic pH on malt extract agar, while on tap water agar acidic conditions were generally more favourable. Furthermore, the germination of Trichoderma spores on a low nutrient medium was enhanced under acidic conditions. There was competition for nutrients between Trichoderma and Armillaria in dual culture due to differences in the relative growth rates. Interactions between Trichoderma and Armillaria rhizomorphs indirectly indicated that hyperparasitism may be part of the control mechanism.

ACTIVE TRICHODERMA METABOLITES

Antibiotics were produced by some of the Trichoderma isolates in vitro in the New Zealand experiments, and antibiosis was detected using liquid culture and split plate techniques. However, the ability of the Trichoderma isolates to produce volatile and non-volatile antibiotics was found to differ within and between species. The culture filtrates of some of the isolates were also found to be inhibitory towards the growth of Armillaria.

Research has established that various Trichoderma species produce a number of antibiotics. The most common of these is 6-pentyl-α-pyrone (Structure 1) which has potent antifungal activity. Its coconut/celery-like odour permeates the atmosphere on isolation, and can be easily detected in Trichoderma cultures by sniffing. In vitro assays with 6-pentyl-α-pyrone has shown, for example, that a 1:40 dilution of the metabolite applied at the rate of 15 μl/4 mm disk inhibited the growth of *Aspergillus flavus*, a producer of aflatoxins.

Both *T. lignorum* and *T. viride* produce trichodermin (4β-acetoxy-12-13-epoxy trichothec-9-ene)—a natural product that has marked antibiotic effects against many fungi, including *Candida albicans*—but is relatively inactive against bacteria (Structure 2). Unfortunately, it also possesses plant growth regulatory properties and is selectively toxic to certain herbaceous plants. However, it has relatively low toxicity in mice ($LD_{50}$ 1 g/kg orally) compared to its congeners, and at one time was considered by the pharmaceutical trade to be a candidate antibiotic. A variety of other Trichoderma metabolites with biological activity have subsequently been discovered and are discussed later (vide infra).

Further Trichoderma metabolites are massoialactone (also known as massoilactone), and ±delta-decanolactone. Preliminary trials by the applicants have indicated useful activity by massoialactone against targeted afflictions. As for 6-pentyl-α-pyrone, metabolites such as massoialactone may be introduced by the establishment of Trichoderma species i.e. by the establishment of the population of a massoialactone producing species of Trichoderma It should be appreciated that the use of massoialactone, delta-decanolactone and many of the other "active Trichoderma metabolites", will be analogous to the use of 6-pentyl-α-pyrone producing Trichoderma species, for which many examples are given herein. It should also be appreciated that compositions containing a variety of "active Trichoderma metabolites" and/or active metabolite producing Trichoderma species, may all be prepared and used according to the present invention.

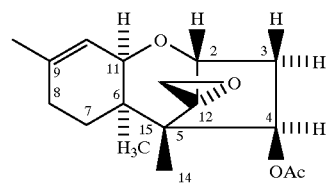

Structure of trichodermin (4β-acetoxy-12-13-epoxy trichothec-9-ene)

OBSERVED EFFECTS OF TRICHODERMA AND 6-PENTYL-α-PYRONE ON ARMILLARIA DISEASE IN *PINUS RADIATA*

Crude extracts from Trichoderma containing 6-pentyl-α-pyrone and synthetic 6-pentyl-α-pyrone (hereafter referred to as 6-amyl-α-pyrone to distinguish between the 'natural' product and the 'synthetic copy' of the natural product) were evaluated with in vitro assays against *Armillaria novae zelandiae*. Potent anti-microbial activity was seen with as little as 4 μl per disk with 6-amyl-α-pyrone, concomitantly the crude extract was active. Other micro-organisms were also strongly inhibited; and these included *Botrytis cinerea, Scletotinia sclerotiorum, Chondrostereum purpureum, Phytophthora fragariae, Pythium ultimum*, and *Corticium rolfsii*, all important phytopathogens. These results led to field trials in their respective crops of importance.

As an initial step, because Trichoderma treatments appeared to be an efficient delivery system for 6-pentyl-α-pyrone to the necessary sites, selected Trichoderma spp. isolates were tested in laboratory assays with *Pinus radiata* tissue cultured plantlets. No pathogenicity or toxicity was seen, except in very aged cultures where nutrients were exhausted. Following this, private forest trials were initiated in summertime in New Zealand, and following treatment with Trichoderma, treated trees showed less mortality and were more vigorous compared to control treatments. Far fewer treated trees (5.9%) were infected and died from Armillaria compared with controls (22%) ($P<0.019$). Treated trees were taller and had thicker trunks and wider canopy than untreated trees. Consequently, another 50 ha of *P. radiata* have been treated with Trichoderma and various combinations of Trichoderma and 6-amyl-α-pyrone to determine effects on Armillaria and enhancement of vigour.

EFFECTS OF TRICHODERMA AND 6-PENTYL-α-PYRONE/6-AMYL-α-PYRONE ON ARMILLARIA DISEASE IN KIWIFRUIT

The stumps of shelter trees that had been cut down and were possible sources of Armillaria infection have been treated with Trichoderma formulations. Soil amendments have inhibited or prevented the spread of the organism within kiwifruit orchards, and in addition soil treatment in barrier trenches between infectious Armillaria sites and kiwi plantings have been very successful. Soil drenches, too, have been effective. Injections with formulations of Trichoderma directly into the trunks of kiwi vines have shown that infected plantings may recover; and pastes made up of Trichoderma applied directly to infected areas, where as much as four fifths of the vascular cambium has been destroyed, have completely healed the vines. As the vascular cambium grew, the vines regained their lost vigour and become productive. Root treatments with Trichoderma have reduced mortality in kiwifruit vine replants at diseases sites from approximately 50% of untreated plants to 5% of treated ones. Selected Trichoderma isolates have also been evaluated for antifungal use on stored kiwifruit, and *Botrytis cinerea* was totally inhibited. Other storage organisms, including *Scletotinia sclerotiorum*, treated with species of Trichoderma and Gliocladium were successfully controlled for the first time in kiwifruit.

Armillaria infected kiwifruit vines in the Bay of Plenty were injected in February with treatments ranging from 10 to 100 μl per vine of 6-amyl-α-pyrone; 10 to 50 μl per vine of 6-pentyl-α-pyrone (the natural product is more difficult to obtain in quantity relative to the synthetic material); and 300 μl of a crude extract, known to contain 6-pentyl-α-pyrone, from a high yielding isolate of *T. hamatum*. Other infected vines were injected with a mixed strain Trichoderma formulations with proven efficacy against Armillaria. All untreated Armillaria infected vines died within 6 months. Both 6-amyl-α-pyrone and 6-pentyl-α-pyrone treatments significantly increased the survival rate (to ~50%) in infected vines. However, Trichoderma formulations were even more effective, and over 80% of the infected vines survived; while the crude extract was approximately as active as the 6-amyl-α-pyrone and 6-pentyl-α-pyrone.

OBSERVED EFFECTS OF TRICHODERMA ON THE CONTROL OF SILVER-LEAF DISEASE

Effective disease control using high 6-pentyl-α-pyrone producing strains of Trichoderma, especially *T. hamatum*, has been achieved in the North Island of New Zealand against silver-leaf disease (Chondrostereum), an organism that was controlled in vitro by Trichoderma isolates in laboratory assays. Injections with liquid formulations of Trichoderma gave rapid control of silver-leaf in *Pyrus serotinia* (nashi, Asian pear) with even severely affected trees recovering completely. Most treated trees remained disease free for two years following treatment. In addition, a pruning paste containing Trichoderma greatly reduced the spread of silver-leaf in infected nashi orchards.

Postharvest Treatments

Horticultural produce may be treated with fungicides immediately following harvest to increase shelf life. This is a critical stage because the treatment may be persistent; and depending on the nature of the fungicide, the implications as far as the consumer is concerned may be of enduring consequence. Some biocontrol alternatives to synthetic fungicides have been evaluated and the chemistry studied in some detail.

DETAILED DESCRIPTION

Trials directed to the control of *Botrytis cinerea* were conducted comparing the use of 6AAP (6-amyl-α-pyrone)) with other substances. The use of thyme oil, which has exhibited some effectiveness against certain fungi, was included in the trials. Also included was the commercial fungicide marketed under the name RONILAN®. The results of three trials, indicated as first, second and third assessments, were performed, and the results are summarised in tables 2–4 herein. FIGS. 1 through 8 are graphical representations of data accumulated during the trials.

The trials involved the mechanical application of droplets of 6-pentyl-α-pyrone (6PAP) and its synthetic equivalent 6-amyl-α-pyrone (6AAP) applied at various rates to the picking wound of kiwifruit.

Experiments have also yielded an extraction test which is suitable for determining the amount of 6-pentyl-α-pyrone in Trichoderma samples. This experimental procedure is outlined below and includes details of the typical 6-pentyl-α-pyrone contents of various Trichoderma samples. As can be appreciated, strains exhibiting higher levels of 6-pentyl-α-pyrone production will be preferred in compositions and methods according to the present invention. With reference to table 1 herein, strains exhibiting 7.5 mg/kg of 6PAP for methanol-water extractions solvent will generally be most suitable. Strains exhibiting much higher levels, typically 25 mg/kg or higher will typically be preferred in most embodiments of the present invention. However, also to be taken account of, is the period over which a particular strain will produce 6-pentyl-α-pyrone should also be taken into account.

For the purposes of the experimental procedures, the following codes are used:

| Trichoderma hamatum | OG3 | Trichoderma koningii | NZ164/US |
|---|---|---|---|
| Trichoderma hamatum | Hend | Trichoderma harizanum | US2/NZ |
| Trichoderma koningii | US3/NZ | Trichoderma hamatum | HPP1 |
| Trichoderma harizanum | D | Trichoderma viride | TV |
| Trichoderma hamatum | TBHPP7 | Trichoderma hamatum | GT4 |
| Trichoderma hamatum | KEK | | |

EXPERIMENTAL SECTION 1

Extraction Method Tests

The method PAP-1 may be summarised as follows:

1. Take a subsample of solid, typically 10 g.
2. Blend sample with a mixture of water plus methanol.
3. Filter.
4. Partition an aliquot of extract into cyclohexane after diluting with buffered saline solution.
5. Centrifuge to give phase separation.
6. Filter the supernatant organic layer through anhydrous sodium sulphate and collect.
7. Analyse by GC/FIC.

Aspects of this procedure were tested.

Extraction Solvent Tests

An initial screen of the 11 samples was done by extracting 10 g subsamples of each sample with two different solvent systems, namely; water (17 ml) plus methanol (50 ml) as for PAP-1, and 80:5:15 acetonitrile-methanol-water (50 ml). After blending, each mixture was filtered under vacuum.

It was noted that while the acetonitrile-methanol-water extractant gave mixtures which clarified rapidly on standing and filtered rapidly, the water-methanol extract mixtures did not readily clarify, were slow to filter (typically 20–30 min) and yielded cloudy filtrates. The use of a filter aid (celite) allowed these water-methanol extracts to be filtered in 1–2 min.

Partition Solvent Tests

Three alternative partition solvents, namely; cyclohexane, ethyl acetate and toluene, were tested using the sample water-methanol extracts.

Extraction Solvent v/s Partition Diluent Test

Some preliminary tests with water as the partition diluent instead of buffered saline solution showed that phase separation was often difficult or unobtainable with the acetonitrile-methanol-water extracts. The two *T. koningii* extracts produced gels which were not broken by centrifugation.

A detailed investigation into the affect of extraction solvents and saline concentration on the method and 6PAP analytical results was carried out using subsamples of the *T. koningii* culture NZ164/US. The solvents tested were different mixtures of methanol, water and acetonitrile, and the saline concentrations used were 10%, 5% and 2.5%. Each test was done in duplicate.

Reproducibility Test With New Extractant Solvent and Method

During the course of these studies a new extractant solvent, 85:15 methanol-water, was developed to replace the mixture recommended in PAP-1. The extract mixture was no longer filtered, but was allowed to clarify while standing. The partition step was as described in PAP-1, and after separation of the phases, the cyclohexane layer was dried and analysed as in PAP-1.

The reproducibility of this new method was tested using samples TBHPP7 and NZ164/US. Five replicate subsamples of each were extracted, and each extract solution worked-up and analysed in duplicate.

Fractionation of Extract on Silica

A 20 Ml sample from extraction of NZ164/US with 85:15 methanol-water was partitioned into cyclohexane according to the method (see 4.1). The total cyclohexane fraction was collected, evaporated and weighed, than re-dissolved in cyclohexane (4 ml) and applied to a column of dry silica (Dabisil) (2 g in a 8 mm I.D. column). A further 6 ml of cyclohexane was passed through the column and the eluate collected as F1. Six further fractions (F2–F7) were collected by eluting the column with 50 ml of each 10:90, 20:80, 50:50, 75:25, ethyl acetate-cyclohexane, ethyl acetate, and 90:10 ethyl acetate-methanol. All fractions were evaporated and the residues weighed before re-dissolving in 2 ml of cyclohexane for analysis.

RESULTS

Extraction Solvent Test

Initial Test

Results of the comparison of two extraction solvent systems is shown in Table 1. The estimated values for 6PAP concentrations in the samples were similar for the two systems, although higher values were obtained using the methanol-water extraction system described by Klaffenbach (PAP-1).

It was noted that while the acetonitrile-based solvent system gave extracts which clarified rapidly and did not need filtering, there were problems at the partition step. For some samples an emulsion formed which was difficult to break even with centrifugation, and this may have contributed to low estimations for 6PAP. The methanol-based system, on the other hand was slow to clarify and difficult to filter without a filter aid.

TABLE 1

Analysis of 11 Trichoderma culture samples for 6PAP after extraction with two solvent systems.

| | 6PAP (mg/kg) with extraction solvent | |
|---|---|---|
| Sample | methanol-water (50 + 17) | acetonitrile-methanol-water (80:5:15) |
| OG3 | 7.5 | 7.3 |
| Hend | <5 | n.d. |
| US3/NZ | <5 | n.d. |
| D | <5 | n.d. |
| TBHPP7 | 69.0 | 61.4 |
| KEK | <5 | n.d. |
| NZ164/US | 193.1 | 142.5 |
| US2/NZ | <5 | n.d. |
| HPP1 | 86.9 | 49.1 |
| TV | <5 | 2.6 |
| GT4 | <5 | n.d. |
| control | <5 | n.d. | n.d. is not detected at a limit of about 1 mg/kg

Partition Solvent Tests

Results with ethyl-acetate and toluene were similar to those with cyclohexane. Cyclohexane remained the solvent of choice.

Test of Alternative Extraction Solvents and Partition Diluents

The initial tests (3.1.1) had shown practical problems with both solvent systems tested, especially when applied to cultures of *T. koningii* such as NZ164/US. A further series of tests were conducted to establish a better extraction/partition system. The results are shown in Table 2.

Points to note are:

a) Clarification rate of extracts was 5>>4>3>2>1.

b) The use of acetonitrile at levels of 50% and higher caused problems with the saline partition, often giving three phases instead of two. For 50% acetonitrile this occurred with the 10% saline, but with 84% acetonitrile it occurred with the 10 and 5% saline solutions.

c) When the extraction solvent contained acetonitrile, the 6PAP concentration obtained increased with lower saline strength.

d) The 85:15 methanol-water extractant gave the most consistent set of 6PAP values.

As a result of these tests, the extraction solvent of 85:15 methanol-water was used for the reproducibility test.

TABLE 2

Analysis of 6PAP in NZ164/US culture using different extraction solvent-partition diluent combinations.

| Extraction solvent methanol-water-acetonitrile | Replicate | 6PAP (mg/kg) with saline concentrations | | |
|---|---|---|---|---|
| | | 10% saline | 5% saline | 2.5% saline |
| 65:25:10 | A | 190 | 235 | 250 |
| | B | 195 | 225 | 243 |
| 50:25:25 | A | 183 | 175 | 215 |
| | B | 205 | 225 | 225 |
| 25:25:50 | A | 190 | 255 | 260 |
| | B | 203 | 250 | 250 |
| 85:15:0 | A | 215 | 228 | 230 |
| | B | 258 | 258 | 250 |
| 0:15:85 | A | 23 | 58 | 193 |
| | B | 25 | 68 | 223 |

Reproducibility of Analytical Method For 6PAP

Five replicate subsamples of each of two samples were extracted with 85:15 methanol-water and analysed for 6PAP concentration in duplicate. The results are presented in Table 3, and show that the method gave good reproducibility.

TABLE 3

Reproducibility test.

| | 6PAP (mg/kg) | | | |
|---|---|---|---|---|
| | TBHPP7 | | NZ164/US | |
| Extract No | a | b | a | b |
| 1 | 61 | 73 | 212 | 204 |
| 2 | 74 | 74 | 203 | 214 |
| 3 | 89 | 86 | 202 | 198 |
| 4 | 94 | 89 | 208 | 202 |
| 5 | 81 | 86 | 206 | 204 |
| range | 61–94 | | 198–214 | |
| mean | 80.7 | | 205.3 | |
| % variance | 12.4 | | 2.4 | |

Silica Fractionation

A 20ml aliquot of extract from NZ164/US (Table 3, extract 3) was used for this experiment. Based on the results in 3.1.4, this should yield 0.8 mg of 6PAP. The total weight of extract residue partitioned into cyclohexane was 17.5 mg. After silica fractionation the total weight recovered was 13.8 mg, which was found mainly in F2 (39%), F3 (29%), F4 (7%) and F7 (14%). The total 6PAP recovered was 0.54 mg, which was found in F2 (87%) and F3 (13%). All other GC/FID peaks observed in the original extract were also eluted in F2 and F3.

RECOMMENDED METHOD FOR 6PAP ANALYSIS

Extraction and Workshop a) The sample (10 g) is blended with 85:15 methanol-water (50 ml) at high speed for 2 min, and the mixture decanted into a boiling tube.

b) The sample is allowed to stand for 1 hr or until there is a clear supernatant.

c) An aliquot (4 ml) of extract solution is added to 10% buffered saline solution (10 ml), then cyclohexane (2 ml) added, and the mixture shaken and allowed to settle.

d) A portion of the cyclohexane layer is filtered through anhydrous sodium sulphate and then analysed by GC/FID.

e) When analysing for 6PAP along use programme A below; when screening for other peaks use programme B.

GC Conditions

Column: 25 m HP-5, 0.2 mm i.d., 0.33 $\mu$m film

Detector: FID at 280° C.

Injector: 280° C., split 1:20, 1 $\mu$l injection

Programme:

A: 160° C. for 5 min, then to 230° C. at 30° C./min, hold 10 min, reset. Retention time for 6PAP is 3–4 min.

B: 120° C. for 12 min, then to 230° C. at 30° C./min, hold 10 min, reset. Retention time for 6PAP is 11–12 min.

TABLE 4

Initial Accessment Summary 14.6.93
1993 Botrytis Trials

| | Percentage Botrytis | | | | | |
|---|---|---|---|---|---|---|
| | Trial 4–6 May | | | Duplicate Trial 11–13 May | | |
| Treatments | Rep 1 | Rep 2 | Rep 3 | Rep 4 | Rep 5 | Rep 6 |
| Day 1 | | | | | | |
| 1. Ronilan 75 $\mu$g AI | 12 | 12 | 12 | 12 | 28 | 16 |
| 2. Ronilan 9 $\mu$g AI | 28 | 25 | 24 | 8 | 32 | 20 |
| 3. | | | | | | |
| 4. | | | | | | |
| 5. 6 AAP 100% | 0 | 0 | 0 | 0 | 0 | 0 |
| 6. 6 AAP diluted to 25% with H$_2$O | 0 | 0 | 0 | 0 | 0 | 0 |
| 7. Thyme 100% | 12 | 8 | 12 | 0 | 0 | 0 |
| 8. | | | | | | |
| 9. Control - untreated | 60 | 48 | 52 | 20 | 24 | 20 |
| Day 2 | | | | | | |
| 10. Ronilan 75 $\mu$g AI | 0 | 0 | 12 | 8 | 12 | 40 |
| 11. Ronilan 9 $\mu$g AI | 0 | 4 | 0 | 44 | 20 | 28 |
| 12. | | | | | | |
| 13. | | | | | | |
| 14. 6 AAP 100% | 0 | 0 | 0 | 0 | 0 | 0 |
| 15. 6 AAP diluted to 25% with H$_2$O | 0 | 0 | 0 | 0 | 0 | 0 |
| 16. Thyme 100% | 0 | 0 | 0 | 0 | 0 | 0 |
| 17. | | | | | | |
| 18. Control - untreated | 20 | 4 | 12 | 48 | 44 | 52 |
| Day 3 | | | | | | |
| 19. Ronilan 75 $\mu$g AI | 0 | 0 | 8 | 0 | 12 | 16 |
| 20. Ronilan 9 $\mu$g AI | 4 | 4 | 8 | 4 | 12 | 8 |
| 21. | | | | | | |
| 22. | | | | | | |
| 23. 6 AAP 100% | 0 | 0 | 0 | 0 | 0 | 0 |
| 74. 6 AAP diluted to 25% with H$_2$O | 0 | 0 | 0 | 0 | 0 | 0 |
| 25. Thyme 100% | 0 | 0 | 0 | 0 | 0 | 0 |
| 26. | | | | | | |
| 27. Control - untreated | 4 | 16 | 8 | 24 | 16 | 44 |

TABLE 5

2nd Accessment Summary 14.7.93
1993 Botrytis Trials
(Cumulative Results)

| | Percentage Botrytis | | | | | |
|---|---|---|---|---|---|---|
| | Trial 4–6 May | | | Duplicate Trial 11–13 May | | |
| Treatments | Rep 1 | Rep 2 | Rep 3 | Rep 4 | Rep 5 | Rep 6 |
| Day 1 | | | | | | |
| 1. Ronilan 75 µg AI | 12 | 12 | 28 | 12 | 28 | 20 |
| 2. Ronilan 9 µg AI | 28 | 23 | 24 | 8 | 60 | 24 |
| 3. | | | | | | |
| 4. | | | | | | |
| 5. 6 AAP 100% | 0 | 0 | 0 | 0 | 0 | 0 |
| 6. 6 AAP diluted to 25% with H$_2$O | 4 | 0 | 0 | 4 | 0 | 0 |
| 7. Thyme 100% | 16 | 8 | 12 | 0 | 0 | 0 |
| 8. | | | | | | |
| 9. Control - untreated | 64 | 60 | 52 | 32 | 36 | 32 |
| Day 2 | | | | | | |
| 10. Ronilan 75 µg AI | 0 | 0 | 12 | 16 | 12 | 48 |
| 11. Ronilan 9 µg AI | 0 | 4 | 4 | 56 | 40 | 32 |
| 12. | | | | | | |
| 13. | | | | | | |
| 14. 6 AAP 100% | 0 | 0 | 0 | 0 | 0 | 0 |
| 15. 6 AAP diluted to 25% with H$_2$O | 0 | 0 | 0 | 0 | 0 | 0 |
| 16. Thyme 100% | 0 | 0 | 0 | 0 | 0 | 0 |
| 17. | | | | | | |
| 18. Control - untreated | 24 | 8 | 16 | 56 | 68 | 60 |
| Day 3 | | | | | | |
| 19. Ronilan 75 µg AI | 4 | 0 | 12 | 8 | 16 | 20 |
| 20. Ronilan 9 µg AI | 4 | 4 | 12 | 8 | 12 | 24 |
| 21. | | | | | | |
| 22. | | | | | | |
| 23. 6 AAP 100% | 0 | 0 | 0 | 0 | 0 | 0 |
| 24. 6 AAP diluted to 25% with H$_2$O | 0 | 0 | 0 | 0 | 0 | 0 |
| 25. Thyme 100% | 0 | 0 | 0 | 0 | 0 | 0 |
| 26. | | | | | | |
| 27. Control - untreated | 4 | 20 | 8 | 28 | 24 | 56 |

TABLE 6

Final Assessment Summary 18.8.93
1993 Botrytis Trials
(Cumulative Results)

| | Percentage Botrytis | | | | | |
|---|---|---|---|---|---|---|
| | Trial 4–6 May | | | Duplicate Trial 11–13 May | | |
| Treatments | Rep 1 | Rep 2 | Rep 3 | Rep 4 | Rep 5 | Rep 6 |
| Day 1 | | | | | | |
| 1. Ronilan 75 µg AI | 12 | 16 | 28 | 12 | 28 | 20 |
| 2. Ronilan 9 µg AI | 28 | 23 | 28 | 8 | 60 | 24 |
| 3. | | | | | | |
| 4. | | | | | | |
| 5. 6 AAP 100% | 0 | 0 | 0 | 0 | 0 | 0 |
| 6. 6 AAP diluted to 25% with H$_2$O | 4 | 0 | 0 | 4 | 0 | 0 |
| 7. Thyme 100% | 16 | 8 | 24 | 4 | 4 | 4 |
| 8. | | | | | | |
| 9. Control - untreated | 64 | 60 | 52 | 32 | 36 | 32 |
| Day 2 | | | | | | |
| 10. Ronilan 75 µg AI | 0 | 0 | 12 | 16 | 12 | 48 |
| 11. Ronilan 9 µg AI | 0 | 4 | 4 | 60 | 40 | 32 |
| 12. | | | | | | |
| 13. | | | | | | |
| 14. 6 AAP 100% | 0 | 0 | 0 | 0 | 0 | 0 |
| 15. 6 AAP diluted to 25% with H$_2$O | 0 | 0 | 0 | 0 | 0 | 0 |
| 16. Thyme 100% | 0 | 0 | 0 | 0 | 0 | 0 |
| 17. | | | | | | |
| 18. Control - untreated | 24 | 8 | 16 | 56 | 68 | 60 |
| Day 3 | | | | | | |
| 19. Ronilan 75 µg AI | 4 | 0 | 12 | 12 | 16 | 20 |
| 20. Ronilan 9 µg AI | 4 | 4 | 12 | 8 | 12 | 24 |
| 21. | | | | | | |
| 22. | | | | | | |
| 23. 6 AAP 100% | 0 | 0 | 0 | 0 | 0 | 0 |
| 24. 6 AAP diluted to 25% with H$_2$O | 0 | 0 | 0 | 0 | 0 | 0 |
| 25. Thyme 100% | 0 | 4 | 0 | 0 | 0 | 4 |
| 26. | | | | | | |
| 27. Control - untreated | 4 | 20 | 8 | 28 | 24 | 56 |

TABLE 7

Final Assessment Summary 18.8.93
1993 Botrytis Trials
(Cumulative Results)

| | Percentage Botrytis | | | | | |
|---|---|---|---|---|---|---|
| | Trial 4–6 May | | | Duplicate Trial 11–13 May | | |
| Treatments | Rep 1 | Rep 2 | Rep 3 | Rep 4 | Rep 5 | Rep 6 |
| Day 1 | | | | | | |
| 1. Ronilan 75 µg AI | 12 | 16 | 28 | 12 | 28 | 20 |
| 2. Ronilan 9 µg AI | 28 | 23 | 28 | 8 | 60 | 24 |
| 4. | | | | | | |
| 5. 6 AAP 100% | 0 | 0 | 0 | 0 | 0 | 0 |
| 6. 6 AAP diluted to 25% with H$_2$O | 4 | 0 | 0 | 4 | 0 | 0 |
| 7. Thyme 100% | 16 | 8 | 24 | 4 | 4 | 4 |
| 8. | | | | | | |
| 9. Control - untreated | 64 | 60 | 52 | 32 | 36 | 32 |
| Day 2 | | | | | | |
| 10. Ronilan 75 µg AI | 0 | 0 | 12 | 16 | 12 | 48 |
| 11. Ronilan 9 µg AI | 0 | 4 | 4 | 60 | 40 | 32 |
| 12. | | | | | | |
| 13. | | | | | | |
| 14. 6 AAP 100% | 0 | 0 | 0 | 0 | 0 | 0 |
| 15. 6 AAP diluted to 25% with H$_2$O | 0 | 0 | 0 | 0 | 0 | 0 |
| 16. Thyme 100% | 0 | 0 | 0 | 0 | 0 | 0 |
| 17. | | | | | | |
| 18. Control-untreated | 24 | 8 | 16 | 56 | 68 | 60 |
| Day 3 | | | | | | |
| 19. Ronilan 75 µg AI | 4 | 0 | 12 | 12 | 16 | 20 |
| 20. Ronilan 9 µg AI | 4 | 4 | 12 | 8 | 12 | 24 |
| 21. | | | | | | |
| 22. | | | | | | |
| 23. 6 AAP 100% | 0 | 0 | 0 | 0 | 0 | 0 |

TABLE 7-continued

Final Assessment Summary 18.8.93
1993 Botrytis Trials
(Cumulative Results)

| | Percentage Botrytis | | | | | |
|---|---|---|---|---|---|---|
| | Trial 4–6 May | | | Duplicate Trial 11–13 May | | |
| Treatments | Rep 1 | Rep 2 | Rep 3 | Rep 4 | Rep 5 | Rep 6 |
| 24. 6 AAP diluted to 25% with H$_2$O | 0 | 0 | 0 | 0 | 0 | 0 |
| 25. Thyme 100% | 0 | 4 | 0 | 0 | 0 | 4 |
| 26. | | | | | | |
| 27. Control - untreated | 4 | 20 | 8 | 28 | 24 | 56 |

The present invention can be put into practice in many ways. In some embodiments the invention may be used as a curative measure to address plants already infected by the targeted afflictions. In other cases, the invention may find a preventative role, acting to prevent the targeted afflictions establishing themselves in various plants and produce. The role in which the invention is to be used will have some bearing, in most instances, on the particular embodiment which may be relied upon by the user.

For instance, in curative type roles, fungicidal compositions may be sufficient in their own right to address targeted afflictions present in plants. However, in most cases such preparations are relatively short lived in their effect (e.g. they may be washed from foliage), unless means is provided to maintain the presence of sufficient levels of the active compound in the required portion of the plant. The use of non-aqueous constituents in compositions, as well as many other known means of retarding the dilution or removal of active constituents, may be relied upon.

As another option, a composition may seek to establish a population of a Trichoderma compound producing organism though in a curative role. Supplementing such compositions with added active metabolite (regardless of its source) is yet a further option. This ensures that active components are immediately available to the plants. A relatively high initial concentration of 6-pentyl-α-pyrone and/or other metabolites may be more effective in reducing the level of the organisms responsible for the plant affliction to manageable levels, which can thereafter be controlled by the establishment of a population of "active Trichoderma metabolite" producing organisms.

Where the present invention is used in a preventative role, the higher initial levels of active metabolites such as 6-pentyl-α-pyrone may not be required and thus the establishment of a population of active metabolite producing organisms may be sufficient to provide long term and lasting control of targeted afflictions. As can be appreciated, according to the needs of the user, the use of "active Trichoderma metabolite" producing organisms, and combinations of the two may be relied upon.

In some embodiments of the present invention, compositions based on the foregoing description may be introduced directly into plant tissue, and in woody plants this is typically the sapwood. For seedlings or where direct introduction into plant tissue is not practical, introduction into the root zone may be satisfactory. In many instances the establishment of an effective "active Trichoderma metabolite" producing population in the root zone of a plant may be readily established. This may be accomplished, by way of example only, by the introduction of suitable organisms into soil or growing media, the treatment of potting and seedling mixes, the coating of seeds, and the roots of seedlings in treated compositions etc. Many other methods, including the application of various compositions to external surfaces of the plant may be relied upon. Some various examples follow:

EXAMPLE 1

A composition including a live population of a Trichoderma species producing an "active Trichoderma metabolite" is introduced into the sapwood, or equivalent, of a plant. Typically this is by injection though introduction into an incision is another of many possible techniques. The quantity and nature of the introduction should be such that growing population of the Trichoderma species is established within the plant.

Compositions may comprise more than one Trichoderma species and the various Trichoderma species need not produce the same metabolites nor the same metabolites in the same proportions.

As a variation, non-Trichoderma species which are capable of producing "active Trichoderma metabolites", and which do not show any pathogenic tendencies towards the plant, may be included.

EXAMPLE 2

To the composition of example 1, is included at least one "active Trichoderma metabolite". Particular metabolites of interest include 6-pentyl-α-pyrone, massoialactone, and delta-decanolactone.

EXAMPLE 3

A composition comprising one or more "active Trichoderma metabolites" is used for this example. Typically such a composition will differ from the composition of example 2 in that there is substantially little, or no, living Trichoderma material in the composition. Generally these compositions are used primarily in a curative or controlling role rather than a preventative or long term control role. Methods of use may be as described for examples 1 and 2 or the other examples herein.

EXAMPLE 4

The compositions of examples 1, 2 or 3 are applied to the foliage and/or reproductive material of a plant. In this case reproductive material will often include the fruit or seed bearing portions. In an artificial environment or where there is human intervention, reproductive material shall also include cuttings, and various portions used for propagation. Typically application is by spray, dipping, dusting or some other coating process.

EXAMPLE 5

This method generally uses the compositions of examples 1 and 2 though the composition of example 3 may be used where long term or continuing effects are not desirable or necessary. According to this method compositions are introduced into the immediate interactive environment of the targeted plants, which generally means the soil and root zone.

Methods of application include drenching of plant growth media, which will be suitable for established plants. Mulches and fertiliser compositions containing the compositions of the present invention may also be relied upon to introduce the active metabolites and/or Trichoderma species into the plants' environment.

The preparation of potting mixes and other growth media which have been fumigated and/or inoculated with the various compositions of the present invention are other means to introduce the preferred agents into the plants' environment. It is also envisaged that where the population of Trichoderma species is established in the root zone of seedlings, the seedlings when transplanted will carry along sufficient living organisms to establish a new population in the new site.

For instance, for *Pinus radiata* seedlings, their propagation in growth media containing a Trichoderma population would be relied upon. When the seedlings were transplanted to their final growth site, a living Trichodenna population would be carried over with it. Depositing some of the seedlings' growth media when planting seedlings in their new site would assist the establishment of the new Trichoderma population. The further application of a Trichoderma containing composition immediately prior to re-planting could be used to further enhance the effects. Applying an active metabolite containing composition may also be useful.

EXAMPLE 6

The composition substantially as described in examples 1 through 3 is used to treat wounds on plants. Typically such compositions will be fluid or paste-like so that they may be applied to wounds such as caused through pruning. Incorporation of non-aqueous or hydrophobic components may also be relied upon to resist washing of the active metabolites and/or living organisms from the region of application.

Compositions for wound application may also provide a suitable growth media for establishing a population of a Trichoderma species. Nutrients and a suitable support (such as use of a paste which dries or sets to provide a cap or cover for the wound) are considerations which may be addressed in the various compositions.

EXAMPLE 7

A method for protecting seedlings against plant disorders comprising the introduction to the roots of the seedlings, either or both "active Trichoderma metabolites" and active metabolite producing members of the Trichoderma family. In this instance, cuttings, seedlings, etc. may be dipped in a liquid composition containing a metabolites and/or metabolite producing members. Alternatively, various compositions may be dusted or sprayed onto the roots or appropriate portions of the seedlings or cuttings etc.

EXAMPLE 8

According to another embodiment, a substantially solid pellet may be prepared which is able to slowly decay in the environment in which it is to be used. Various slow decay compositions and techniques are known and recorded in the art—these may be relied upon.

The pellets will typically contain either or both "active Trichoderma metabolites", and active metabolite producing Trichoderma organisms. Nutrients, for the plants, and/or the Trichoderma species, may be included in the pellets. Other substances, such as pesticides, fungicides, plant hormones, etc. may also be included in a pellet. It is noted that these other substances may also be included in various other embodiments of the present invention.

EXAMPLE 9

A composition comprising an "active Trichoderma metabolite" may be applied to harvested produce, typically in the region of the picking wound. While 'living' Trichoderma populations may be relied upon, these are not generally necessary—metabolites will generally remain on the produce (depending on its handling) sufficiently long to offer adequate protection.

Trials were performed by the applicant to determine the relative effectiveness of various "active Trichoderrna metabolites" in addressing *Botrytis cinerea*. The trials involved the application of 4 mg of each trial substance to the picking wound of kiwifruit. The results are summarised in the tables 8–11.

Other substances used in the trials included Ronilan™, a proprietary fungicide whose use is widespread for this type of application. Beta-ionone and calcium chloride were also included in the trials. AANB, CAH, CAL and BNB are various experimental compounds extracted from kiwifruit. 6AAP represents 6-pentyl-α-pyrone.

TABLE 8

Trial 1
Number fruit/treatment: 100
Volume treatment/application: 4 mg
Application method: hand pipetted
Harvest Date: 16/5/94 (1)

| Hrs after inoculation treatment applied | Treatment | % botrytis rots @ 9 weeks after treated |
|---|---|---|
| 4 | 1 - AANB | 33 |
|  | 2 - CaCl$_2$ (0.12%) | 44 |
|  | 3 - CaCl$_2$ (1/10) | 41 |
|  | 4 - Beta-ionone | 54 |
|  | 5 - Ronilan 75µ AI | 9 |
|  | 6 - 6AAP 100% | 0 |
|  | 7 - 6AAP 50% | 0 |
|  | 8 - 6AAP 25% | 2 |
|  | 9 - 6AAP 10% | 15 |
|  | 10 - Control untreated | 42 |
| 51 | 11 - AANB | 60 |
|  | 12 - CaCl$_2$ (0.12%) | 60 |
|  | 13 - CaCl$_2$ (1/10) | 63 |
|  | 14 - Beta-ionone | 18 |
|  | 15 - Ronilan 75µ AI | 18 |
|  | 16 - 6AAP 100% | 0 |
|  | 17 - 6AAP 50% | 0 |
|  | 18 - 6AAP 25% | 0 |
|  | 19 - 6AAP 10% | 1 |
|  | 20 - Control untreated | 74 |

TABLE 9

Harvest Date: 23/5/94 (2)

| Hrs after inoculation treatment applied | Treatment | % botrytis rots @ 8 weeks after treated |
|---|---|---|
| 4 | 1 - AANB | 27 |
|  | 2 - CaCl$_2$ (0.12%) | 29 |
|  | 3 - CaCl$_2$ (1/10) | 16 |
|  | 4 - Beta-ionone | 32 |
|  | 5 - Ronilan 75 µg AI | 1 |
|  | 6 - 6AAP 100% | 0 |
|  | 7 - 6AAP 50% | 0 |
|  | 8 - 6AAP 25% | 0 |
|  | 9 - 6AAP 10% | 3 |
|  | 10 - Control untreated | 36 |
| 51 | 11 - AANB | 38 |
|  | 12 - CaCl$_2$ (0.12%) | 35 |
|  | 13 - CaCl$_2$ (1/10) | 23 |

TABLE 9-continued

Harvest Date: 23/5/94 (2)

| Hrs after inoculation treatment applied | Treatment | % botrytis rots @ 8 weeks after treated |
|---|---|---|
| | 14 - Beta-ionone | 2 |
| | 15 - Ronilan 75 μg AI | 4 |
| | 16 - 6AAP 100% | 0 |
| | 17 - 6AAP 50% | 0 |
| | 18 - 6AAP 25% | 0 |
| | 19 - 6AAP 10% | 0 |
| | 20 - Control untreated | 30 |

TABLE 10

Harvest Date: 30/5/94 (3)

| Hrs after inoculation treatment applied | Treatment | % botrytis rots @ 7 weeks after treated |
|---|---|---|
| 4 | 1 - CAH | 40 |
| | 2 - CAL | 49 |
| | 3 - BNB | 34 |
| | 4 - delta decanolactone | 30 |
| | 5 - Ronilan 75 μg AI | 5 |
| | 6 - 6AAP 100% | 0 |
| | 7 - massoilactone | 0 |
| | 8 - 6AAP 25% | 0 |
| | 9 - 6AAP 10% | 0 |
| | 10 - Control untreated | 47 |
| 51 | 11 - CAH | 61 |
| | 12 - CAL | 47 |
| | 13 - BNB | 54 |
| | 14 - delta decanolactone | 2 |
| | 15 - Ronilan 75 μg AI | 55 |
| | 16 - 6AAP 100% | 0 |
| | 17 - massoilactone | 1 |
| | 18 - 6AAP 25% | 0 |
| | 19 - 6AAP 10% | 0 |
| | 20 - Control untreated | 78 |

TABLE 11

Number fruit/treatment 1254
Volume treatment/application: 4 mg
Application method: automated droplet

| Treatment | % botrytis rots @ 10 weeks after treated |
|---|---|
| Harvest Date: 10/5/94 (4) | |
| 1 - 6AAP 100% | 0 |
| 2 - 6AAP 10% | 0.88 |
| 3 - Control untreated | 7.42 |

| Treatment | % botrytis rots @ 8 weeks after treated |
|---|---|
| Harvest Date: 24/5/94 (5) | |
| 1 - 6AAP 100% | 0 |
| 2 - 6AAP 10% | 0 |
| 3 - Control untreated | 1.36 |

Number fruit/treatment: 1050
Volume treatment/application: 4 mg
Application method: automated droplet

| Treatment | % botrytis rots @ 10 weeks after treated | |
|---|---|---|
| | Single Layers Trays | Europacks |

TABLE 11-continued

| | | |
|---|---|---|
| Harvest Date: 10/5/94 (6) | | |
| 1 - 6AAP 100% | 0.19 | 0 |
| 2 - Control untreated | 12.4 | 6.57 |
| Harvest Date: 24/5/94 (7) | | |

| Treatment | % botrytis rots @ 8 weeks after treated | |
|---|---|---|
| | Single Layers Trays | Europacks |
| Harvest Date: 24/5/94 (7) | | |
| 1 - 6AAP 100% | 0 | 0.29 |
| 2 - Control untreated | 4.38 | 0.86 |

Treatment application method: automated droplet
Assessment time after treatment: 7–9 weeks

| Treatment | No. fruit treated | Botrytis rots No. | % |
|---|---|---|---|
| 6AAP (100%) | | | |
| contact wound | 6010 | 3 | 0.05 |
| outside wound | 698 | 2 | 0.29 |
| 6AAP (10%) | | | |
| contact wound | 2409 | 10 | 0.42 |
| outside wound | 99 | 1 | 1.01 |
| control | 6708 | 364 | 5.43 |

As can be appreciated from the data, 6-pentyl-α-pyrone is extremely effective against *Botrytis cinerea*. It is also noted that the technique of hand pipetting the selected substance onto the picking wound was not always accurate and in some cases the selected substance was delivered to a site adjacent to the picking wound rather than on it. An observation from the trial was that 6-pentyl-α-pyrone delivered next to the picking wound still provided relatively effective control against *Botrytis cinerea* in those cases.

Massoilactone, an "active Trichoderma metabolite" was also very effective though delta-decanolactone (another "active Trichoderma metabolite") was less effective. This compound appears to be more selective in those plant afflictions against which it is effective, though it still provided good results against *Botrytis cinerea* and in some cases was more effective than the commercially used fungicide, RONILAN™.

EXAMPLE 10

FIG. 9 is a table of data from petri dish trials of the effectiveness of various Trichoderma metabolites against a variety of fungi. In these trials, Treatment 1 represented 6-pentyl-α-pyrone, while Treatment 2 was a mixture of 6-pentyl-α-pyrone, massoialactone, and delta-decanolactone. Treatment 3 comprised delta-decanolactone while treatment 4 comprised.

The experimental procedure placed a portion of the treatment in the centre of the Petri dish while the figures in mm on the table represent the distance of closest approach of fungus induced to grow on the Petri dish.

The results indicate that the various Trichoderma metabolites are effective against a range of different fungi and also indicate that delta-decanolactone is more effective against some fungi than others though still remains active against all the fungi included in the trials.

In the trials, the fungi prefixed by fk are all fungi associated with sapstain, and comprise:

fk150
fk36 Ceratocystis sp.
fk64 Ceratocystis sp.
fk304

Further trials were performed using a variety of "active Trichoderma metabolites", as well as other substance, for the control of *Botrytis cinerea*. These results are listed in Tables 12 onwards and exhibits the actual activity of 6-pentyl-α-pyrone (6AAP) and. Under certain conditions, delta-decanolactone exhibited high activity, and at worst an activity comparable to other prior art treatments.

TABLE 12

6 AAP Botrytis Trial 1 - Treatment after 4 hours

| Harvest No. | Treatment | % botrytis rots @ 9 weeks after treated | % botrytis rots @ 18 weeks |
|---|---|---|---|
| 1 | 1. AANB | 33 | 33 |
| | 2. CaCl2 (0.12%) | 44 | 44 |
| | 3. CaCl2 (1/10) | 41 | 41 |
| | 4. Beta-ionone | 54 | 87 |
| | 5. Ronilan 75 u Al | 9 | 10 |
| | 6. 6 AAP 100% | 0 | 0 |
| | 7. 6 AAP 50% | 0 | 0 |
| | 8. 6 AAP 25% | 2 | 2 |
| | 9. 6 AAP 10% | 15 | 20 |
| | 10. Control untreated | 42 | 42 |
| 2 | 1. AANB | 27 | 27 |
| | 2. CaCl2 (0.12%) | 29 | 29 |
| | 3. CaCl2 (1/10) | 16 | 17 |
| | 4. Beta-ionone | 32 | 45 |
| | 5. Ronilan 75 ug Al | 1 | 2 |
| | 6. 6 AAP 100% | 0 | 0 |
| | 7. 6 AAP 50% | 0 | 0 |
| | 8. 6 AAP 25% | 0 | 0 |
| | 9. 6 AAP 10% | 3 | 6 |
| | 10. Control untreated | 36 | 40 |
| 3 | 1. CAH | 40 | 43 |
| | 2. CAL | 49 | 50 |
| | 3. BNB | 34 | 40 |
| | 4. delta decanolactone | 30 | 41 |
| | 5. Ronilan 75 ug Al | 5 | 5 |
| | 6. 6 AAP 100% | 0 | 0 |
| | 7. massoilactone | 0 | 0 |
| | 8. 6 AAP 25% | 0 | 0 |
| | 9. 6 AAP 10% | 0 | 1 |
| | 10. Control untreated | 47 | 48 |

TABLES 13–14

6AAP Botrytis Trial 2 - Automated droplet (naturally inoculated)

| Harvest No. | Treatment | % botrytis rots @ 10 weeks after treated | % botrytis rots @ 19 weeks |
|---|---|---|---|
| 1 | 1. 6AAP 100% | 0 | 0 |
| | 2. 6AAP 10% | 0.88 | 1.12 |
| | 3. Control untreated | 7.42 | 7.74 |

| Harvest No. | Treatment | % botrytis rots @ 8 weeks after treated | % botrytis rots @ 17 weeks |
|---|---|---|---|
| 2 | 1. 6AAP 100% | 0 | 0.08 |
| | 2. 6AAP 10% | 0 | 0.64 |
| | 3. Control untreated | 1.36 | 3.51 |

6AAP Botrytis Trial 3 - Automated droplet (naturally inoculated)

| Harvest No. | Treatment | % botrytis rots @ 10 weeks after treated | | % botrytis rots @ 19 weeks | |
|---|---|---|---|---|---|
| | | Single Layer Trays | Europacks | Single Layer Trays | Europacks |
| 1 | 1. 6AAP 100% | 0.19 | 0 | 0.38 | 0.1 |
| | 2. Control untreated | 12.4 | 6.57 | 15.00 | 7.33 |

| Harvest No. | Treatment | % botrytis rots @ 10 weeks after treated | | % botrytis rots @ 17 weeks | |
|---|---|---|---|---|---|
| | | Single Layer Trays | Europacks | Single Layer Trays | Europacks |
| 2 | 1. 6AAP 100% | 0 | 0.29 | 0.67 | 0.57 |
| | 2. Control untreated | 4.38 | 0.86 | 7.90 | 3.43 |

TABLE 15

6AAP Botrytis Trial 1 - Treatment after 51 hours

| Harvest No. | Treatment | % botrytis rots @ 9 weeks after treated | % botrytis rots @ 18 weeks |
|---|---|---|---|
| 1 | 1. AANB | 60 | 60 |
| | 2. CaCl2 (0.12%) | 60 | 60 |
| | 3. CaCl2 (1/10) | 63 | 63 |
| | 4. Beta-ionone | 18 | 41 |
| | 5. Ronilan 75u Al | 18 | 18 |
| | 6. 6AAP 100% | 0 | 0 |
| | 7. 6AAP 50% | 0 | 0 |
| | 8. 6AAP 25% | 0 | 0 |
| | 9. 6AAP 10% | 1 | 1 |
| | 10. Control untreated | 74 | 74 |
| 2 | 1. AANB | 38 | 38 |
| | 2. CaCl2 (0.12%) | 35 | 36 |
| | 3. CaCl2 (1/10) | 23 | 26 |
| | 4. Beta-ionone | 2 | 10 |
| | 5. Ronilan 75 ug Al | 4 | 6 |
| | 6. 6AAP 100% | 0 | 0 |
| | 7. 6AAP 50% | 0 | 0 |
| | 8. 6AAP 25% | 0 | 1 |
| | 9. 6AAP 10% | 0 | 0 |
| | 10. Control untreated | 30 | 30 |
| 3 | 1. CAH | 61 | 64 |
| | 2. CAL | 47 | 48 |
| | 3. BNB | 54 | 56 |
| | 4. delta decanolactone | 2 | 8 |
| | 5. Ronilan 75 ug Al | 55 | 57 |
| | 6. 6AAP 100% | 0 | 0 |
| | 7. massoilactone | 1 | 2 |
| | 8. 6AAP 25% | 0 | 0 |
| | 9. 6AAP 10% | 0 | 1 |
| | 10. Control untreated | 78 | 79 |

TABLE 16

6AAP Trial 4 - Automated droplet (naturally inoculated)

| Treatment | No. fruit treated | Botrytis rots @ 7–9 weeks | |
|---|---|---|---|
| | | No. | % |
| 6AAP (100%) | | | |
| contact wound | 6010 | 3 | 0.05 |
| outside wound | 698 | 2 | 0.29 |
| 6AAP (10%) | | | |
| contact wound | 2409 | 10 | 0.42 |
| outside wound | 99 | 1 | 1.01 |
| Control | 6708 | 364 | 5.43 |

2. EXPERIMENTAL SECTION 2

2.1 Antifungal Activity

Agar Diffusion Assay

Spore suspensions were prepared by washing sporulating plates or slopes of the test organism with 10 ml sterile 0.1% (v/v) Tween 80. The spore density of the aspirated volume was determined using an improved Neubauer haemocytometer. The spore suspension was used to inoculate molten nutrient agar maintained at 45° C. Two agar diffusion assays were employed; multi-well and agar overlay. For the multi-well assay, 3 ml aliquots of the inoculated molten nutrient agar was dispensed into each well of a leveled six well microtitre plate (Nunc) and allowed to solidify. For the agar overlay assay, 10 ml of the inoculated molten nutrient agar was poured over the surface of a petri dish (90 mm dia.) containing a uniform base layer of 10 ml 1% (w/v) water agar.

Solutions of test compounds were typically prepared in acetone and applied to sterile 6 mm diameter filter paper discs (Whatman no. 3.) After allowing the solvent to evaporate impregnated filter paper discs were placed on the surface of the solidified agar. For the multi-well assay one disc was placed at the centre of each well. For the agar overlay assay three discs were used per plate placed equidistant from each other and the centre of the plate. Plates were incubated and the diameters of the resulting zones of total inhibition were measured. Zones of partial inhibition were also noted.

TABLE 17

Figure 10A:
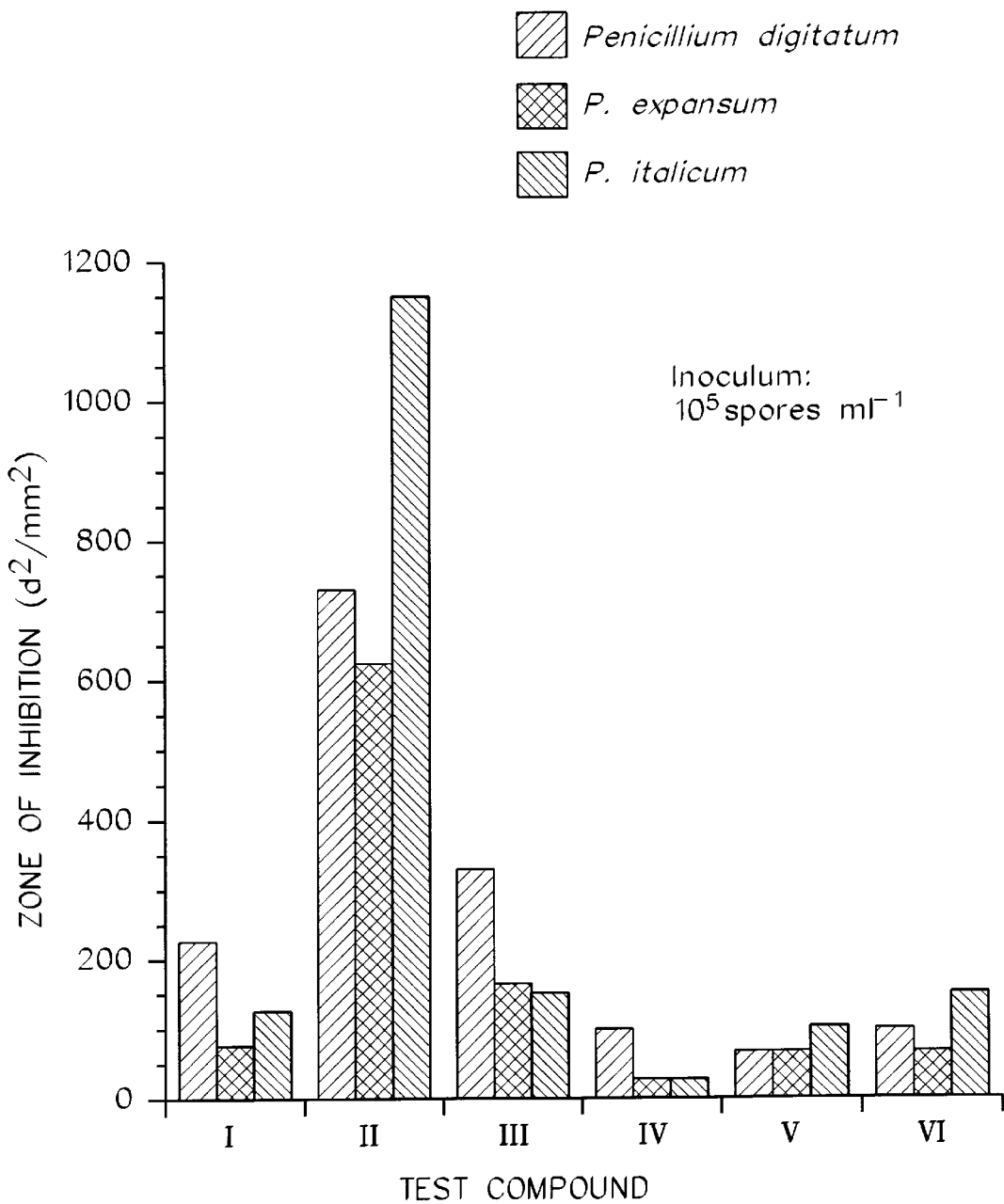
Figure 10B:
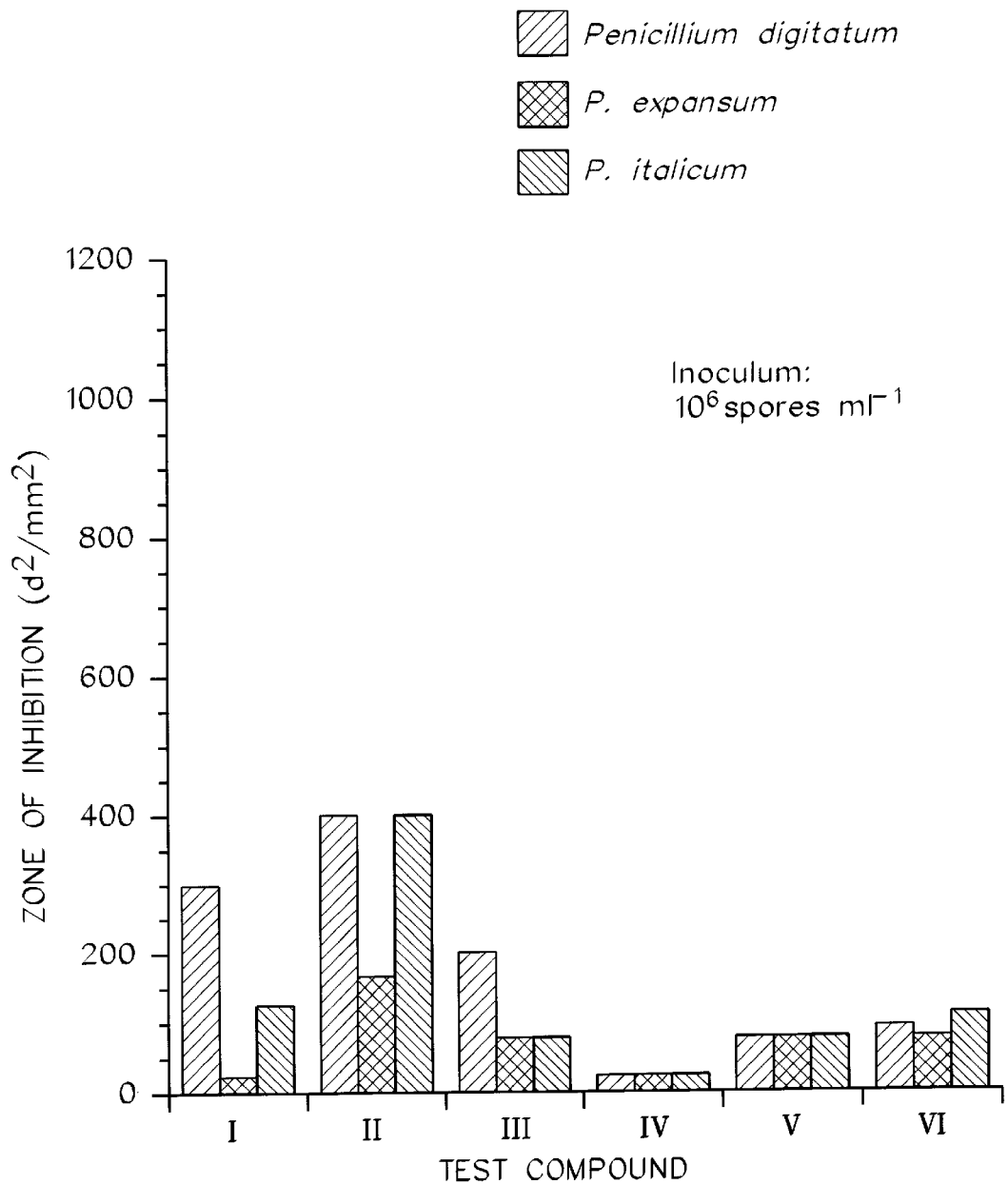
Figure 10C:
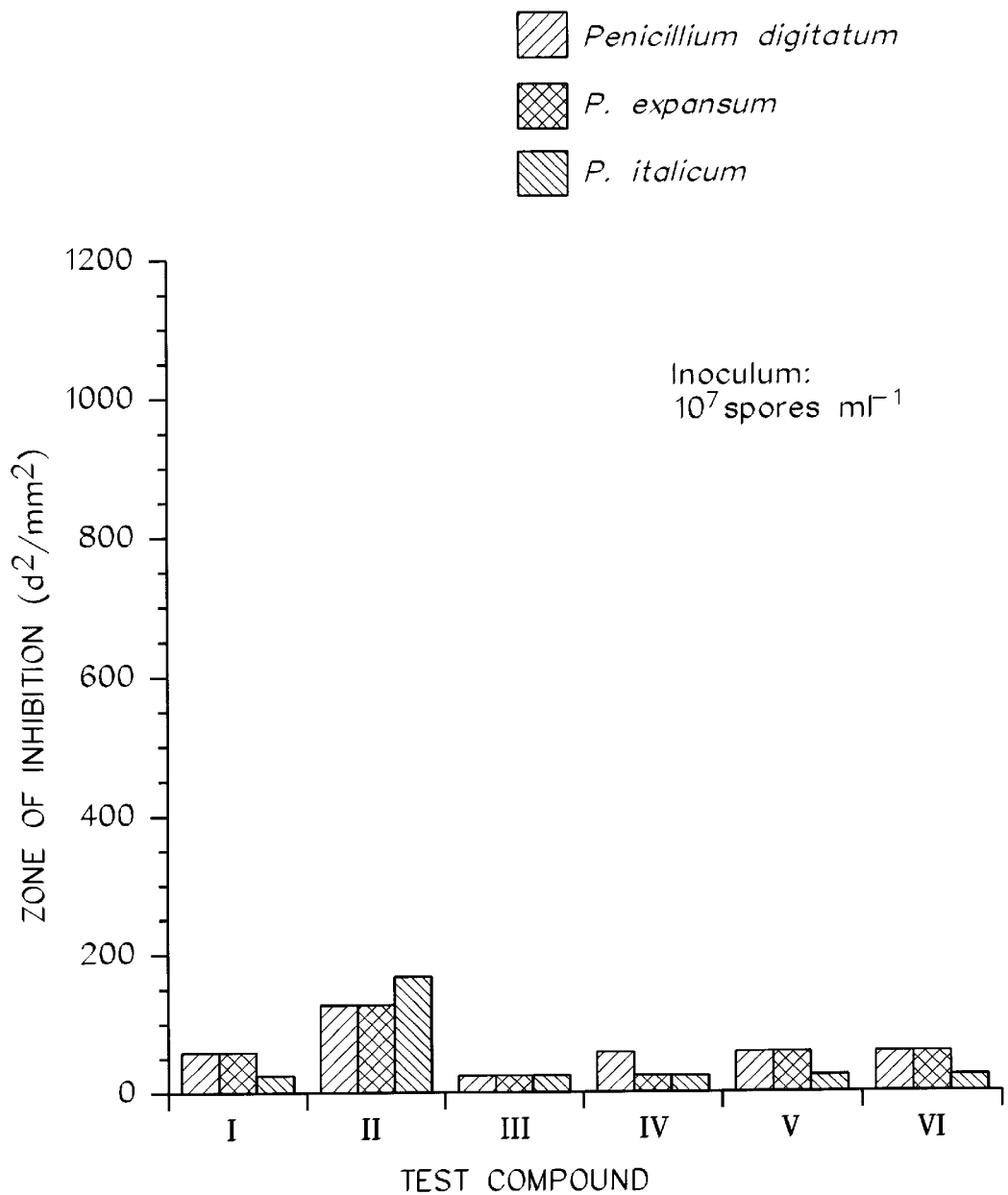
Figure 11A:
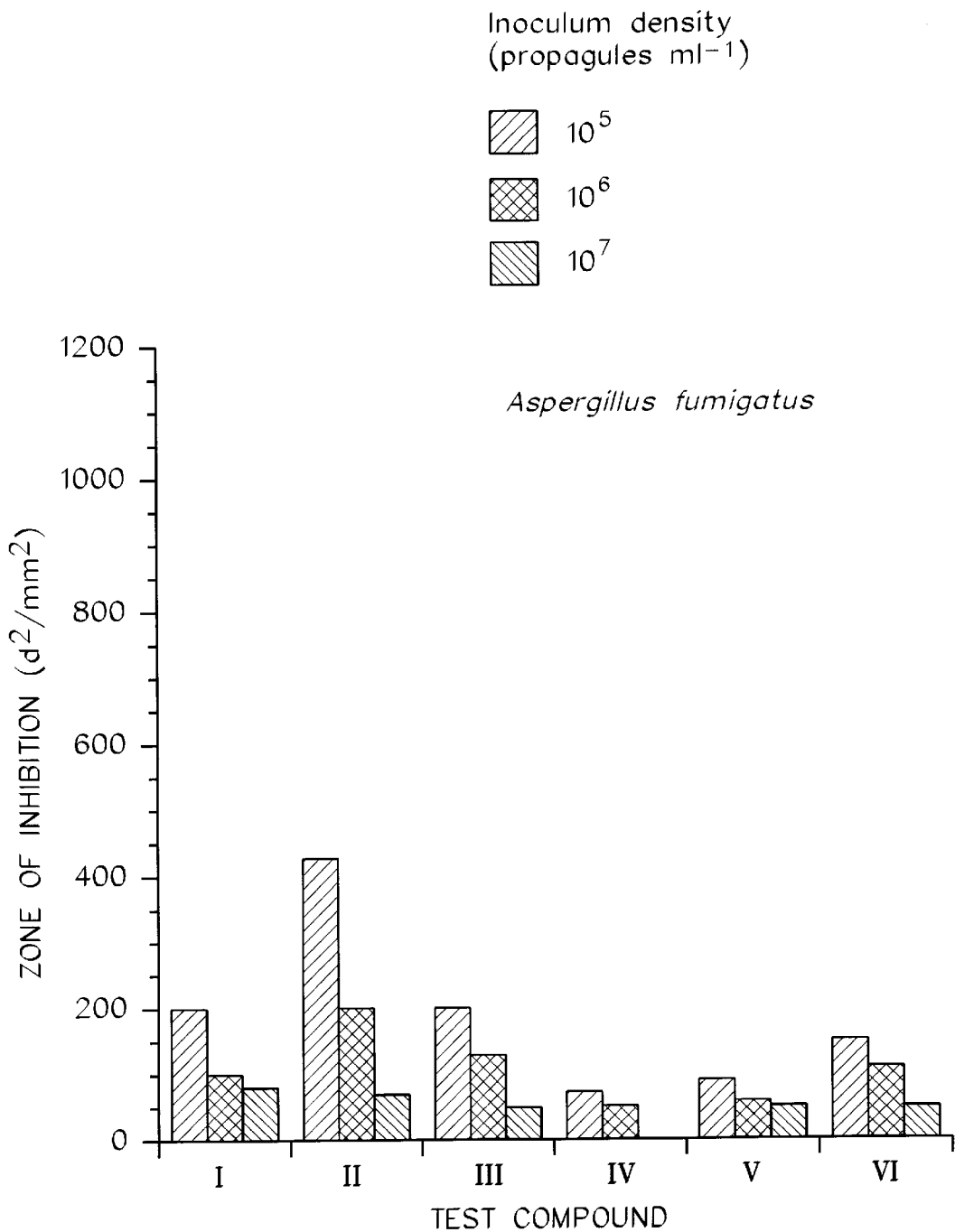
FIG. 11 Activity against human fungal pathogens of 500 μl each of 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). Activity was determined by the agar diffusion, multiwell assay and is recorded as the square of the diameter (mm) of the observed zone of inhibition.
Figure 11B:
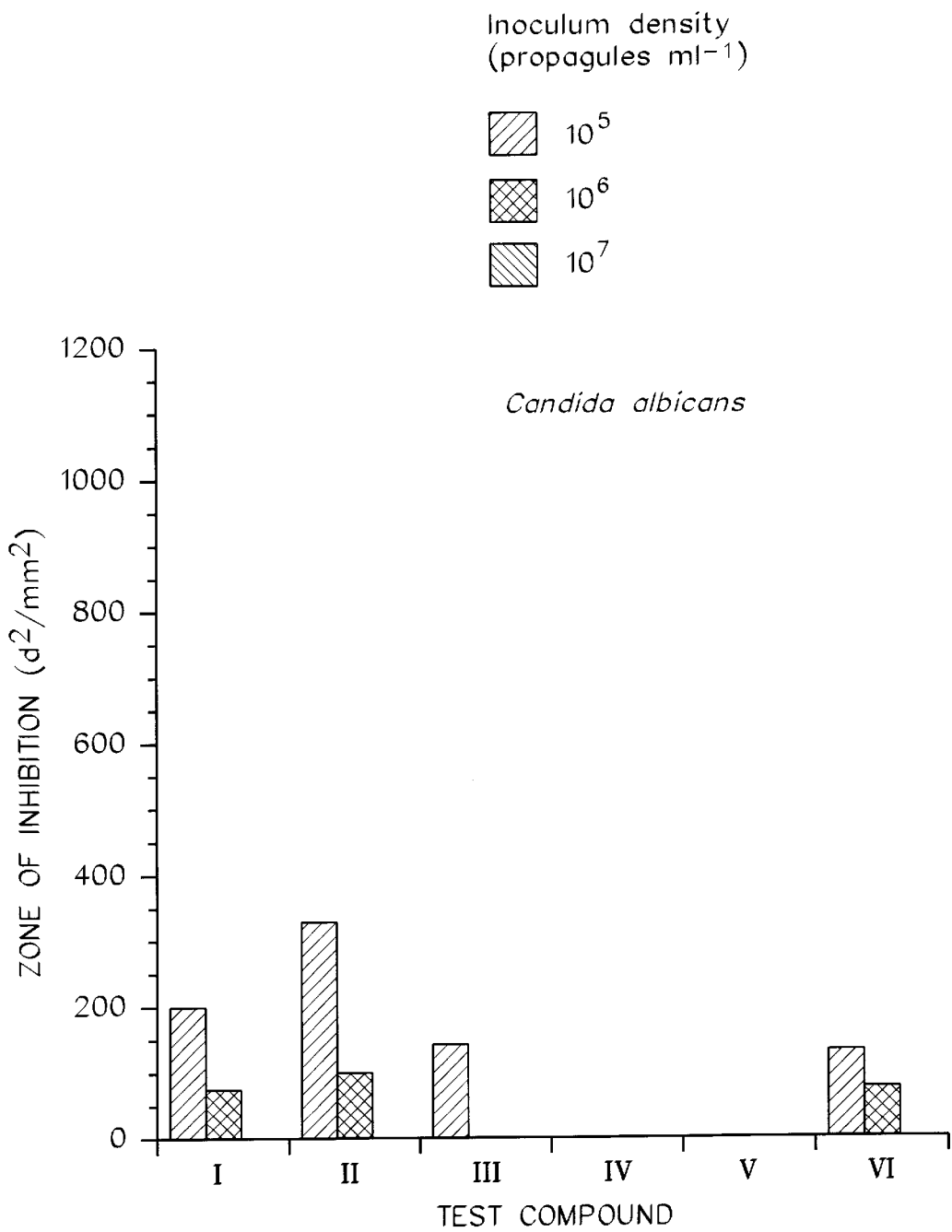
Figure 11C:
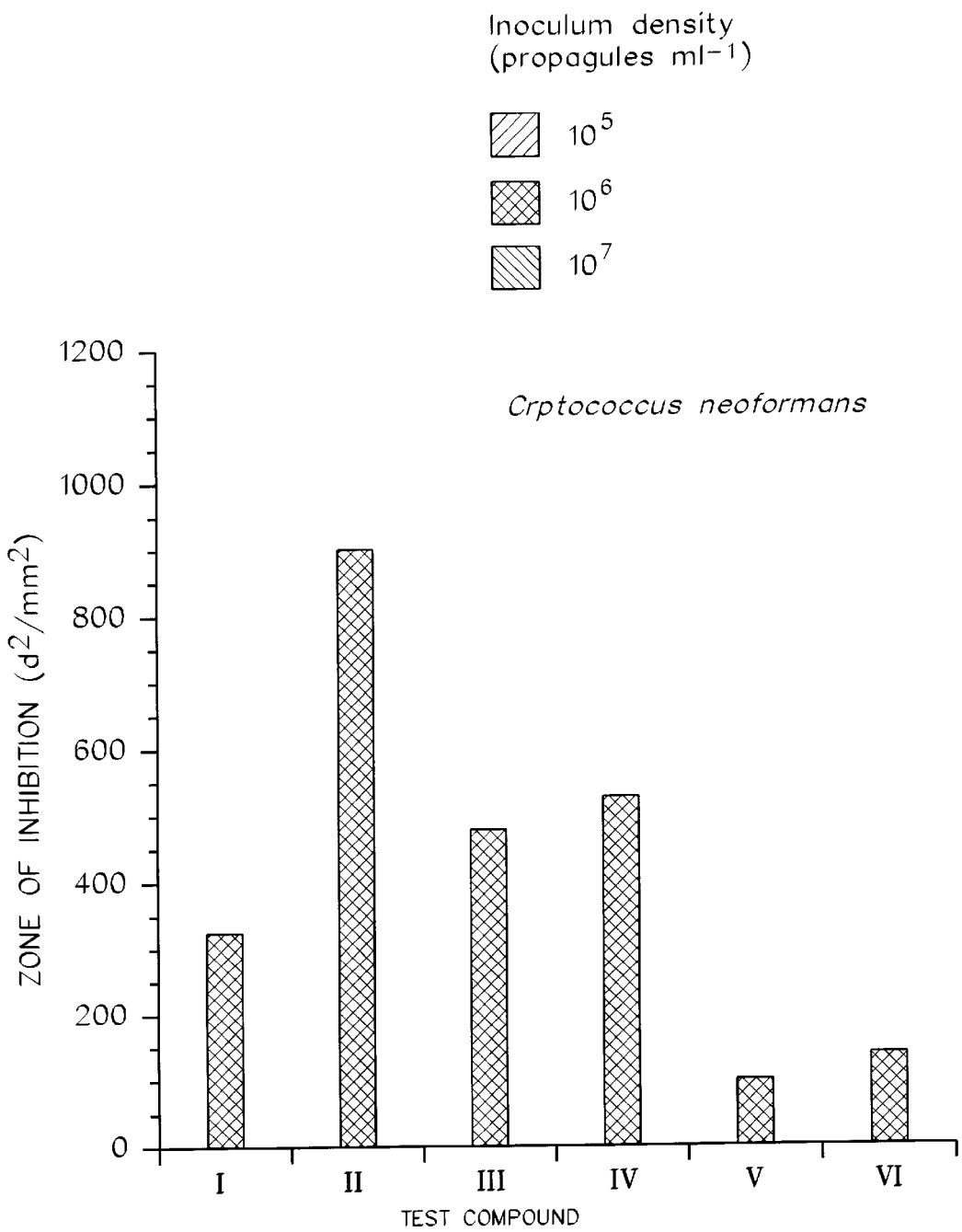
Figure 12:
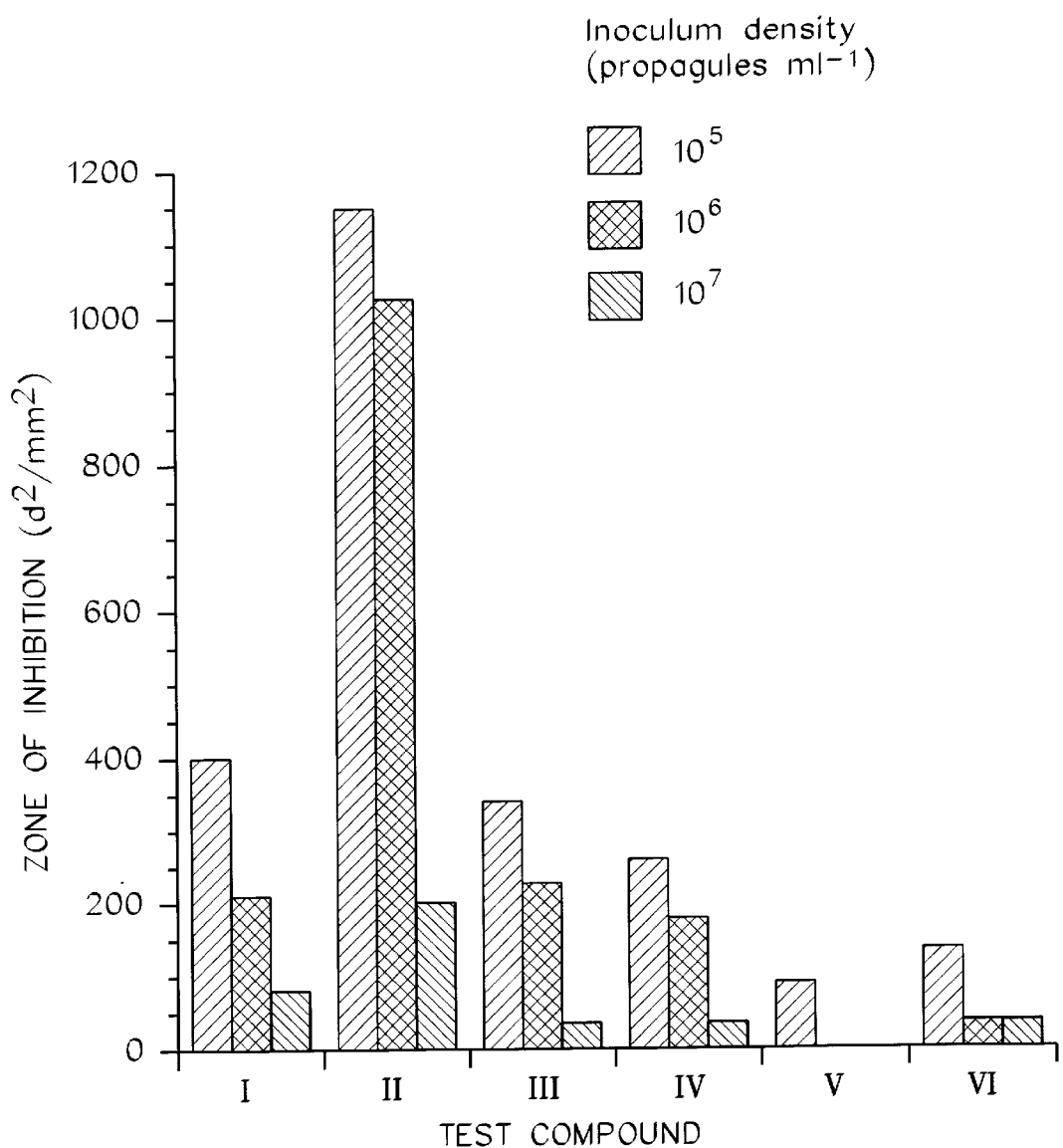
FIG. 12 Activity against Trichoderma harzianum ATCC 64870 of 500 μl each of 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). Activity was determined by the agar diffusion, multiwell assay. Test compounds were applied to filter paper discs and activity recorded as the square of the diameter (mm) of the observed zone of inhibition.
Figure 13:
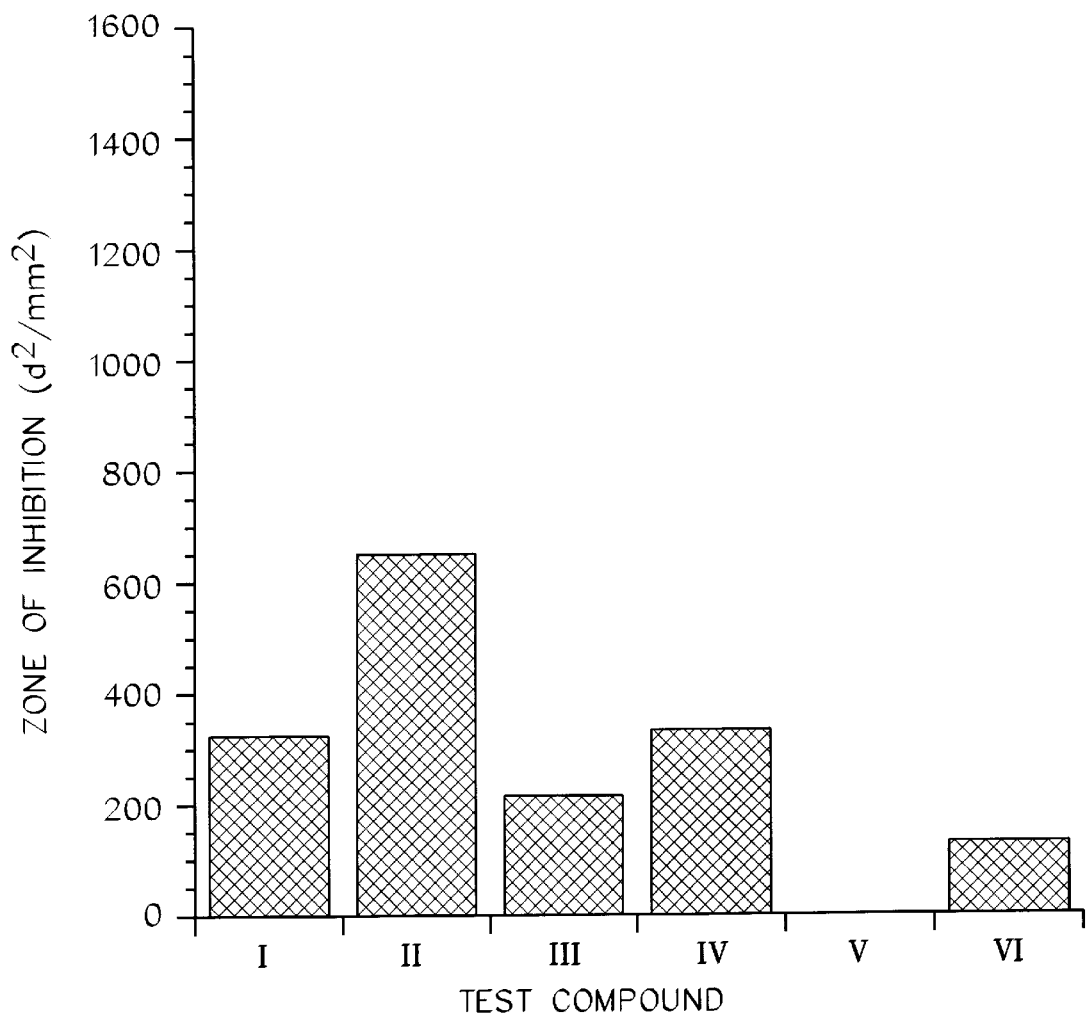
FIG. 13 Activity against Botrytis cinerea BC18 of 1 mg each of 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). Activity was determined by the agar diffusion, overlay assay. Test compounds were applied to filter paper discs and activity recorded as the square of the diameter (mm) of the observed zone of inhibition.
Figure 14:
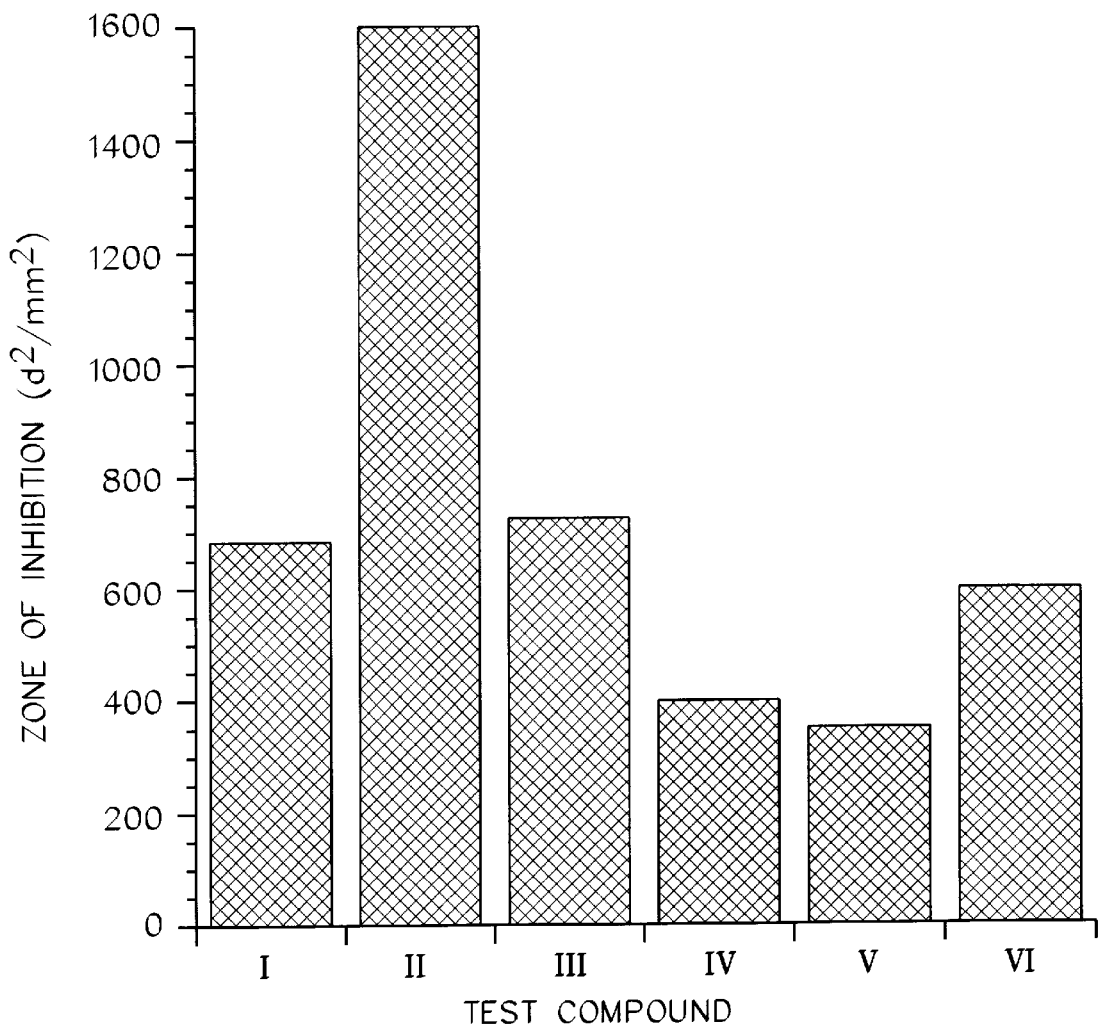
FIG. 14 Activity against Monilinia fructicola GQMF3 of 1 mg each of 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). Activity was determined by the agar diffusion, overlay assay. Test compounds were applied to filter paper discs and activity recorded as the square of the diameter (mm) of the observed zone of inhibition.
Figure 15:
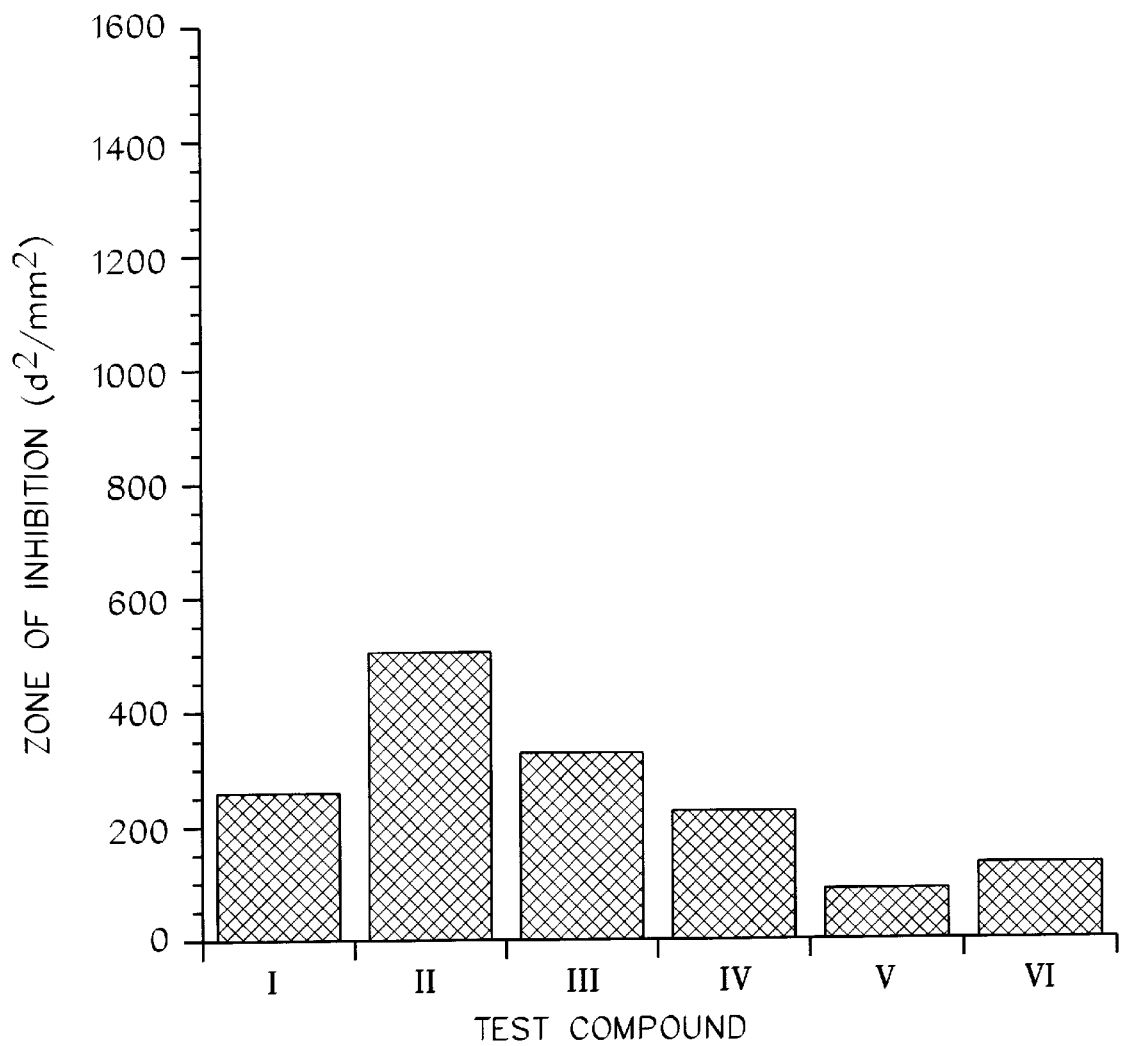
FIG. 15 Activity against Penicillium digitatum (ex Scott) of 1 mg each of 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS )-dihydro-5-octyl-2H-furan-2-one (V) and (RS )-tetrahydro-6-heptyl-2H-pyran-2-one (VI). Activity was determined by the agar diffusion, overlay assay. Test compounds were applied to filter paper discs and activity recorded as the square of the diameter (mm) of the observed zone of inhibition.
Figure 16:
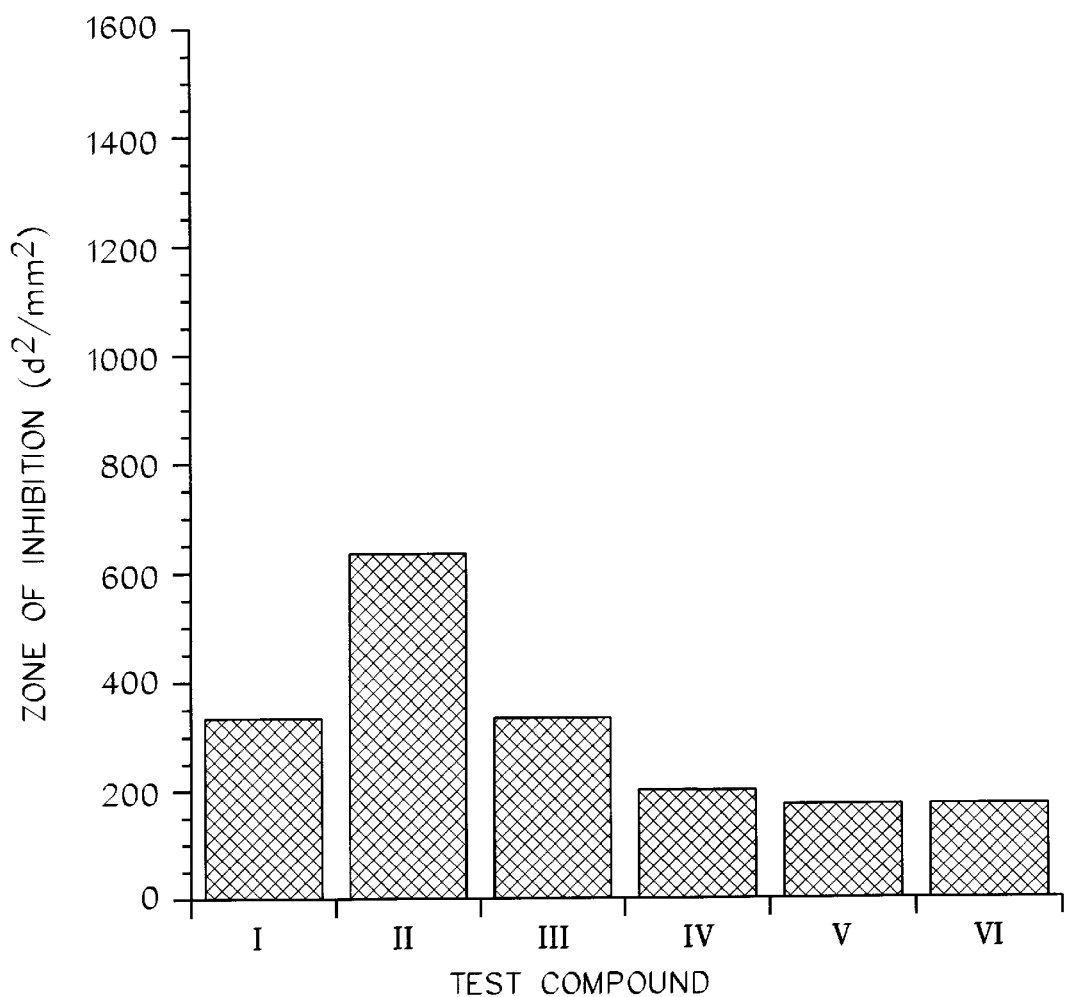
FIG. 16 Activity against Alternaria alternata of 1 mg each of 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). Activity was determined by the agar diffusion, overlay assay. Test compounds were applied to filter paper discs and activity recorded as the square of the diameter (mm) of the observed zone of inhibition.

| TEST ORGANISM | NUTRIENT AGAR | ASSAY TECHNIQUE | INCUBATION TEMP./TIME | RESULTS |
|---|---|---|---|---|
| Penicillium digitatum (ex Bala) | PDA | Multi-well | 20° C./2 days | FIG. 10 |
| P. expansum (ex Bala) | PDA | Multi-well | 20° C./2 days | FIG. 10 |
| P. expansum (ex Scott) | PDA | Agar overlay | 25° C./1 day | FIG. 15 |
| P. italicum (ex Bala) | PDA | Multi-well | 20° C./2 days | FIG. 10 |
| Trichoderma harzianum (ATCC 64870) | PDA | Multi-well | 20° C./2 days | FIG. 12 |
| Botrytis cinerea | PDA | Agar overlay | 25° C./1 day | FIG. 13 |
| Monilinia fructicola | PDA | Agar overlay | 25° C./1 day | FIG. 14 |
| Alternaria alternata | PDA | Agar overlay | 25° C./1 day | FIG. 16 |
| Aspergillus fumigatus | PDA | Multi-well | 37° C./1 day | FIG. 11 |
| Candida albicans | YMA | Multi-well | 37° C./1 day | FIG. 11 |
| Crptococcus neoformans | YMA | Multi-well | 26° C./1 day | FIG. 11 |

Test organisms employed in either of the two agar diffusion assays. The nutrient agar employed was either potato dextrose agar (PDA) or yeast morphology agar (YMA.) The incubation time and temperature before recording the observed zones of inhibition are given and results recorded in the figures and/or tables cited.

2.2 Antifungal Activity

Agar Dilution Assay

A two-fold dilution series of test compound was prepared in sterile 0.1% (v/v) Tween 80 at four times final concentration. PDA was prepared at four thirds final strength and maintained at 55° C. For each step of the dilution series one volume of test compound emulsion was gently mixed with three volumes of molten PDA. A 3 ml volume of the PDA containing test compound was then transferred to one well of a six well multi-well plate (Nunc) and allowed to solidify. Final concentrations were 0.1, 0.05, 0.025, 0.0125 and 0.00625% (v/v) with a control containing 0.025% (v/v) Tween 80 alone.

Mycelia bearing agar plugs of 4 mm diameter were aseptically excised from a source plate of non-sporulating test organism and placed at the center of each well with the colony bearing surface uppermost. Plates were incubated at 20° C. for 5 days, after which time outgrowth from the inoculum plug was recorded. Assays for a dilution series of each compound tested were performed in triplicate.

TABLE 18

Test organism employed in the agar dilution assay. Results are recorded in the table cited.

| TEST ORGANISM | RESULTS |
|---|---|
| Sclerotinia sp. | Table 20 |
| Botrytis cinerea (ex Bala) #1 | Table 20 |
| B. cinerea (ex Bala) #2 | Table 20 |
| Diplodia pinea (ICMP 5286) | Table 21 |
| Ophiostoma picea (FK150) | Table 22 |
| Cyclaneusma minus (ex FRI) | Table 22 |

2.3 pH-Dependency of Antifungal Activity

Agar Diffusion Assay

Figure 17A:
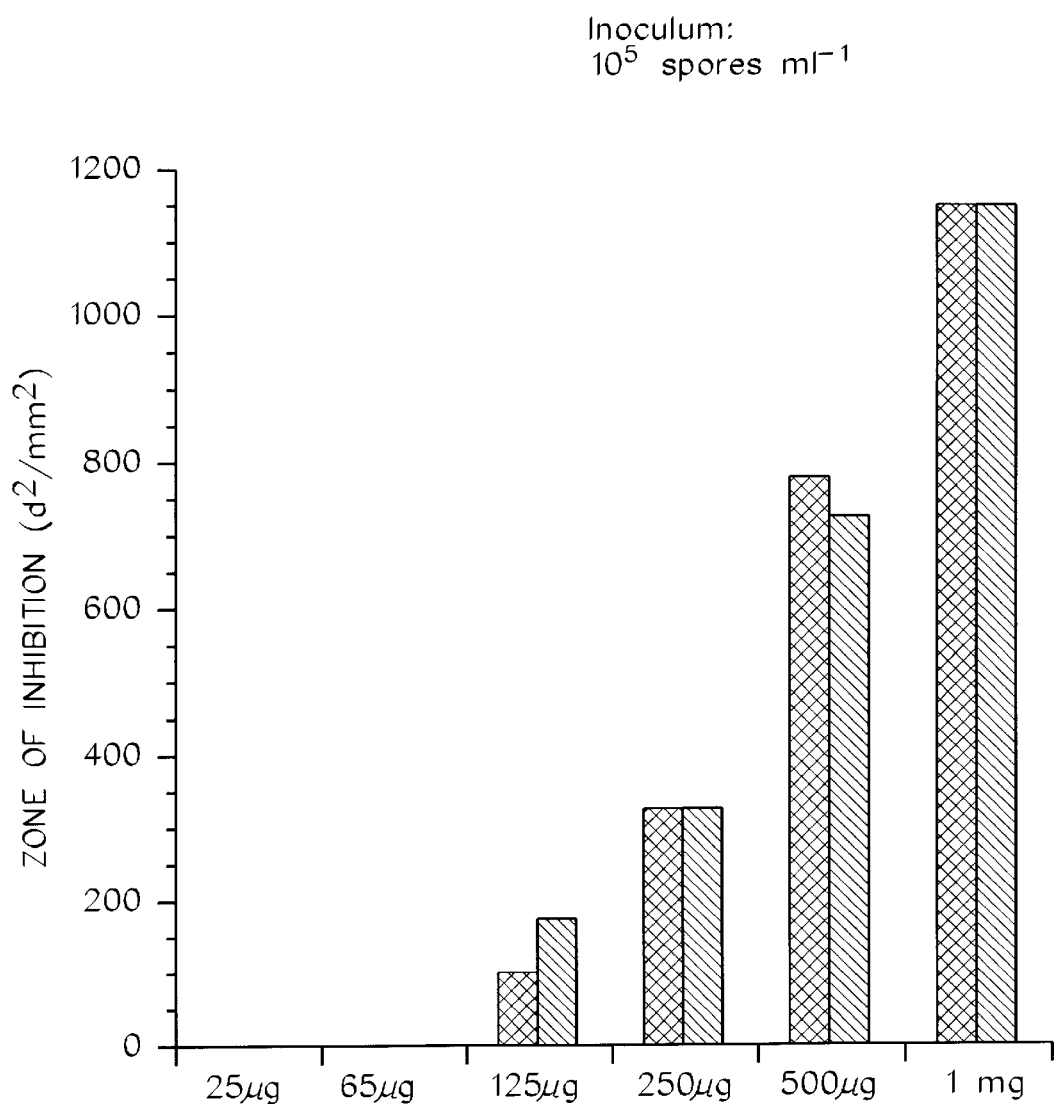
FIG. 17 Activity against Penicillium expansum (ex Bala) of increasing amounts of (R)-5,6-dihydro-6-pentyl-2H-pyran-2-one (II) at pH 5.3 (solid) and pH 4.3 (shaded). Activity was determined by the agar diffusion, multi-well assay. pH of PDA was adjusted with lactic acid. Activity recorded as the square of the diameter (mm) of the observed zone of inhibition.
Figure 17B:
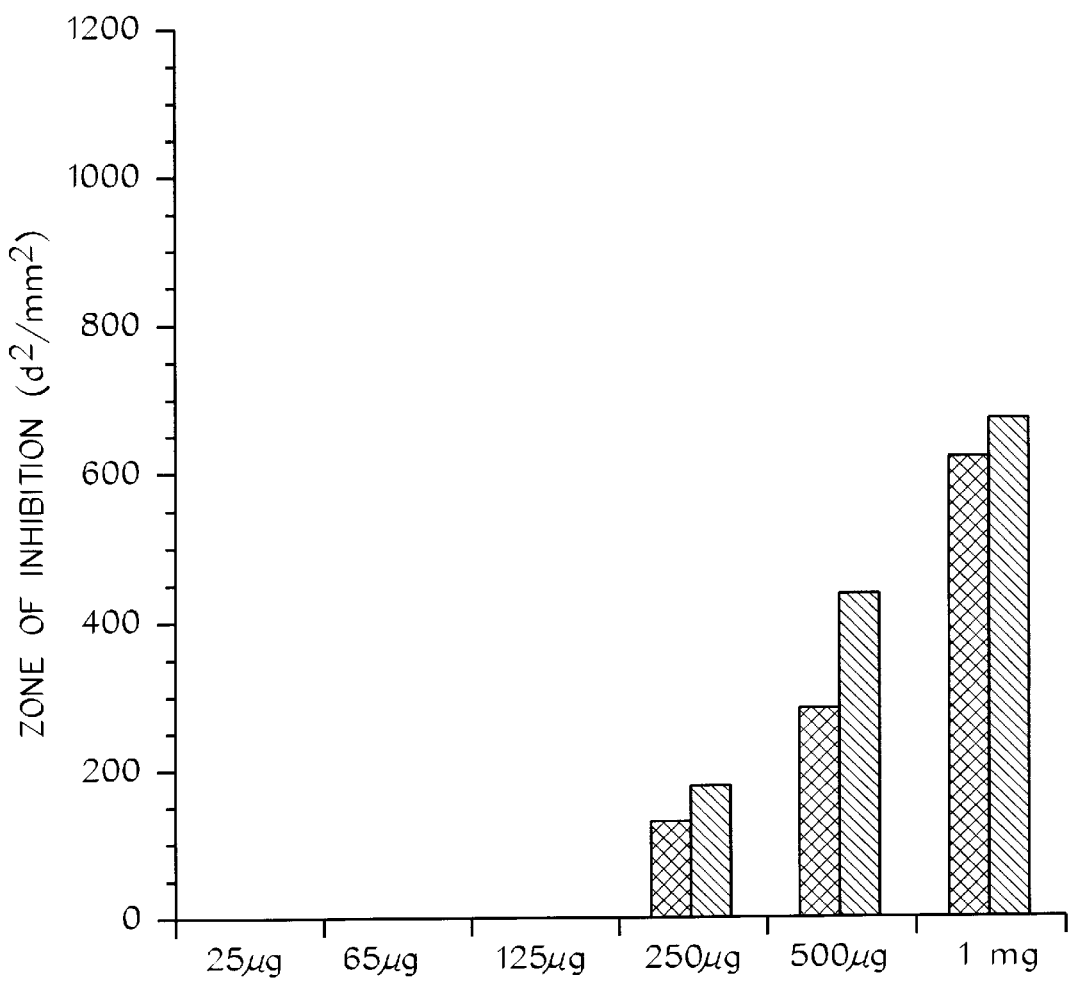
Figure 17C:
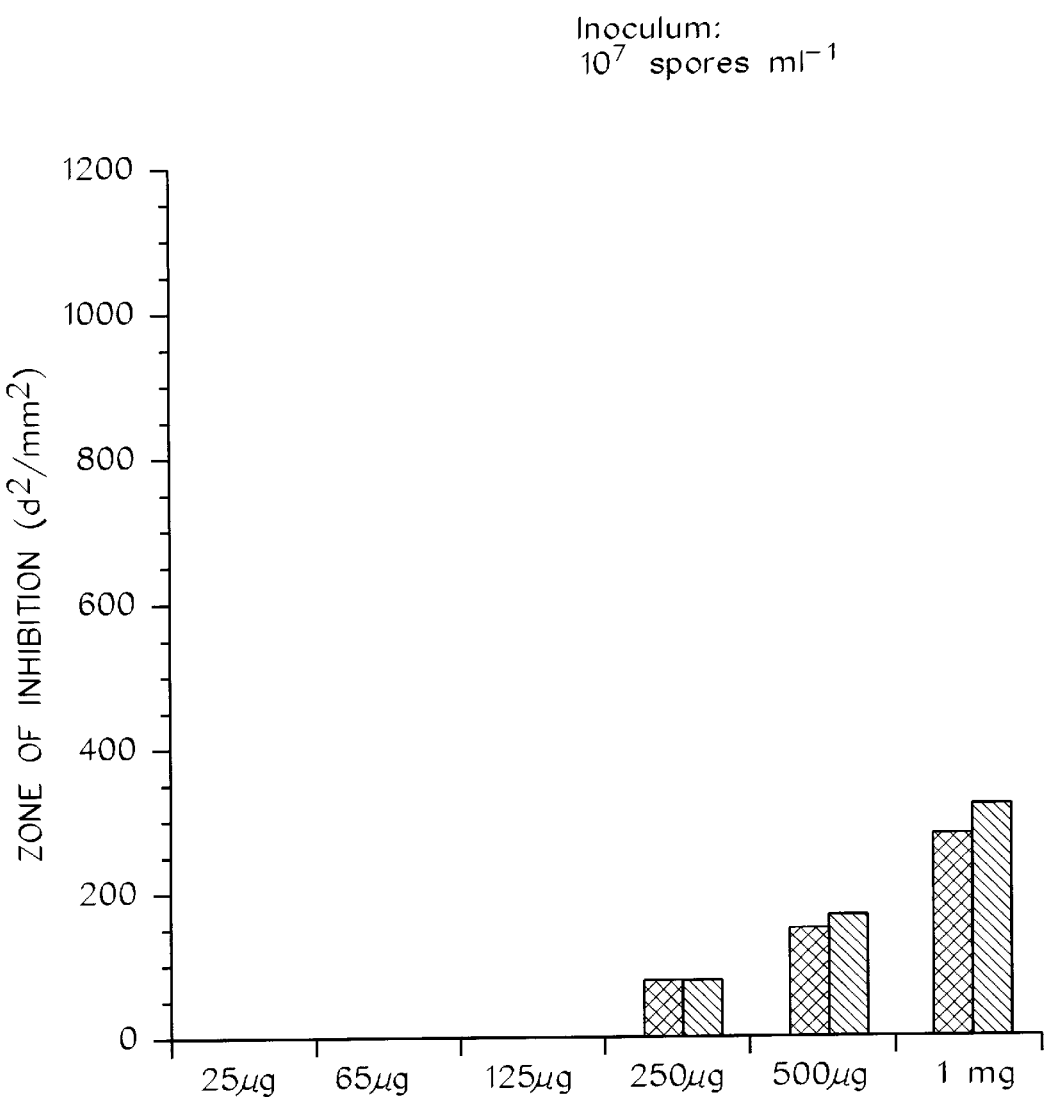

Potato dextrose agar (pH 5.3) was acidified with lactic acid and the multi-well agar diffusion assay (see above) employed using Penicillium expensum (ex Bala) as test organism. Results are recorded in FIG. 17.

2.4 Phytotoxicity

Etiolated Wheat Coleoptile

Figure 18:
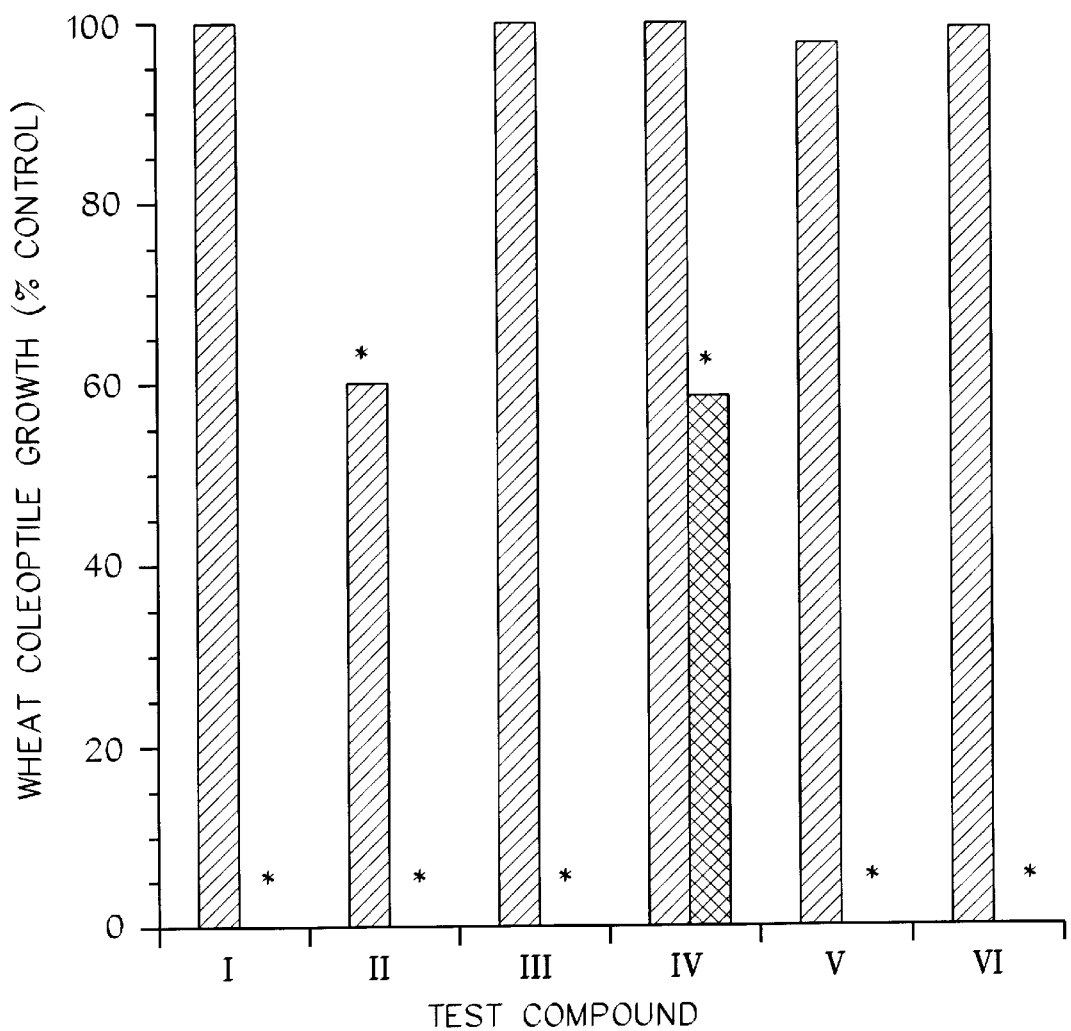
FIG. 18 Etiolated wheat coleoptile assay. The growth of wheat coleoptile sections is reported as a percentage of control for two concentrations: $10^{-4}$M (solid) and $10^{-3}$M (shaded). The compounds tested were 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). * Denotes significant inhibition ($P<0.01$). [a]Duplicate bioassays.

The assay was performed as previously described (12). Wheat seeds (Triticum aestivum L. cv., Wakeland) were sown on moist vermiculite and incubated in the dark for four days at 22° C. (±1° C.). Under illumination from a green safelight and using a Van der Weij guillotine, 4 mm sections of coleoptile were excised 2 mm below the coleoptile tip. Ten coleoptile sections were placed in a test tube containing 2 ml of phosphate-citrate buffer (pH 5.6) and 2% (w/v) sucrose. Test compounds were added in 10 µl acetone to yield final concentrations of $10^{-3}$, $10^{-4}$ and $10^{-5}$ M. Length of the sections was measured after incubation for 18 hours at 22° C. (±1° C.). Data were statistically analyzed and the 0.01 level of confidence accepted (13). Assays were performed in duplicate. Results are recorded in FIG. 18.

2.5 Phytotoxicity

Lettuce Seed Germination

The assay was performed as described by Claydon et al. (1987) (14). A glass coverslip was placed at the centre of a petri dish lined with moist filter paper and twenty five lettuce seeds cv. Webbs Wonderful were randomly scattered over the filter paper surface. A volume of 5 µl of test compound was applied to the glass coverslip and the petri dish lid replaced. Petri dishes, four per test compound, were incubated in the dark at 20° C. for 3 days. The number of seeds germinating and the appearance of the emerging radicle was noted. Results are recorded in Table 22.

2.6 Phytotoxicity

Bean Seedlings

Seeds of dwarf bean cv. Greencrop were glasshouse grown in a commercial potting mix until the embryo leaves had fully expanded and the trifoliate leaves of the apical tip were in the crook stage. Seedlings at this growth stage were treated in sets of four with a foliar spray application of test compound emulsified in 0.1% (v/v) Tween 80. Thorough wetting of the leaf surface was achieved (typically 5 ml total volume.) Compounds were tested at concentrations of $10^{-3}$, $10^{-2}$, 0.1 and 1% (v/v) with 0.1% (v/v) Tween 80 alone as a control. Growth and appearance of plants was noted on day one and day seven following application.

2.7 Application

Prevention of Postharvest Storage Rot on Citrus

Recently harvested, organically grown fruit were rinsed successively in two baths of tap water and individually hand dried. "Prick" wounds (c. 2 mm deep, 1 mm diameter) were made on opposite sides of each fruit. Wounds were made on the equatorial line of the fruit and their position marked by a line drawn at the picking wound. Four sets of twelve fruit were selected at random. Fruit for treatment were placed well spaced in a hung wire basket and massoialactone applied as a nebulised emulsion in 0.1% (v/v) Tween 80 so as to achieve a complete covering of the fruit surface. A total volume of c. 35 ml was employed. Massioalactone was applied at rates of 1% (v/v) and 10% (v/v), with 0.1% (v/v) Tween 80 alone as a control. Excess application was allowed to drip from the fruit before transferring, sets of fruit to paper lined, sealed 2 L plastic containers. Two control sets were prepared. Fruit were incubated at 22° C. (±1° C.) for a total of seven days. On the second day of incubation a portion from a fruit uniformly covered with Penicillium mold was introduced into the containers for one of the controls, 1% (v/v) massoialactone and 10% (v/v) massoialactone treatments. After incubation for seven days fruit were inspected for the presence of rots.

2.8 Application

Prevention of Sapstain in Wood 2.8.1 Laboratory Studies

Figure 19:
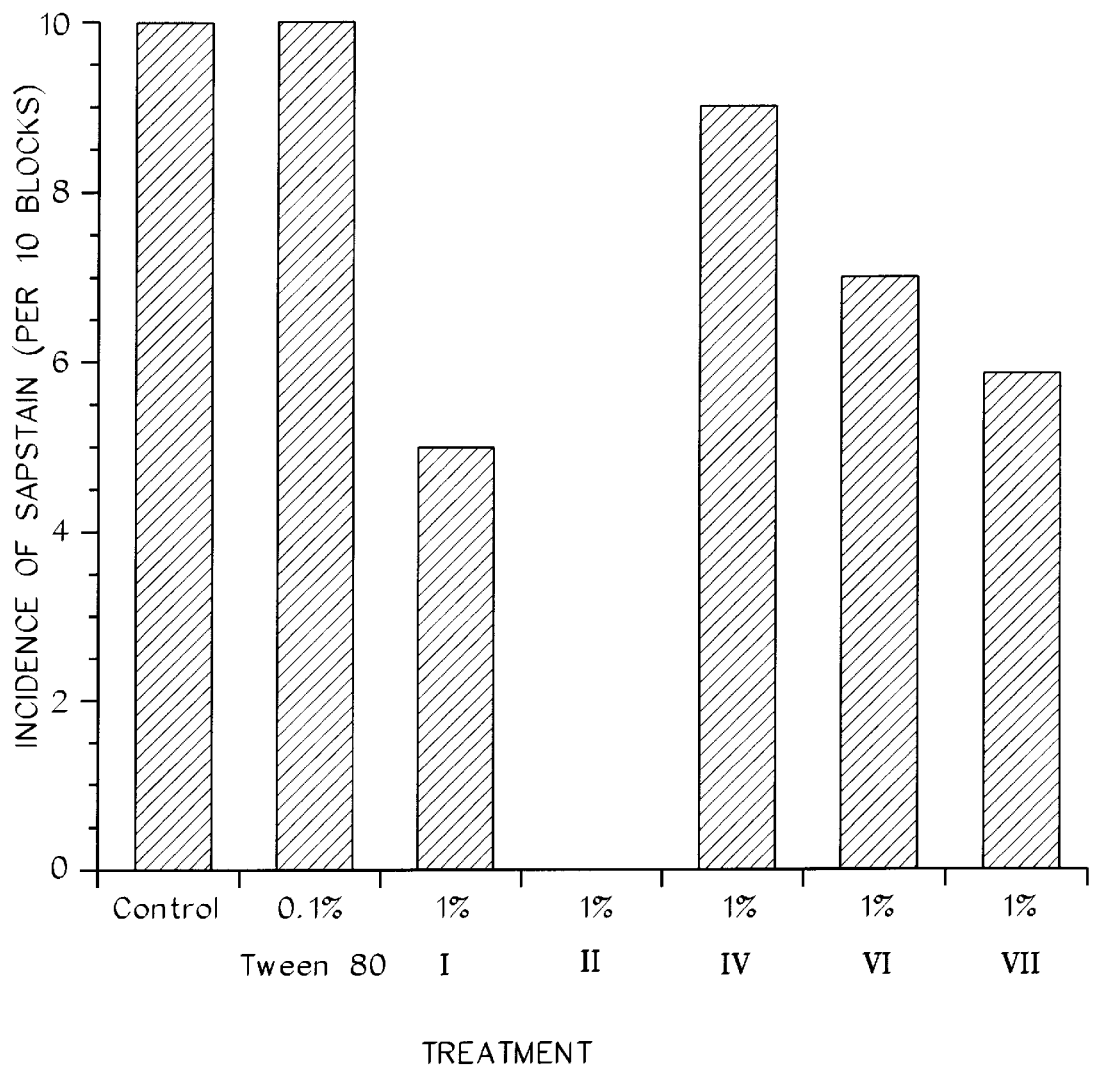
FIG. 19 Incidence of sapstain on treated blocks following inoculation and incubation at 25° C. (±1°) for two weeks. Blocks were treated by dipping in 1% (v/v) emulsions of the test compounds prepared in 0.1% (v/v) Tween 80. The compounds tested were 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V), (RS)-tetrahydro-6-heptyl-2H-pyran-2-one (VI) and (RS)-tetrahydro-6-hexyl-2H-pyran-2-one (VII).

Freshly sawn wood blocks (50×50×7 mm) were sterilised by γ-irradiation. Blocks were dipped individually in a 1 or 10% (v/v) emulsion of test compound prepared in sterile 0.1% (v/v) Tween 80. Each block was dipped for 30 seconds with gentle agitation and then placed on edge and allowed to drain. Single blocks were inoculated with 200 µl of a spore suspension (c. $10^6$ spores $ml^{-1}$) of sapstaining organisms FK64 and FK150 and placed in 500 ml glass jars. Each glass jar contained a filter paper disc moistened with 2 ml sterile distilled water and was sealed. Wood blocks were not in direct contact with the filter paper discs. Ten wood blocks were employed per treatment set. The wood blocks were incubated at 25° C. for 7 to 10 days and scored for the presence or absence of sapstain. Results are recorded in FIGS. 18 and 19.

Figure 20:
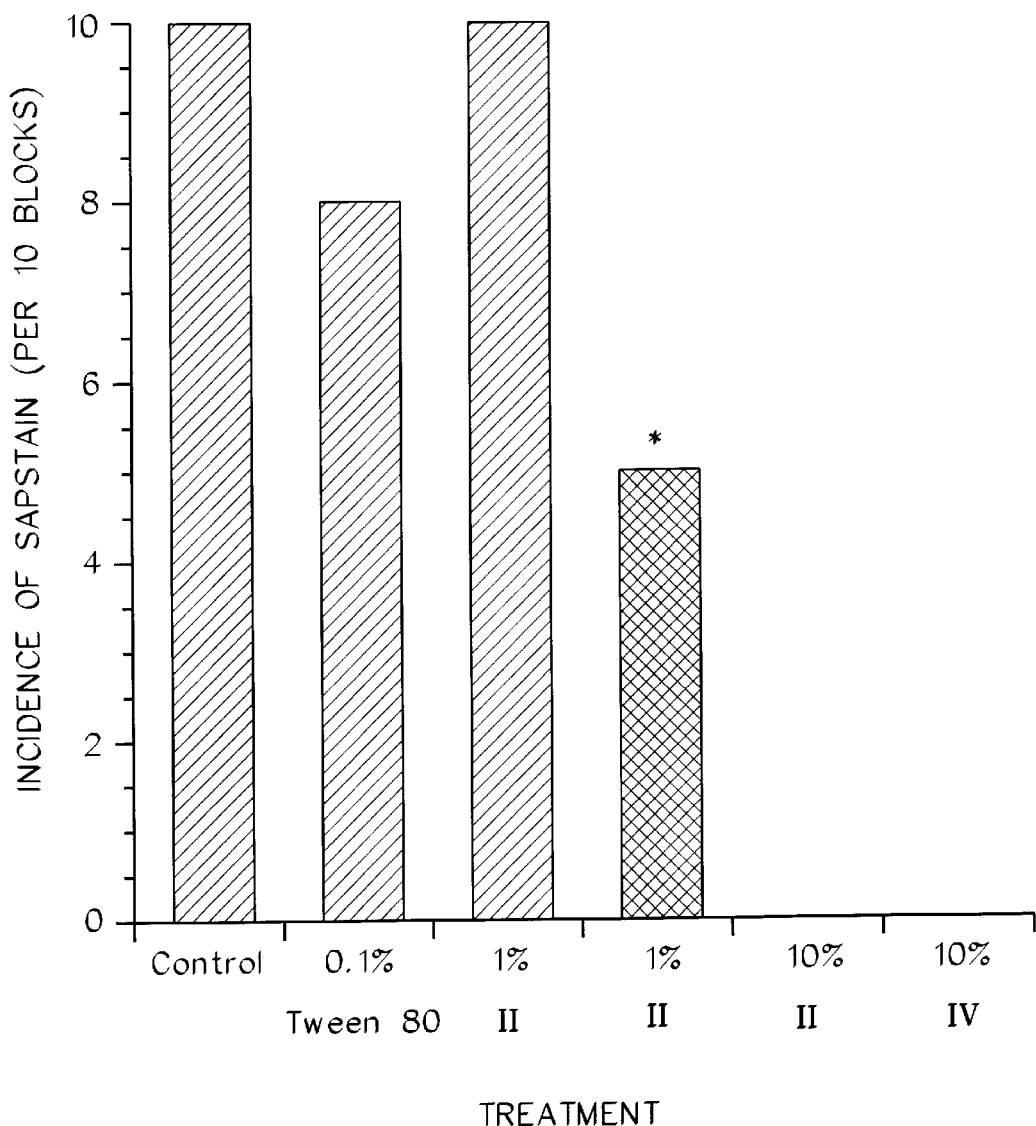
FIG. 20 Incidence of sapstain on treated blocks following inoculation and incubation at 25° C. (±1°) for two weeks. Blocks were treated by dipping in 1% (v/v) or 10% (v/v) emulsions of the test compounds prepared in 0.1% (v/v) Tween 80. The compounds tested were (R)-5,6-dihydro-6-pentyl-2H-pyran-2-one (II) and (RS )-tetrahydro-6-pentyl-2H-pyran-2-one (IV). *Colonized by Trichoderma.

One liter volumes of 10% (v/v) emulsions of either massoialactone II or VII (RS)-tetrahydro-6-hexyl-2H-pyran-2-one were prepared in 0.1% (v/v) Tween 80. Individual, freshly sawn wood blocks (c. 300×100×50 mm) were dipped for 30 seconds with agitation and allowed to drain. Treatment with a commercial fungicide, NP-1, was included for comparison. Untreated (undipped) blocks were employed as a control. Wood blocks from the same treatment were placed in 4 by 4 stacks, and stacks were replicated three times. Individual blocks from each treatment were identified by dipping order; sixteen groups of three. One block from each group was placed in each of the three replicate stacks. Blocks were randomised within each sixteen block stack. The percentage sapstain on the upper and lower surface was assessed by visual inspection at monthly intervals. Results are recorded in FIG. 20.

Figure 21:
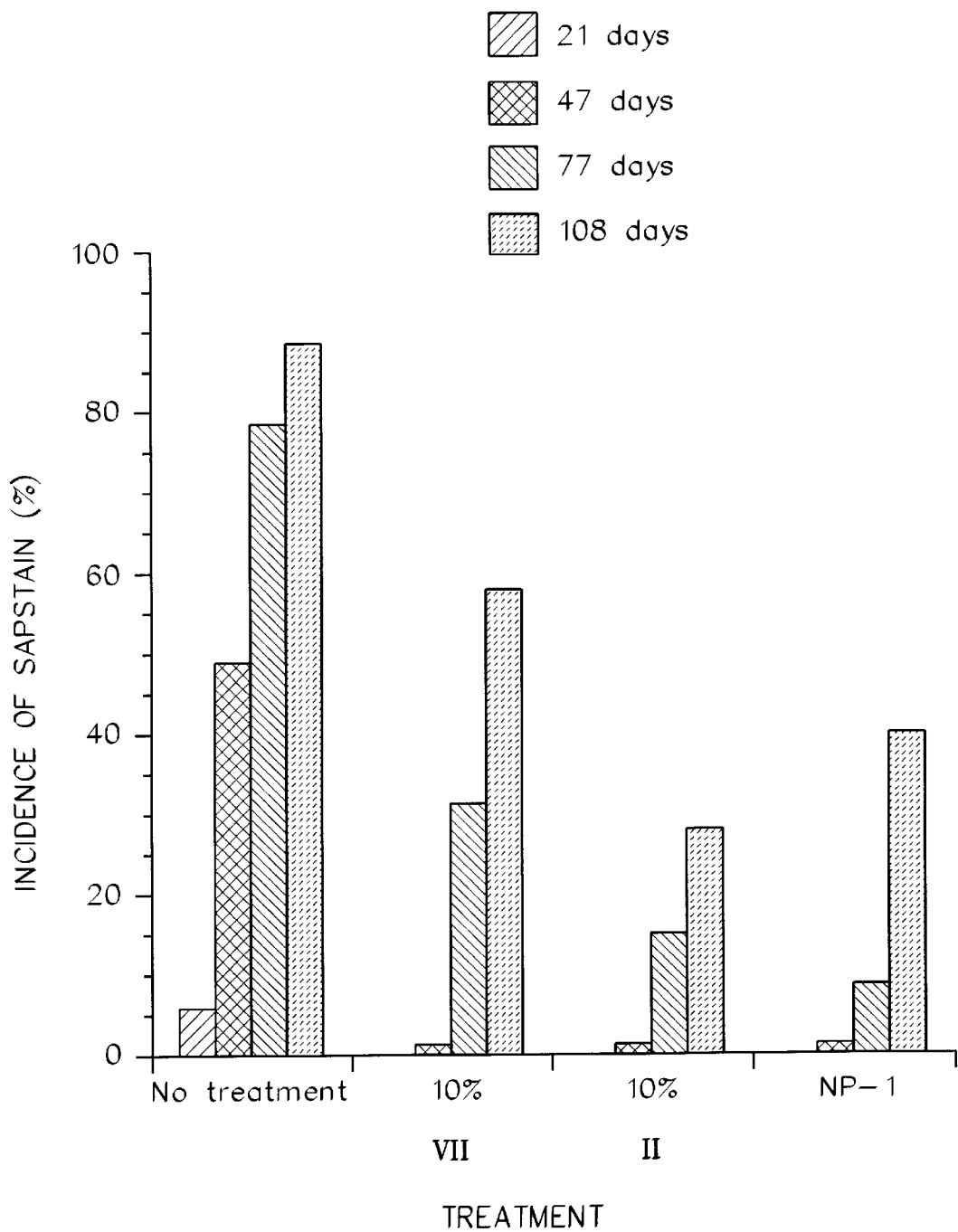
FIG. 21 Incidence of sapstain on treated blocks following incubation under field conditions. Blocks were treated by dipping in 10% (v/v) emulsions of the test compounds prepared in 0.1% (v/v) Tween 80. The compounds tested were (R)-5,6-dihydro-6-pentyl-2H-pyran-2-one (II) and (RS)-tetrahydro-6-hexyl-2H-pyran-2-one (VII). The upper and lower surfaces of each block were visually assessed for the presence of sapstain at the times shown. The treatment NP-1 was included for comparative purposes.
Figure 22A:
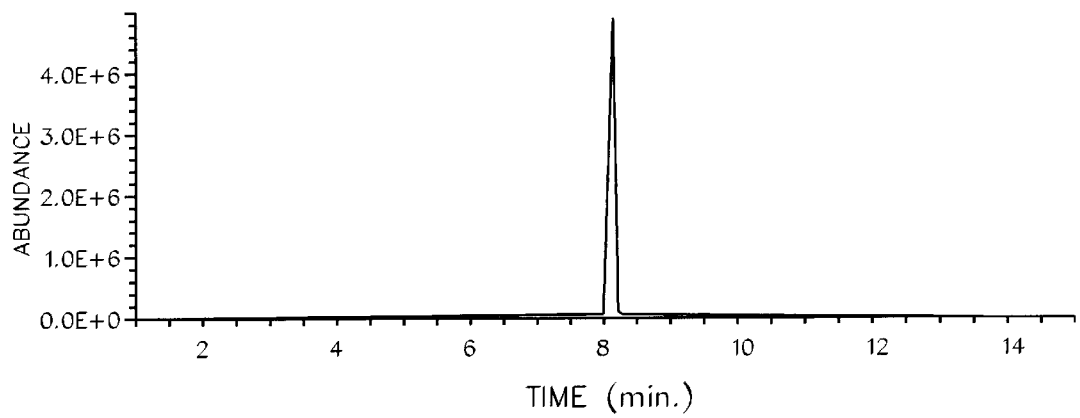
FIG. 22 Gas chromatography (upper trace) and mass spectrum (lower histogram) of 6-pentyl-2H-pyran-2-one (I). Chromatography was performed using an HP-1 crosslinked methyl silicone capillary column (12×0.2 mm, 0.33 µm film) with helium as carrier gas at a flow rate of 1 ml/min, 50:1 split injector. Initial oven temperature was 100° C. raised to 136° C. at 4° C. min$^{-1}$.
Figure 22B:
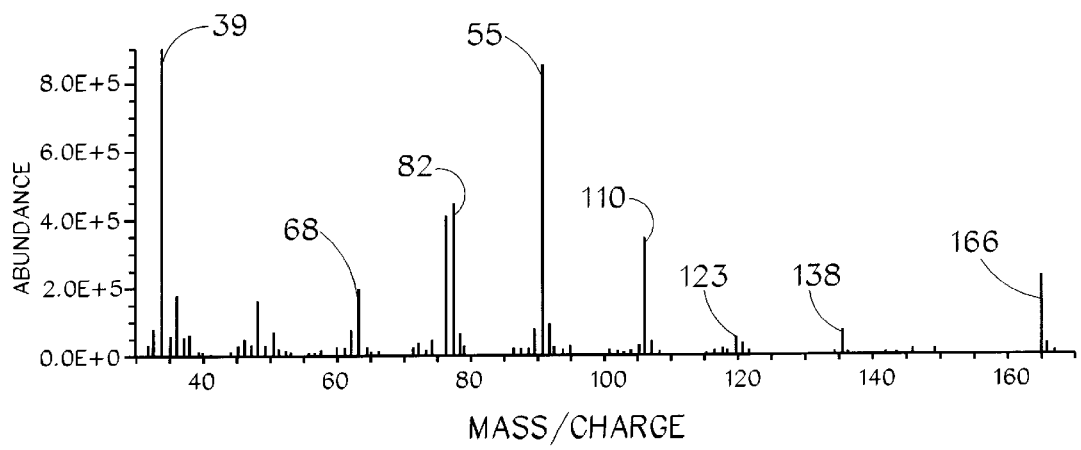
Figure 23A:
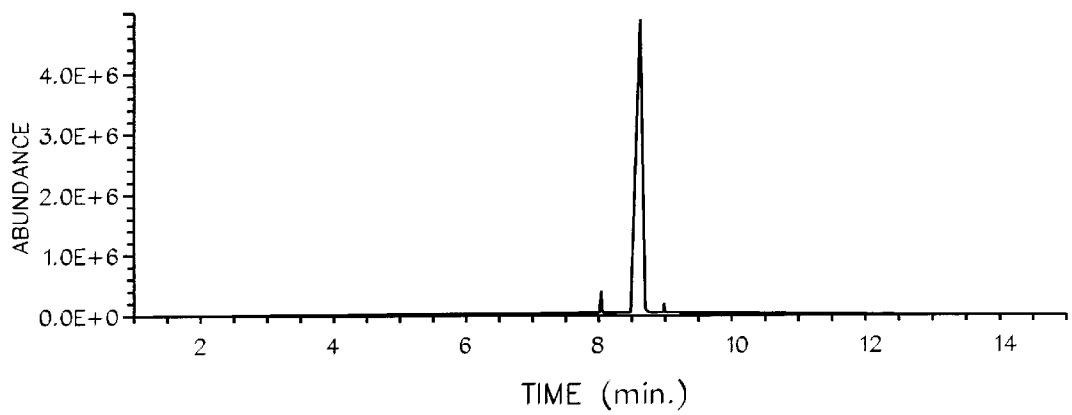
FIG. 23 Gas chromatography (upper trace) and mass spectrum (lower histogram) of (R)-5,6-dihydro-6-pentyl-2H-pyran-2-one (II). Chromatography was performed using an HP-1 crosslinked methyl silicone capillary column (12× 0.2 mm, 0.33 µm film) with helium as carrier gas at a flow rate of 1 ml/min, 50:1 split injector. Initial oven temperature was 100° C. raised to 136° C. at 4° C. min$^{-1}$.
Figure 23B:
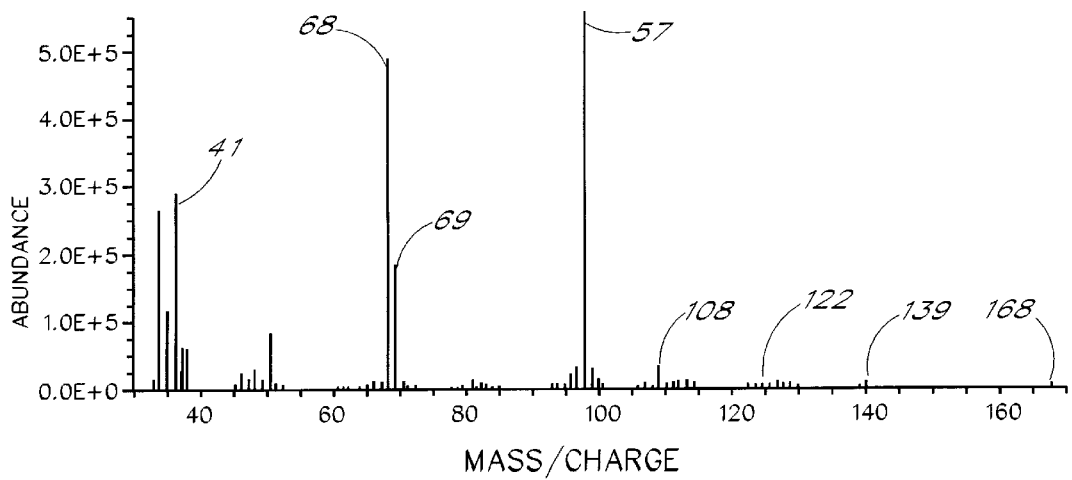
Figure 24A:
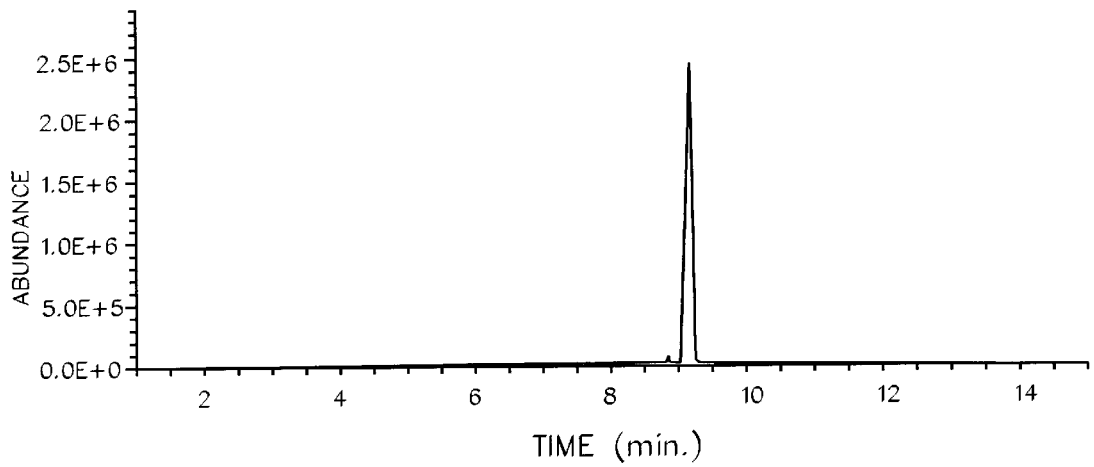
FIG. 24 Gas chromatography (upper trace) and mass spectrum (lower histogram) of (RS)-tetrahydro-6-pentyl-2H-pyran-2-one (IV). Chromatography was performed using an HP-1 crosslinked methyl silicone capillary column (12×0.2 mm, 0.33 µm film) with helium as carrier gas at a flow rate of 1 ml/min, 50:1 split injector. Initial oven temperature was 100° C. raised to 136° C. at 4° C. min$^{-1}$.
Figure 24B:
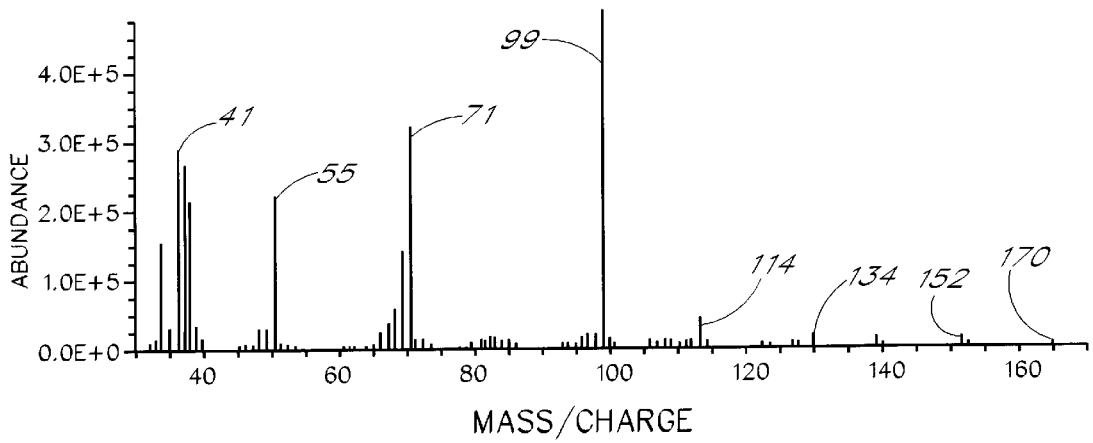
Figure 25A:
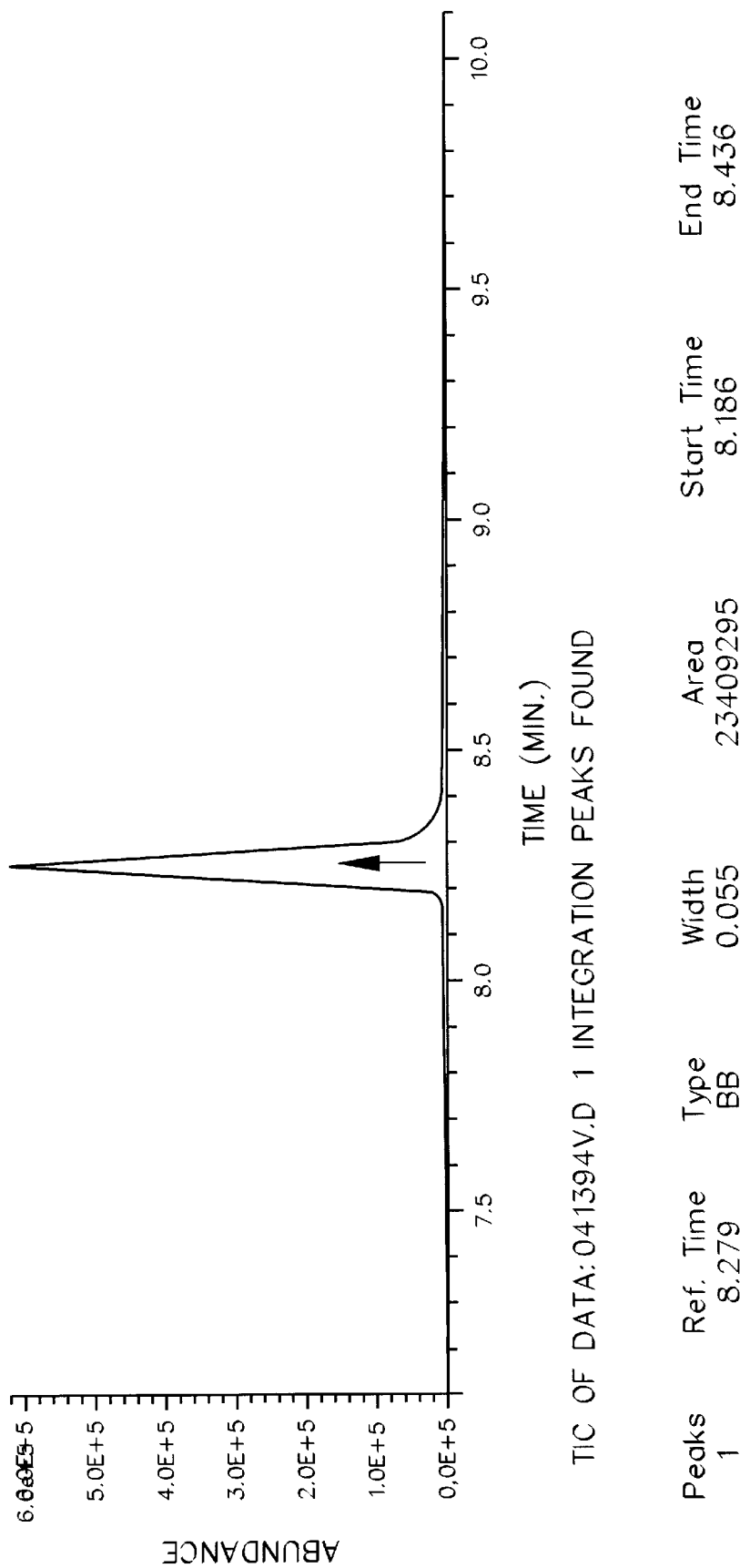
FIG. 25 Selected ion monitoring of replicate samples of a crude extract of *Trichoderma viride*. The integrated response employing aquisition parameters for the detection of A—6-pentyl-2H-pyran-2-one (I). B—(R)-5,6-dihydro-6-pentyl-2H-pyran-2-one (II). C—(RS)-tetrahydro-6-pentyl-2H-pyran-2-one (IV).
Figure 25B:
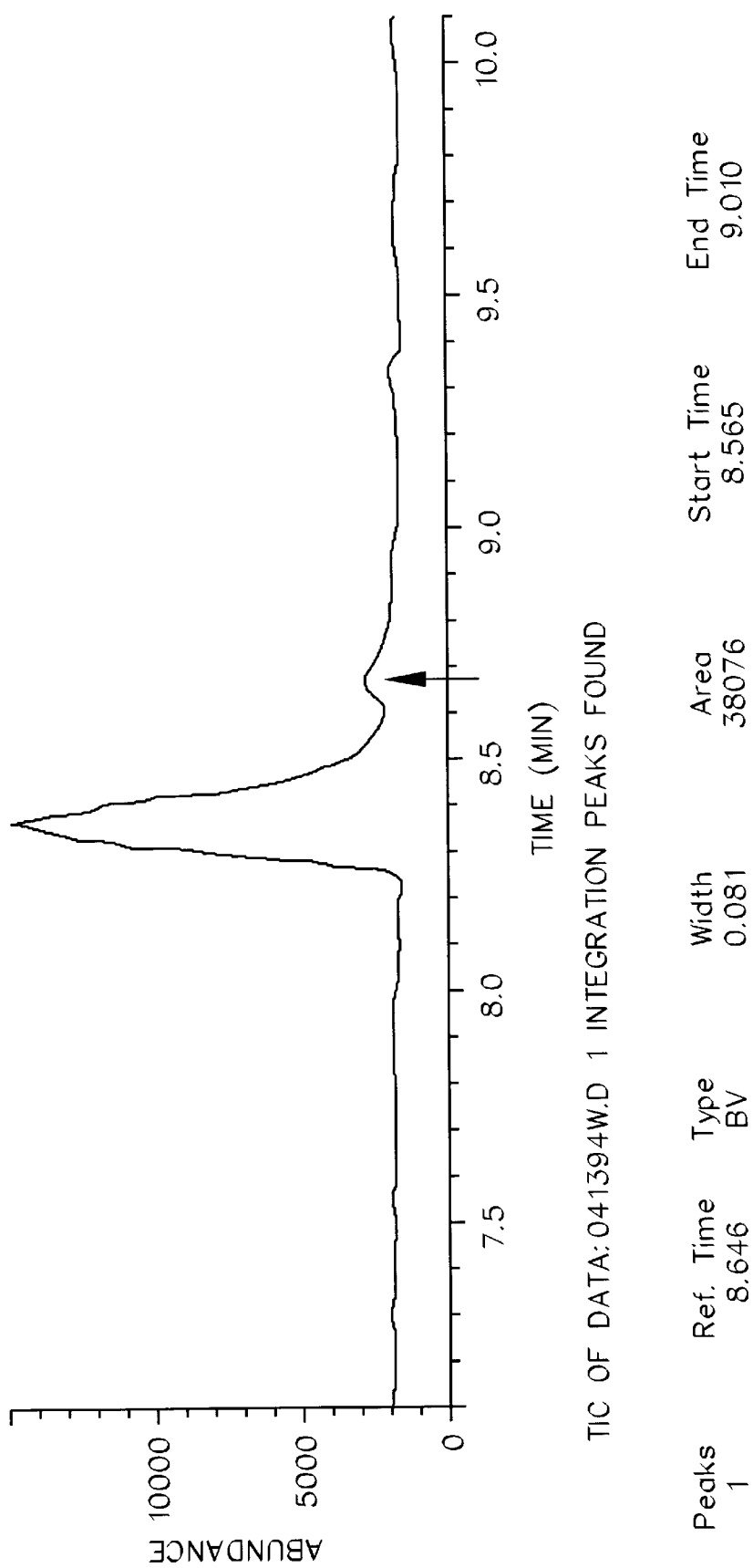
Figure 25C:
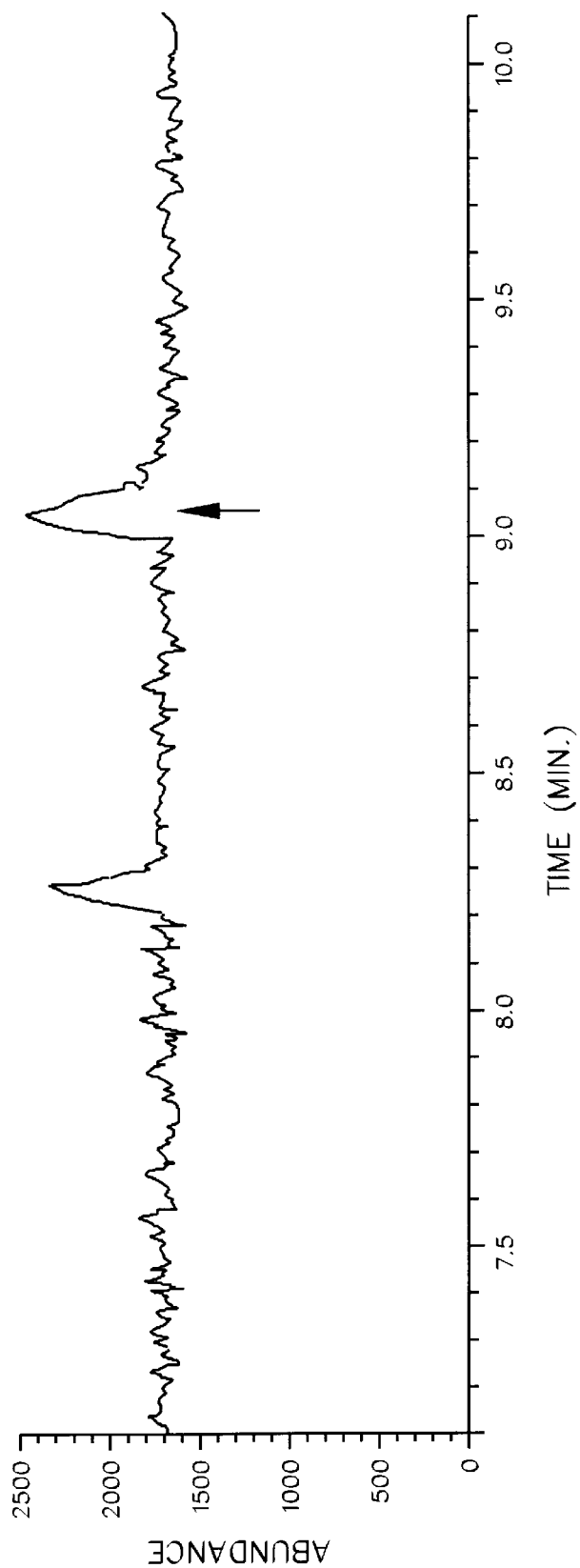

2.9 Analysis of 6-pentyl-2H-pyran-2-one Extacted From *Trichoderma viride* by Selected Ion Monitoring Commercially available samples of I (6-pentyl-2H-pyran-2-one) (ex Aldrich), II massoialactone) (ex International Frutarom Corporation and IV (RS)-tetrahydro-6-pentyl-2H-pyran-2-one) (ex Aldrich) were analysed by gas chromatography on a HP-1 crosslinked methyl silicone capillary column (12 m×0.2 mm, 0.33 µm film thickness) with helium as carrier gas at a flow rate of 1 ml $min^{-1}$. Initial oven temperature was 100° C. raised to 136° C. at 4° C. min$^{-1}$; 50:1 split injection. Mass spectra (electron ionisation, 70 eV) were obtained using an HP5970 mass selective detector (FIGS. 21, 22 and 23.) From the full spectra for each compound m/z ions were selected for monitoring (Table 19) [3] and acquisition parameter files established for detection of each compound by selected ion monitoring. Calibration curves for the integrated total ion response were obtained and a 1000-fold dilution of a crude extract containing I (6-pentyl-2H-pyran-2-one) obtained from *Trichoderma viride* analysed employing each of the parameter files established for detecting I, II and IV.

[3] Instrument resolution was 0.1 amu.

TABLE 19

Ions selected for selected ion monitoring and detection of 6-pentyl-2H-pyran-2-one (I), (R)-5,6-dihydro-6-pentyl-2H-pyran-2-one (II) and (RS)-tetrahydro-6-pentyl-2H-pyran-2-one (IV).

| COMPOUND | SELECTED IONS (m/z) |
| --- | --- |
| I | 94.8, 94.9, 95.0 and 95.1 |
| II | 96.9, 97.0, 97.1 and 97.2 |
| IV | 98.9, 99.0, 99.1 and 99.2 |

3. RESULTS

The results of the above experiments are recorded in FIGS. 10 to 25 and in Tables 20 to 23 as follows:

TABLE 20

| | MIC (%, v/v) | | | | | |
| --- | --- | --- | --- | --- | --- | --- |
| TEST ORGANISM | I | II | III | IV | V | VI |
| Sclerotinia sp. | 0.1 | 0.1 | N.D. | 1.0 | N.D. | N.D. |
| Botrytis cinerea (ex Bala) #1 | 0.05 | 0.025 | 0.05 | 0.1 | 0.1 | 0.1 |
| B. cinerea (ex Bala) #2 | 0.05 | 0.05 | 0.05 | 0.1 | 0.1 | 0.1 |

Activity against Sclerotinia sp. Sc4 and isolates of *Botrytis cinerea* of 6-pentyl-2H-pyran-2-one (I), (R)-5,6-dihydro-6-pentyl-2-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). Test compounds were diluted in nutrient agar employing 0.025% (v/v) Tween 80 as emulsifier. Minimum inhibitory concentrations(MICs) are the lowest concentration in agar that totally inhibited outgrowth from the colony bearing agar plug employed as inoculum. [N.D. - not determined.]

TABLE 21

| | MIC (%, v/v) | | | | | |
| --- | --- | --- | --- | --- | --- | --- |
| TEST ORGANISM | I | II | III | IV | V | VI |
| *Diplodia pinea* (ICMP 5286) | 0.1 | 0.1 | 0.1 | 0.1 | 0.1 | 0.1 |
| *Ophiostoma piceae* (FK150) | 0.1 | 0.1 | 0.1 | 0.1 | 0.1 | 0.1 |
| *Cyclaneusma minus* (ex FRI) | 0.1 | 0.1 | 0.1 | 0.1 | 0.1 | 0.1 |

TABLE 21-continued

| | MIC (%, v/v) | | | | | |
| --- | --- | --- | --- | --- | --- | --- |
| TEST ORGANISM | I | II | III | IV | V | VI |

Activity against *Diplodia pinea* (ICMP 5286), *Ophiostoma picea* (FK 150) and *Cyclaneusma minus* (ex FRI) of 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI). Test compounds were diluted in nutrient agar employing 0.025% (v/v) Tween 80 asemulsifier. Minimum inhibitory concentrations (MICs) are the lowest concentration in agar for a ten fold dilution series that totally inhibited outgrowth from the colony bearing agar plug employed as inoculum.

TABLE 22

| CONTROL | I | II | III | IV | V | VI |
| --- | --- | --- | --- | --- | --- | --- |
| 91 | 76 | 84 | 96 | 97 | 94 | 92 |

Lettuce seed germination assay. Inhibition of the germination of 100 lettuce seeds cv. Webbs Wonderful was determined after three days incubation in the dark at 20° C. in the presence of test compound vapours; 6-pentyl-2H-pyran-2-one (I), (R)-5,6-dihydro-6-pentyl-2H-pyran-2-one (II), (RS)-dihydro-5-hexyl-2H-furan-2-one (III), (RS)-tetrahydro-6-pentyl-2H-pyran-2-one (IV), (RS)-dihydro-5-octyl-2H-furan-2-one (V) and (RS)-tetrahydro-6-heptyl-2H-pyran-2-one (VI).

TABLE 23

Compound II (massoialactone) was detected as a minor component of the crude extract of *Trichoderma viride*.

| COMPOUND | INTEGRATED SIM RESPONSE | CONCENTRATION ($\mu l\ ml^{-1}$) | RATIOS (%) |
| --- | --- | --- | --- |
| I | $2.341 \times 10^7$ | $1.8 \times 10^{-1}$ | 100 |
| II | $3.808 \times 10^4$ | $5 \times 10^{-4}$ | 0.27 |
| IV | $2.611 \times 10^4$ | $2.7 \times 10^{-4}$ | 0.15 |

Quantities of 6-pentyl-2H-pyran-2-one (I), (R)-5,6-dihydro-6-pentyl-2H-pyran-2-one (II) and (RS)-tetrahydro-6-pentyl-2H-pyran-2-one (IV) determined to be present in a crude preparation of I extracted from *Trichoderma viride*. Compounds were detected by selected ion monitoring.

DISCUSSION

In an evaluation of the antifungal activity of 6-pentyl-2H-pyran-2-one and a range of its synthetic analogs none were found to possess greater activity than the "lead" compound. [15] Particularly striking was the dramatic loss of activity demonstrated when only minor structural changes were made to 6-pentyl-2H-pyran-2-one such as replacement of the 6-pentyl moiety with a shorter or longer 6-alkyl substituent. Introduction of a desaturation into the alkyl side chain, i.e. the formation of the 6-pentenyl analog, yielded a compound, massoialactone, with in vitro activity comparable to that of 6-pentyl-2H-pyran-2-one.

Despite its ready availability little has been published concerning the biological activity of massoialactone. Suggestions have been made that the compound may serve as an insect attractant to facilitate spore dispersal. [16] From the in vitro data reported here massoialactone has been shown to possess broad spectrum antifungal activity. Furthermore this in vitro activity is dramatically superior to that of the other compounds tested.

Specific isolates of the yeast Aureobasidium sp. have been identified as producing large amounts of delactonised massoialactone as an extracellular ester (35 g/L.) [2] This material is described as being readily separable from the fermentation broth by centrifugation. Such isolates could provide economic and plentiful supplies of a "natural" form of massoialactone. This, combined with the demonstrated efficacy of massoialactone in in vivo models, identifies it as suitable for development as an environmentally benign, non-toxic antifungal compound.

Aspects of the present invention has been described by way of example only and it should be appreciated that modifications and additions may be made thereto without departing from the scope thereof as defined in the appended claims.

REFERENCES

1. Cutler, H. G., et al., 6-*Pentyl-pyrone from Trichoderma harzianum: Its Plants Growth Inhibitory and Antimicrobial Properties*. Agricultural and Biological Chemistry, 1986. 50(11): p. 2943–2945.

2. Kurosawa, T., et al., *Extracellular accumulation of the polyol lipids, 3,5-dihydroxydecanoyl and 5-hydroxy-2-decenoyl esters of arabitol and mannitol, by* Aureobasidium sp. Biosci. Biotech. Biochem., 1994. 58(11): p. 2057–2060.

3. Garnero, J., et al. *Flavouring sustances: design of 6-alkyl- (and 6,6-dialkyl-) 5,6-dihydro-2-pyrones*. in *Flavors and Fragrances: a World perspective*. 1986. Washington, D.C., U.S.A.: Elsevier Science Publishers.

4. Yu, L. and Z. Wang, *Enantioselective total synthesis of 6R-(-)-massoialactone*. Chin. Chem. Lett., 1993. 4(1): p. 1–2.

5. Takano, S., M. Setoh, and K. Ogasawara, *An enantiospecific route to (6R)-(-)-massoialactone and (4R,6R)-(+)-4-hydroxy-6-pentylvalerolactone*. Tetrahedron: Asymmetry, 1992. 3(4): p. 533–534.

6. Bennett, F., D. W. Knight, and G. Fenton, *Total syntheses of natural (+)-(4R, 6R)-4-hydroxy-6-pentylvalerolactone and of (-)-(6R)-massoialactone*. J. Chem. Soc. Perkin Trans. 1, 1991: p. 1543–1547.

7. Pirkle, W. H. and P. E. Adams, *Enantiomerically pure lactones. 3. Synthesis of and stereospecific conjugate additions to α,β-3-unstaurated lactones*. J. Org. Chem., 1980. 45: p. 4117–4121.

8. Katsuta, Y., *Production of (R)-(-)-2-decen-5-olide*, in *Patent abstracts of Japan* 02059564 A. 1990, T Hasegawa Co. Ltd.: Japan.

9. Hoeyer, T., A. Kjaer, and J. Lykkesfeldt, *A convenient synthesis of homochiral delta alkylated alpha,beta unsaturated delta-lactone*. Coolect. Czech. Chem. Commun., 1991. 56(5): p. 1042–1051.

10. Fehr, C., J. Galindo, and G. Ohloff, *Novel Approach to the synthesis of 6-substituted 5,6-dihydro-2(2H)-pyranones*. Helvetica Chimica Acta, 1981. 64(5): p. 1247–1256.

11. Pan, X. -F. and C. Zhang. *An efficient and stereoselective synthesis of (-)-massoialactone*. in *Progress in Drug Development from Medicinal Plants*. 1996. Hangzhou, China: UNESCO.

12. Cutler, H. G. *A Fresh Look at the Wheat Coleoptile Bioassay*. in 11*th Annual Meeting of the Plant Growth Regulator Society of America*. 1984.

13. Kurtz, T. E., et al., *Short-cut Multiple Comparisons for Balanced Single and Double Classification: Part* 1, *Results*. Technometrics, 1965. 7: p. 95–61.

14. Claydon, N., et al., *Antifungal Alkyl Pyrones of Trichoderma harzianum*. Transactions of the British Mycological Society, 1987. 88(4): p. 503–513.

15. Dickinson, J. M., D. Phil. Thesis, University of Sussex, 1988.

16. Nago, H. and M. Matsumoto, *An ecological role of volatiles produced by Lasiodiplodia theobromae*. Biosci. Biotech. Biochem., 1994. 58(7): p. 1267–1272.

What is claimed is:

1. A method of preventing or at least inhibiting growth of a fungus which comprises the step of applying massoialactone to said fungus or to a locus thereof.

2. A method according to claim 1, wherein said massoialactone is applied in a composition comprising said massoialactone together with an agronomically acceptable carrier therefor.

3. A method according to claim 2, wherein said composition further comprises at least one additional antifungal compound.

4. A method according to claim 2, wherein said composition further comprises a Trichoderma isolate which produces a metabolite selected from the group consisting of 6-pentyl-α-pyrone and delta-decanolactone.

5. A method according to claim 1, wherein the fungus being inhibited is selected from the group consisting of *Botrytis cinerea*, Armillaria, Phytophthora, *Nectria galligena, Sclerottum rolfsil, Rhizoctonia solanl, Sclerottum ceplvorum, Macrophomina phaesolina, Fusartum oxysporum, Verticillium albostrum, Chondrostereum purpureum, Scletotinia sclerottorum, Pythium ultimum* and *Corticum rolfsil*.

6. A method according to claim 1, wherein said locus is a biological surface susceptible to unwanted fungal growth.

7. A method according to claim 6, wherein said surface is a surface of a plant or a plant product.

8. A method according to claim 7, wherein said surface is the external surface of a fruit or vegetable.

9. A method according to claim 7, wherein said surface is a timber surface.

10. A method according to claim 7, wherein said surface is an external surface of a plant seed.

* * * * *